US012755850B2

(12) United States Patent
Gaudilliere et al.

(10) Patent No.: US 12,755,850 B2
(45) Date of Patent: Oct. 6, 2026

(54) SYSTEMS AND METHODS TO GENERATE A SURGICAL RISK SCORE AND USES THEREOF

(71) Applicant: The Board of Trustees of the Leland Stanford Junior University, Stanford, CA (US)

(72) Inventors: Brice Gaudilliere, Palo Alto, CA (US); Nima Aghaeepour, Palo Alto, CA (US); Julien Hedou, San Francisco, CA (US); Kristen Rumer, Fort Lauderdale, FL (US); Martin S. Angst, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/551,149

(22) PCT Filed: Mar. 18, 2022

(86) PCT No.: PCT/US2022/071226
§ 371 (c)(1),
(2) Date: Sep. 18, 2023

(87) PCT Pub. No.: WO2022/198239
PCT Pub. Date: Sep. 22, 2022

(65) Prior Publication Data

US 2025/0022604 A1 Jan. 16, 2025

Related U.S. Application Data

(60) Provisional application No. 63/162,912, filed on Mar. 18, 2021.

(51) Int. Cl.
*G16H 50/30* (2018.01)
*G16B 25/10* (2019.01)
(Continued)

(52) U.S. Cl.
CPC ............ *G16H 50/30* (2018.01); *G16B 25/10* (2019.02); *G16B 40/00* (2019.02); *G16H 50/20* (2018.01); *G16H 50/70* (2018.01)

(58) Field of Classification Search
CPC ........ G16H 50/30; G16H 50/70; G16H 50/20; G16B 25/10; G16B 40/00
See application file for complete search history.

(56) References Cited

U.S. PATENT DOCUMENTS 7,018,850 B2 3/2006 Raymond et al.
9,141,622 B1 * 9/2015 Moore ................ G06F 18/2415
(Continued)

FOREIGN PATENT DOCUMENTS

CN 112289455 A * 1/2021 ............. G16H 50/20
EP 4308017 A1 1/2024
(Continued)

OTHER PUBLICATIONS

Salinas et al., "A Prediction Model for Preoperative Risk Assessment in Endometrial Cancer Utilizing Clinical and Molecular Variables," Int. J. Mol. Sci. 2019, 20, 1205; doi:10.3390/ijms20051205. (Year: 2019).*
(Continued)

*Primary Examiner* — Jonathon A. Szumny
(74) *Attorney, Agent, or Firm* — KPPB LLP

(57) ABSTRACT

Embodiments herein describe systems and methods to generate a surgical risk score. Various embodiments obtaining multi-omics data from an individual, such as genomics, transcriptomics, and proteomics. In certain embodiments, a machine algorithm is used to generate the surgical risk score based on the multi-omics data. In further embodiments, clinical data is further used in the determination of the surgical risk score.

20 Claims, 20 Drawing Sheets

(51) Int. Cl.

| | |
|---|---|
| ***G16B 40/00*** | (2019.01) |
| ***G16H 50/20*** | (2018.01) |
| ***G16H 50/70*** | (2018.01) |

(56) References Cited

U.S. PATENT DOCUMENTS

| | | | | |
|---|---|---|---|---|
| 9,311,568 | B1 * | 4/2016 | Feller | G06V 20/62 |
| 11,568,992 | B2 * | 1/2023 | Jordan | G16H 50/70 |
| 11,694,775 | B1 * | 7/2023 | Maier | G06N 7/01 705/2 |
| 11,848,106 | B1 * | 12/2023 | Wood | G16H 50/20 |
| 11,961,619 | B1 * | 4/2024 | LaBorde | G06N 3/02 |
| 2001/0006787 | A1 | 7/2001 | Payan | |
| 2007/0208516 | A1 * | 9/2007 | Kutsyy | G06F 18/214 702/19 |
| 2008/0244008 | A1 * | 10/2008 | Wilkinson | H04L 67/56 709/205 |
| 2012/0123108 | A1 * | 5/2012 | Lukomski | C07K 14/32 536/24.33 |
| 2012/0178183 | A1 | 7/2012 | Nolan et al. | |
| 2012/0329675 | A1 * | 12/2012 | Olson | C12Q 1/025 506/10 |
| 2014/0067728 | A1 * | 3/2014 | Ogren | G06F 18/214 706/54 |
| 2014/0136467 | A1 * | 5/2014 | Berbari | A61B 5/7275 706/52 |
| 2015/0241445 | A1 * | 8/2015 | Gaudilliere | G01N 33/6863 435/7.24 |
| 2016/0275413 | A1 * | 9/2016 | Shi | G06N 20/00 |
| 2018/0330824 | A1 | 11/2018 | Athey et al. | |
| 2019/0122330 | A1 | 4/2019 | Saget et al. | |
| 2019/0279082 | A1 * | 9/2019 | Moloney | G06F 18/285 |
| 2020/0015722 | A1 * | 1/2020 | Gopinathan | A61B 5/686 |
| 2020/0105413 | A1 * | 4/2020 | Vladimirova | G16H 20/30 |
| 2020/0161000 | A1 * | 5/2020 | Bihorac | G06N 20/20 |
| 2020/0321077 | A1 | 10/2020 | Taylor et al. | |
| 2021/0224599 | A1 * | 7/2021 | Tajima | G06F 18/24147 |
| 2021/0287111 | A1 * | 9/2021 | Zhou | G06Q 30/016 |
| 2021/0303986 | A1 * | 9/2021 | Saha | G06N 3/08 |
| 2021/0327540 | A1 * | 10/2021 | Schobel | G16H 50/20 |
| 2022/0208383 | A1 * | 6/2022 | Li | G06T 7/246 |
| 2022/0237999 | A1 * | 7/2022 | Shelton, IV | A61B 5/7267 |
| 2022/0285028 | A1 * | 9/2022 | Ediebah | G16H 50/20 |
| 2022/0364171 | A1 * | 11/2022 | Vermeire | C07K 16/2839 |
| 2023/0027978 | A1 * | 1/2023 | Gaborit | G16H 50/20 |
| 2023/0197224 | A1 * | 6/2023 | Bradley | G16H 10/60 705/2 |
| 2023/0220477 | A1 * | 7/2023 | Vachot | C12Q 1/6813 435/6.11 |
| 2023/0256057 | A1 * | 8/2023 | Inchauspe | C12N 15/86 424/93.2 |
| 2023/0273222 | A1 * | 8/2023 | Griesbeck | G01N 33/6893 436/86 |
| 2023/0284983 | A1 * | 9/2023 | Kashiwagi | G16H 20/10 |
| 2023/0313326 | A1 * | 10/2023 | Vachot | C12Q 1/6883 435/5 |
| 2024/0093318 | A1 * | 3/2024 | Barnes | C12Q 1/6883 |
| 2024/0136071 | A1 * | 4/2024 | Chen | G16H 50/50 |

FOREIGN PATENT DOCUMENTS

| | | | |
|---|---|---|---|
| JP | 2024512454 | A | 3/2024 |
| KR | 20230158101 | A | 11/2023 |
| WO | 1999054494 | A2 | 10/1999 |
| WO | 2017141169 | A1 | 8/2017 |
| WO | 2018220600 | A1 | 12/2018 |
| WO | 2020118274 | A1 | 6/2020 |
| WO | 2022198239 | A1 | 9/2022 |

OTHER PUBLICATIONS

Thottakkara et al., "Application of Machine Learning Techniques to High-Dimensional Clinical Data to Forecast Postoperative Complications," PLoS One 11(5): e0155705; doi:10.1371/journal.pone.0155705. (Year: 2016).*

Oh et al., "Computational methods using genome-wide association studies to predict radiotherapy complications and to identify correlative," Scientific Reports | 7:43381 | DOI: 10.1038/srep43381. (Year: 2017).*

Cao et al., "Deep Learning Neural Networks to Predict Serious Complications After Bariatric Surgery: Analysis of Scandinavian Obesity Surgery Registry Data," JMIR Med Inform 2020;8(5):e15992) doi: 10.2196/15992. (Year: 2020).*

Kang et al., "Development of a Clinical and Genetic Prediction Model for Early Intestinal Resection in Patients with Crohn's Disease: Results from the IMPACT Study," J. Clin. Med. 2021, 10, 633. https://doi.org/10.3390/jcm10040633. (Year: 2021).*

"Overview of Sparse Modeling," https://goodboychan.github.io/machine_learning/2020/09/07/01-Overview-of-Sparse-Modeling.html. (Year: 2020).*

Razzaghi et al., "Predictive models for bariatric surgery risks with imbalanced medical datasets," Annals of Operations Research (2019) 280:1-18; https://doi.org/10.1007/s10479-019-03156-8. (Year: 2019).*

Pedersen et al., "Ranking factors involved in diabetes remission after bariatric surgery using machine-learning integrating clinical and genomic biomarkers," npj Genomic Medicine (2016) 1, 16035; doi:10.1038/npjgenmed.2016.35. (Year: 2016).*

Hanifah et al., "SMOTE Bagging Algorithm for Imbalanced Dataset in Logistic Regression Analysis (Case: Credit of Bank X)"; Applied Mathematical Sciences, vol. 9, 2015, No. 138, 6857-6865; HIKARI Ltd, www.m-hikari.com; http://dx.doi.org/10.12988/ams.2015.58562. (Year: 2015).*

Extended European Search Report received for European Application No. 22772391.3, Search completed Dec. 18, 2024, Mailed Jan. 9, 2025, 13 pgs.

International Preliminary Report on Patentability received for International Application No. PCT/US2022/071226, Report issued Sep. 12, 2023, Mailed Sep. 28, 2023, 05 pgs.

International Search Report and Written Opinion received for International Application No. PCT/US2022/071226, Search completed Apr. 27, 2022, Mailed May 23, 2022, 22 pgs.

Aghaeepour et al., "An immune clock of human pregnancy", Science Immunology, vol. 2, No. 15, Article eaan2946, Sep. 1, 2017, 11 pgs., doi: 10.1126/sciimmunol.aan2946.

Aghaeepour et al., "Deep Immune Profiling of an Arginine-Enriched Nutritional Intervention in Patients Undergoing Surgery", The Journal of Immunology, vol. 199, No. 6, Sep. 2017, pp. 2171-2180, doi: 10.4049/jimmunol.1700421.

Angele et al., "Clinical review: Immunodepression in the surgical patient and increased susceptibility to infection", Critical Care, vol. 6, No. 4, Aug. 2002, pp. 298-305, doi: 10.1186/cc1514.

Assarsson et al., "Homogenous 96-Plex PEA Immunoassay Exhibiting High Sensitivity, Specificity, and Excellent Scalability", PLoS One, vol. 9, No. 4, Article e95192, Apr. 22, 2014, 11 pgs., doi: 10.1371/journal.pone.0095192.

Ausubel et al., "Short Protocols in Molecular Biology", Wiley, 4th Edition, 1999, 1114 pgs. (Presented in 3 parts).

Baca et al., "Predicting Acute Pain After Surgery A Multivariate Analysis", Annals of Surgery, vol. 273, No. 2, Feb. 2021, pp. 289-298, doi: 10.1097/SLA.0000000000003400.

Bach, "Bolasso: Model Consistent Lasso Estimation Through the Bootstrap", arXiv:0804.1302v1 [cs.LG], Apr. 8, 2008, 26 pgs.

Bilimoria et al., "Development and Evaluation of the Universal ACS NSQIP Surgical Risk Calculator: A Decision Aid and Informed Consent Tool for Patients and Surgeons", Journal of the American College of Surgeons, vol. 217, No. 5, Nov. 2013, pp. 833-842.e1-3, doi: 10.1016/j.jamcollsurg.2013.07.385.

Bodenmiller et al., "Multiplexed mass cytometry profiling of cellular states perturbed by small-molecule regulators", Nature Biotechnology, vol. 30, No. 9, Sep. 2012, pp. 858-867, doi: 10.1038/nbt.2317.

Bone et al., "Immunologic Dissonance: A Continuing Evolution in Our Understanding of the Systemic Inflammatory Response Syndrome (SIRS) and the Multiple Organ Dysfunction Syndrome

(56) References Cited

OTHER PUBLICATIONS (MODS)", Annals of Internal Medicine, vol. 125, No. 8, Oct. 15, 1996, pp. 680-687, doi: 10.7326/0003-4819-125-8-199610150-00009.
Breiman, "Random Forests", Machine Learning, vol. 45, No. 1, Oct. 2001, pp. 5-32, doi: 10.1023/A:1010933404324.
Brown et al., "Utility of Biomarkers to Improve Prediction of Readmission or Mortality After Cardiac Surgery", Annals of Thoracic Surgery, vol. 106, No. 5, Nov. 2018, pp. 1294-1301, doi: 10.1016/j.athoracsur.2018.06.052.
Candes et al., "Panning for gold: 'model-X'knockoffs for high dimensional controlled variable selection", Journal of the Royal Statistical Society Series B: Statistical Methodology, vol. 80, No. 3, Jun. 2018, pp. 551-577, doi: 10.1111/rssb.12265.
Carlson et al., "The Maine Women's Health Study: I. Outcomes of Hysterectomy", Obstetrics & Gynecology, vol. 83, No. 4, Apr. 1994, pp. 556-565, doi: 10.1097/00006250-199404000-00012.
Chattopadhyay et al., "Quantum dot semiconductor nanocrystals for immunophenotyping by polychromatic flow cytometry", Nature Medicine, vol. 12, No. 8, Aug. 2006, pp. 972-977, doi: 10.1038/nm1371.
Choileain et al., "Cell Response to Surgery", JAMA Surgery, vol. 141. No. 11, Nov. 1, 2006, pp. 1132-1140, doi: 10.1001/archsurg.141.11.1132.
Cohen et al., "An Examination of American College of Surgeons NSQIP Surgical Risk Calculator Accuracy", Journal of the American College of Surgeons, vol. 224, No. 5, May 2017, pp. 787-795.e1, doi: 10.1016/j.jamcollsurg.2016.12.057.
De Mooij, "Systematic Review of the Role of Biomarkers in Predicting Anastomotic Leakage Following Gastroesophageal Cancer Surgery", Journal of Clinical Medicine, vol. 8, No. 11, Article 2005, Nov. 17, 2019, 18 pgs., doi: 10.3390/jcm8112005.
Dorow et al., "Risk Factors for Postoperative Pain Intensity in Patients Undergoing Lumbar Disc Surgery: A Systematic Review", PLoS One, vol. 12, No. 1, Article e0170303, Jan. 20, 2017, 24 pgs., doi: 10.1371/journal.pone.0170303.
Eamer et al., "Review of risk assessment tools to predict morbidity and mortality in elderly surgical patients", The American Journal of Surgery, vol. 216, No. 3, Sep. 2018, pp. 585-594, doi: 10.1016/j.amjsurg.2018.04.006.
Erkki et al., "Lanthanide Chelates as New Fluorochrome Labels for Cytochemistry", Journal of Histochemistry and Cytochemistry, vol. 36, No. 11, 1988, pp. 1449-1451, doi: 10.1177/36.11.3049792.
Eyraud et al., "LARS: A learning algorithm for rewriting systems", Machine Learning, vol. 66, Aug. 4, 2006, pp. 7-31, doi: 10.1007/s10994-006-9593-8.
Fong et al., "Identification of Plasma Proteome Signatures Associated With Surgery Using SOMAscan", Annals of Surgery, vol. 273, No. 4, Apr. 2021, pp. 732-742, doi: 10.1097/SLA.0000000000003283.
Fragiadakis et al., "Patient-specific Immune States before Surgery Are Strong Correlates of Surgical Recovery", Anesthesiology, vol. 123, No. 6, Dec. 2015, pp. 1241-1255, doi: 10.1097/ALN.0000000000000887.
Friedman et al., "Applications of the lasso and grouped lasso to the estimation of sparse graphical models", Stanford University, Mar. 10, 2010, 22 pgs.
Gaudilliere et al., "Clinical recovery from surgery correlates with single-cell immune signatures", Science Translational Medicine, vol. 6, No. 255, Article 255ra131, Sep. 24, 2014, 12 pgs., doi: 10.1126/scitranslmed.3009701.
Gold et al., "Aptamer-Based Multiplexed Proteomic Technology for Biomarker Discovery", PLoS One, vol. 5. No. 12, Article e15004, Dec. 7, 2010, 17 pgs., doi: 10.1371/journal.pone.0015004.
Healy et al., "Hospital and Payer Costs Associated With Surgical Complications", JAMA Surgery, vol. 151, No. 9, Sep. 2016, pp. 823-830, doi: 10.1001/jamasurg.2016.0773.
Herman, "Chapter 8 Resonance Energy Transfer Microscopy", Methods in Cell Biology, vol. 30, 1989, pp. 219-243, doi: 10.1016/S0091-679X(08)60981-4.
Hotchkiss et al., "The Pathophysiology and Treatment of Sepsis", The New England Journal of Medicine, vol. 348, No. 2, Jan. 9, 2003, pp. 138-150, doi: 10.1056/NEJMra021333.
Kjerulff et al., "A Comparison of Alternative Ways of Measuring Fatigue among Patients Having Hysterectomy", Medical Care, vol. 33, No. 4, Apr. 1995, pp. AS156-AS163, doi: 10.2307/3766622.
Liangos et al., "Whole Blood Transcriptomics in Cardiac Surgery Identifies a Gene Regulatory Network Connecting Ischemia Reperfusion with Systemic Inflammation", PLoS One, vol. 5, No. 10, Article e13658, Oct. 27, 2010, 12 pgs., doi: 10.1371/journal.pone.0013658.
Meinshausen, "Relaxed Lasso", Computational Statistics & Data Analysis, vol. 52, No. 1, Sep. 15, 2007, pp. 374-393, doi: 10.1016/j.csda.2006.12.019.
Meinshausen et al., "High-Dimensional Graphs and Variable Selection with the Lasso", The Annals of Statistics, vol. 34, No. 3, Jun. 2006, pp. 1436-1462, doi: 10.1214/009053606000000281.
Ruczinski et al., "Logic Regression", Journal of Computational and Graphical Statistics, vol. 12, No. 3, Sep. 2003, pp. 475-512, doi: 10.1198/1061860032238.
Shapiro, "Practical Flow Cytometry", John Wiley & Sons, Fourth Edition, Jul. 2003, 5 pgs.
Stoecklein et al., "Trauma equals danger-damage control by the immune system", Journal of Leukocyte Biology, vol. 92, No. 3, Sep. 2012, pp. 539-551, doi: 10.1189/jlb.0212072.
Sun et al., "Incidence of and Risk Factors for Chronic Opioid Use Among Opioid-Naive Patients in the Postoperative Period", JAMA Internal Medicine, vol. 176, No. 9, 2016, pp. 1286-1293, doi: 10.1001/jamainternmed.2016.3298.
Tanner et al., "Multiplex bio-assay with inductively coupled plasma mass spectrometry: Towards a massively multivariate single-cell technology", Spectrochimica Acta Part B: Atomic Spectroscopy, vol. 62, No. 3, Mar. 2007, pp. 188-195, doi: 10.1016/j.sab.2007.01.008.
Tibshirani, "Regression Shrinkage and Selection via the Lasso", Journal of the Royal Statistical Society: Series B (Methodological), vol. 58, No. 1, Jan. 1996, pp. 267-288, doi: 10.1111/j.2517-6161.1996.tb02080.x.
Tibshirani et al., "Diagnosis of multiple cancer types by shrunken centroids of gene expression", Proceedings of the National Academy of Sciences, vol. 99, No. 10, May 14, 2002, pp. 6567-6572, doi: 10.1073/pnas.082099299.
Van Helmond et al., "PredictingPersistent Pain After Surgery: Can Predicting the Weather Serve as an Example?", Anesthesia & Analgesia, vol. 127, No. 5, Nov. 2018, pp. 1264-1267, doi: 10.1213/ANE.0000000000003318.
Van Hest et al., "Efficient introduction of alkene functionality into proteins in vivo", FEBS Letters, vol. 428, No. 1-2, May 22, 1998, pp. 68-70, doi: 10.1016/S0014-5793(98)00489-X.
Vivian IP et al., "Predictors of Postoperative Pain and Analgesic Consumption A Qualitative Systematic Review", Anesthesiology, vol. 111, No. 3, Sep. 1, 2009, pp. 657-677, doi: 10.1097/ALN.0b013e3181aae87a.
Wang et al., "Random Lasso", The Annals of Applied Statistics, vol. 5, No. 1, Mar. 2011, pp. 468-485, doi: 10.1214/10-AOAS377.
Weiser et al., "An estimation of the global vol. of surgery: a modelling strategy based on available data", The Lancet, vol. 372, No. 9633, Jul. 22, 2008, pp. 139-144, doi: 10.1016/s0140-6736(08)60878-8.
Zou et al., "Regularization and variable selection via the elastic net", Journal of the Royal Statistical Society. Series B (Statistical Methodology), vol. 67, No. 2, Mar. 9, 2005, pp. 301-320, doi: 10.1111/j.1467-9868.2005.00503.x.

* cited by examiner

Algorithm 1 MOB

Input: $X$ matrix of original features, $Y$ vector of outcome values, $N$ number of spiking procedure repetitions, $M$ number of bootstrap replicates, $\lambda$ fold-enrichment selection threshold.

for $i = 1, 2, \ldots, N$ do
    Spike artificial features by permutation of $X$ creating a matrix of original and spiked features $X^i$.
    for $j = 1, 2, \ldots, M$ do
        Generate bootstrap samples $(X_j^i, Y_j)$.
        Compute elastic net estimate $w_j$ from $(X_j^i, Y_j)$.
        Extract the non-zero coefficients and their associated features.
    end for
    Extract each feature's selection frequency.
end for
Compute the distribution of feature selection frequencies.
Compute the selection fold-enrichment for biological features over artificial features.
Select features with selection fold-enrichment above $\lambda$

Figure 3A

Algorithm 1 MOB v.2

Input: $X$ matrix of original features of dimension $n$ (number of samples) by $p$ (number of features), $Y$ vector of outcome values, $M$ number of bootstrap replicates, $\kappa$ fold-enrichment selection threshold, $\Lambda$ the vector of L1 and L2 regularization parameters to test.

for $i = 1, 2, \ldots, M$ do

Spike artificial features by permutation or random sampling of $X$, creating a matrix of juxtaposed original and spiked features $X^i$.

for $\lambda$ in $\Lambda$ do

Generate bootstrap samples $(X^i_j, Y_j)$, with a size $\alpha n$ by $p + p'$, where $\alpha$ is the bootstrap sampling coefficient, and $p'$ the number of spiked features.

Fit the sparse regression techniques models (e.g., Lasso and Elastic Net ), with the hyperparameters $\lambda$, and the estimate for the coefficients, $w_j$, from $(X^i_j, Y_j)$.

Extract the non-zero coefficients and their associated features.

end for

Extract each feature's selection frequency.

end for

$max_{feature} = max_{\Lambda} frequency(feature)$

Compute the distribution of feature selection frequencies for artificial features.

Select non artificial features with selection fold-enrichment above $\kappa.median(max_{artificialfeatures})$

Figure 3B

SYSTEMS AND METHODS TO GENERATE A SURGICAL RISK SCORE AND USES THEREOF

CROSS-REFERENCE TO RELATED APPLICATIONS

The current application is a national stage of PCT Patent Application No. PCT/US2022/071226 entitled "Systems and Methods to Generate a Surgical Risk Score and Uses Thereof" filed Mar. 18, 2022, which claims priority to U.S. Provisional Patent Application No. 63/162,912, filed Mar. 18, 2021, entitled "Systems and Methods to Generate a Surgical Risk Score and Uses Thereof" to Gaudilliere et al.; the disclosures of which are hereby incorporated by reference in their entirety.

CROSS-REFERENCE TO RELATED APPLICATIONS

The current application claims priority to U.S. Provisional Patent Application No. 63/162,912, filed Mar. 18, 2021, entitled "Systems and Methods to Generate a Surgical Risk Score and Uses Thereof" to Gaudilliere et al.; the disclosure of which is hereby incorporated by reference in its entirety.

STATEMENT REGARDING FEDERALLY SPONSORED RESEARCH OR DEVELOPMENT

This invention was made with Government support under contracts GM137936 and GM138353 awarded by the National Institutes of Health. The Government has certain rights in the invention.

FIELD OF THE INVENTION

The present invention relates to predicting surgical outcome, more specifically, using a machine learning model to predict surgical outcomes, such as post-operative infections and surgical site complications, from clinical and multiomics data.

BACKGROUND

Over 300 million operations are performed annually worldwide, a number that is expected to increase. Surgical complications including infection, protracted pain, functional impairment, and end-organ damage occur in 10-60% of surgeries, causing personal suffering, longer hospital stays, readmissions, and significant socioeconomic burden. After major abdominal operations, surgical site complications (SSCs), including superficial or deep wound infections, organ space infections, anastomotic leaks, fascial dehiscence, and incisional hernias, are some of the most devastating, costly, and common surgical complications occurring in up to 25% of patients. (See e.g., Healy M A et al. *JAMA Surg* 2016; 151(9):823-30; the disclosure of which is hereby incorporated by reference herein in its entirety.)

The accurate prediction of SSC risk for individual patients is critically important to guide high-quality surgical decision making, including optimizing preoperative interventions and timing of surgery. Existing risk prediction tools are based on clinical parameters and are insufficient to estimate an individual patient's risk for SSCs. (See e.g., Eamer G, et al. Am J Surg 2018; 216(3):585-594; and Cohen M E et al. J Am Coll Surg 2017; 224(5):787-795 e1; the disclosures of which are hereby incorporated by reference herein in their entireties.) As such, there is a need in the field for a robust tool to predict SSCs with more accuracy.

SUMMARY OF THE INVENTION

This summary is meant to provide some examples and is not intended to be limiting of the scope of the invention in any way. For example, any feature included in an example of this summary is not required by the claims, unless the claims explicitly recite the features. Various features and steps as described elsewhere in this disclosure may be included in the examples summarized here, and the features and steps described here and elsewhere can be combined in a variety of ways.

In some aspects, the techniques described herein relate to a method for determining the risk for a surgical complication for an individual following surgery, including: obtaining or having obtained values of a plurality of features, where the plurality of features includes omic biological features and clinical features; computing a surgical risk score for the individual based on the plurality of features using a model obtained via a machine learning technique; and providing an assessment of the patient's risk for developing a surgical complication based on the computed surgical risk score.

In some aspects, the techniques described herein relate to a method, where obtaining or having obtained values of a plurality of features includes: obtaining or having obtained a sample for analysis from the individual subject to surgery; and measuring or having measured the values of a plurality of omic biological and clinical features.

In some aspects, the techniques described herein relate to a method, where the plurality of features further includes demographic features.

In some aspects, the techniques described herein relate to a method, where omic biological features include at least one feature of the group: a genomic feature, a transcriptomic feature, a proteomic feature, a cytomic feature, and a metabolomic feature.

In some aspects, the techniques described herein relate to a method, where the machine learning model is trained using a bootstrap procedure on a plurality of individual data layers, where each data layer represents one type of data from the plurality of features and at least one artificial feature.

In some aspects, the techniques described herein relate to a method, where each type is chosen: genomic, transcriptomic, proteomic, cytomic, metabolomic, clinical and demographic.

In some aspects, the techniques described herein relate to a method, where: each data layer includes data for a population of individuals; where each feature includes feature values for all individuals in the population of individuals; and for a respective data layer, each artificial feature is obtained from a non-artificial feature among the plurality of features, via a mathematical operation performed on the feature values of the non-artificial feature.

In some aspects, the techniques described herein relate to a method, where the mathematical operation is chosen among: a permutation, a sampling with replacement, a sampling without replacement, a combination, a knockoff and an inference.

In some aspects, the techniques described herein relate to a method, where the model includes weights ($\beta_i$) for a set of selected biological and clinical or demographic features; during the machine learning and for each data layer, for every repetition of the bootstrap, initial weights ($w_j$) are computed for the plurality of features and the at least one artificial feature associated with that data layer using an initial statistical learning technique, and at least one selected feature is determined for each data layer, based on a statistical criteria depending on the computed initial weights ($w_j$).

In some aspects, the techniques described herein relate to a method, where the initial statistical learning technique is selected from a regression technique and a classification technique.

In some aspects, the techniques described herein relate to a method, where the initial statistical learning technique is selected from a sparse technique and a non-sparse technique.

In some aspects, the techniques described herein relate to a method, where the sparse technique is selected from a Lasso technique and an Elastic Net technique.

In some aspects, the techniques described herein relate to a method, where the statistical criteria depends on significant weights among the computed initial weights ($w_j$).

In some aspects, the techniques described herein relate to a method, where the significant weights are non-zero weights, when the initial statistical learning technique is a sparse regression technique.

In some aspects, the techniques described herein relate to a method, where the significant weights are weights above a predefined weight threshold, when the initial statistical learning technique is a non-sparse regression technique.

In some aspects, the techniques described herein relate to a method, where the initial weights ($w_j$) are further computed for a plurality of values of a hyperparameter, where the hyperparameter is a parameter whose value is used to control the learning process.

In some aspects, the techniques described herein relate to a method, where the hyperparameter is a regularization coefficient used according to a respective mathematical norm in the context of a sparse initial technique.

In some aspects, the techniques described herein relate to a method, where the mathematical norm is a p-norm, with p being an integer.

In some aspects, the techniques described herein relate to a method, where the hyperparameter is an upper bound of the coefficient of the L1-norm of the initial weights ($w_j$) when the initial statistical learning technique is the Lasso technique, where the L1-norm refers to the sum of all absolute values of the initial weights.

In some aspects, the techniques described herein relate to a method, where the hyperparameter is an upper bound of the coefficient of the to both the L1-norm sum of the initial weights ($w_j$) and the L2-norm sum of the initial weights ($w_j$) when the initial statistical learning technique is the Elastic Net technique, where the L1-norm refers to the sum of all absolute values of the initial weights, and L2-norm refers to the square root of the sum of all squared values of the initial weights.

In some aspects, the techniques described herein relate to a method, where the statistical criteria is based on an occurrence frequency of the significant weights.

In some aspects, the techniques described herein relate to a method, where for each feature, a unitary occurrence frequency is calculated for each hyperparameter value and is equal to a number of the significant weights related to the feature for the successive bootstrap repetitions divided by the number bootstrap repetitions.

In some aspects, the techniques described herein relate to a method, where the occurrence frequency is equal to the highest unitary occurrence frequency among the unitary occurrence frequencies calculated for the plurality of hyperparameter values.

In some aspects, the techniques described herein relate to a method, the statistical criteria is that each feature is selected when its occurrence frequency is greater than a frequency threshold, the frequency threshold being computed according to the occurrence frequencies obtained for the artificial features.

In some aspects, the techniques described herein relate to a method, where the number bootstrap repetitions is between 50 and 100,000.

In some aspects, the techniques described herein relate to a method, where the plurality of hyperparameter values is between 0.5 and 100 for the Lasso technique or the Elastic Net technique.

In some aspects, the techniques described herein relate to a method, where during the machine learning, the weights ($\beta_i$) of the model are further computed using a final statistical learning technique on the data associated to the set of selected features.

In some aspects, the techniques described herein relate to a method, where the final statistical learning technique is selected from a regression technique and a classification technique.

In some aspects, the techniques described herein relate to a method, where the final statistical learning technique is selected from a sparse technique and a non-sparse technique.

In some aspects, the techniques described herein relate to a method, where the sparse technique is selected from a Lasso technique and an Elastic Net technique.

In some aspects, the techniques described herein relate to a method, where during a usage phase subsequent to the machine learning, the surgical risk score is computed according to the measured values of the individual for the set of selected features.

In some aspects, the techniques described herein relate to a method, where the surgical risk score is a probability calculated according to a weighted sum of the measured values multiplied by the respective weights ($\beta_i$) for the set of selected features, when the final statistical learning technique is the classification technique.

In some aspects, the techniques described herein relate to a method, where the surgical risk score is calculated according to the following equation:

$$P = \frac{\text{Odd}}{1 + \text{Odd}}$$

where P represents the surgical risk score, and Odd is a term depending on the weighted sum.

In some aspects, the techniques described herein relate to a method, where Odd is an exponential of the weighted sum.

In some aspects, the techniques described herein relate to a method, where the surgical risk score is a term depending on a weighted sum of the measured values multiplied by the respective weights ($\beta_i$) for the set of selected features, when the final statistical learning technique is the regression technique.

In some aspects, the techniques described herein relate to a method, where the surgical risk score is equal to an exponential of the weighted sum.

In some aspects, the techniques described herein relate to a method, where during the machine learning, the method further includes, before obtaining artificial features: generating additional values of the plurality of non-artificial features based on the obtained values and using a data augmentation technique; the artificial features being then obtained according to both the obtained values and the generated additional values.

In some aspects, the techniques described herein relate to a method, where the data augmentation technique is chosen among a non-synthetic technique and a synthetic technique.

In some aspects, the techniques described herein relate to a method, where the data augmentation technique is chosen among: SMOTE technique, ADASYN technique and SVMSMOTE technique.

In some aspects, the techniques described herein relate to a method, where, for a given non-artificial feature, the less values have been obtained, the more additional values are generated.

In some aspects, the techniques described herein relate to a method, where the omic biological features are selected from one or more of cytomic features, proteomic features, transcriptomic features, and metabolomic features.

In some aspects, the techniques described herein relate to a method, where the cytomic features include single cell levels of surface and intracellular proteins in immune cell subset; and the proteomic features include circulating extracellular proteins.

In some aspects, the techniques described herein relate to a method, where the sample includes at least one sample obtained prior to surgery.

In some aspects, the techniques described herein relate to a method, where sample is obtained during the period of time from any time before surgery to the day of surgery, before a surgical incision is made.

In some aspects, the techniques described herein relate to a method, where the sample includes at least one sample obtained after surgery.

In some aspects, the techniques described herein relate to a method, where the after surgery sample is obtained approximately 24 hours after surgery.

In some aspects, the techniques described herein relate to a method, where the sample is a blood sample, a peripheral blood mononuclear cells (PBMC) fraction of a blood sample, a plasma sample, a serum sample, a urine sample, a saliva sample, or dissociated cells from a tissue sample.

In some aspects, the techniques described herein relate to a method, where the sample is contacted ex vivo with an activating agent in an effective dose and for a period of time sufficient to activate immune cells in the sample.

In some aspects, the techniques described herein relate to a method, where measuring or having measured the values includes measuring single cell levels of surface or intracellular proteins in an immune cell subset by contacting the sample with isotope-labeled or fluorescent-labeled affinity reagents specific for the surface or intracellular proteins.

In some aspects, the techniques described herein relate to a method, where the single cell levels of surface or intracellular proteins in an immune cell subset is performed by flow cytometry or mass cytometry.

In some aspects, the techniques described herein relate to a method, where measuring or having measured the values includes analyzing circulating proteins by contacting the sample with a plurality of isotope-labeled or fluorescent-labeled affinity reagents specific for extracellular proteins.

In some aspects, the techniques described herein relate to a method, where an affinity reagent is an antibody or an aptamer.

In some aspects, the techniques described herein relate to a method, where the demographic or clinical features include data selected from the group consisting of: age, sex, body mass index (BMI), functional status, emergency case, American Society of Anesthesiologists (ASA) class, steroid use for chronic condition, ascites, disseminated cancer, diabetes, hypertension, congestive heart failure, dyspnea, smoking history, history of severe COPD, dialysis, acute renal failure.

In some aspects, the techniques described herein relate to a method, where the clinical features are obtained from a patient's medical record using a machine learning algorithm.

In some aspects, the techniques described herein relate to a method, where the surgical complication is a surgical site complication (SSC).

In some aspects, the techniques described herein relate to a method, where measuring or having measured the values includes contacting the sample ex vivo with an activating agent in an effective dose and for a period of time sufficient to activate immune cells in the sample, where the activating agent is one or a combination of a TLR4 agonist (such as LPS), interleukin (IL)-2, IL-4, IL-6, IL-1β, TNFα, IFNα, PMA/ionomycin.

In some aspects, the techniques described herein relate to a method, where the period of time is from about 5 to about 240 minutes.

In some aspects, the techniques described herein relate to a method, where measuring or having measured the values includes measuring single cell levels of surface or intracellular proteins in an immune cell subset by contacting the sample with isotope-labeled or fluorescent-labeled affinity reagents specific for the surface or intracellular proteins.

In some aspects, the techniques described herein relate to a method, where immune cells are identified using single-cell surface or intracellular protein markers selected from the group consisting of CD235ab, CD61, CD45, CD66, CD7, CD19, CD45RA, CD11b, CD4, CD8, CD11c, CD123, TCRγδ, CD24, CD161, CD33, CD16, CD25, CD3, CD27, CD15, CCR2, OLMF4, HLA-DR, CD14, CD56, CRTH2, CCR2, and CXCR4.

In some aspects, the techniques described herein relate to a method, where the single-cell intracellular proteins are selected from the group consisting of phospho (p) pMAPKAPK2 (pMK2), pP38, PERK1/2, p-rpS6, pNFκB, IκB, p-CREB, pSTAT1, pSTAT5, pSTAT3, pSTAT6, cPARP, FoxP3, and Tbet.

In some aspects, the techniques described herein relate to a method, where the intracellular protein levels are measured in immune cell subsets selected from: neutrophils, granulocytes, basophils, CXCR4+neutrophils, OLMF4+neutrophils, CD14+CD16− classical monocytes (cMC), CD14−CD16+ nonclassical monocytes (ncMC), CD14+CD16+ intermediate monocytes (iMC), HLADR+CD11c+ myeloid dendritic cells (mDC), HLADR+CD123+ plasmacytoid dendritic cells (pDC), CD14+HLADR−CD11b+ monocytic myeloid derived suppressor cells (M-MDSC), CD3+CD56+ NK-T cells, CD7+CD19−CD3− NK cells, CD7+CD56loCD16hi NK cells, CD7+CD56hiCD16lo NK cells, CD19+ B-Cells, CD19+CD38+ Plasma Cells, CD19+CD38− non-plasma B-Cells, CD4+ CD45RA+ naïve T Cells, CD4+ CD45RA− memory T cells, CD4+CD161+ Th17 cells, CD4+Tbet+ Th1 cells, CD4+CRTH2+ Th2 cells, CD3+TCRγδ+ γδT Cells, Th17 CD4+T cells, CD3+FoxP3+ CD25+ regulatory T Cells (Tregs), CD8+ CD45RA+ naïve T Cells, and CD8+ CD45RA− memory T Cells.

In some aspects, the techniques described herein relate to a method, where the patient's risk for developing a surgical site complications correlates with increased pMAPKAPK2 (pMK2) in neutrophils, increased prpS6 in mDCs, or decreased IκB in neutrophils, decreased pNFκB in CD7+CD56hiCD16lo NK cells in response to ex vivo activation of a sample collected before surgery with LPS.

In some aspects, the techniques described herein relate to a method, where the patient's risk for developing a surgical site complication correlates with increased pSTAT3 in neutrophils, mDCs, or Tregs increased prpS6 in CD56hiCD16lo NK cells or mDCs, increase pSTAT5 in mDCs, or pDCs, or decreased IκB in CD4+Tbet+ Th1 cells, decreased pSTAT1 in pDCs, in response to ex vivo activation of a sample collected before surgery with IL-2, IL-4, and/or IL-6.

In some aspects, the techniques described herein relate to a method, where the patient's risk for developing a surgical site complication correlates with increased prpS6 in neutrophils or mDCs, increased PERK in M-MDSCs or ncMCs, increased pCREB in γδT Cells or decrease IκB, pP38 or pERK in neutrophils or decreased pCREB or pMAPKAPK2 in CD4+Tbet+ Th1 cells or decreased pERK in CD4+ CRTH2+ Th2 cells, in response to ex vivo activation of a sample collected before surgery with TNFα.

In some aspects, the techniques described herein relate to a method, where the patient's risk for developing a surgical site complication correlates with increased pSTAT3 in neutrophils, M-MDSCs, cMCs, or ncMCs, increased pSTAT5 in Tregs or CD45RA− memory CD4+T cells, increased pMAPKAPK2 in mDCs, pCREB or IκB in CD4+Tbet+ Th1 cells, increased pSTAT6 in NKT cells, or decreased pERK in CD4+Tbet+ Th1 cells in unstimulated samples collected before and/or after surgery.

In some aspects, the techniques described herein relate to a method, where the patient's risk for developing a surgical site complication correlates with increased M-MDSC, G-MDSC, ncMC, Th17 cells, or decreased CD4+CRTH2+ Th2 cell frequencies collected before and/or after surgery.

In some aspects, the techniques described herein relate to a method, where the patient's risk for developing a surgical site complication correlates with increased IL-1β, ALK, WWOX, HSPH1, IRF6, CTNNA3, CCL3, sTREM1, ITM2A, TGFα, LIF, ADA, or decreased ITGB3, EIF5A, KRT19, NTproBNP collected before and/or after surgery.

In some aspects, the techniques described herein relate to a system including a processor and memory containing instructions, which when executed by the processor, direct the processor to perform any of the foregoing methods.

In some aspects, the techniques described herein relate to a non-transitory machine readable medium containing instructions that when executed by a computer processor direct the processor to perform any of the foregoing methods.

In some aspects, the techniques described herein relate to a method, further including treating the individual before surgery is made in accordance with the assessment of an individual's risk for developing a surgical site complication.

In some aspects, the techniques described herein relate to a method, further including treating the individual after surgery is made in accordance with the assessment of an individual's risk for developing a surgical site complication.

Other features and advantages of the present invention will become apparent from the following detailed description, taken in conjunction with the accompanying drawings which illustrate, by way of example, the principles of the invention.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 3A-3B illustrate exemplary pseudo-code for MOB algorithms in accordance with various embodiments.

FIGS. 9A-9G illustrate single cell immune response features, and FIGS. 9H-9N illustrate plasma proteomic features.

DETAILED DESCRIPTION

Figure 1:
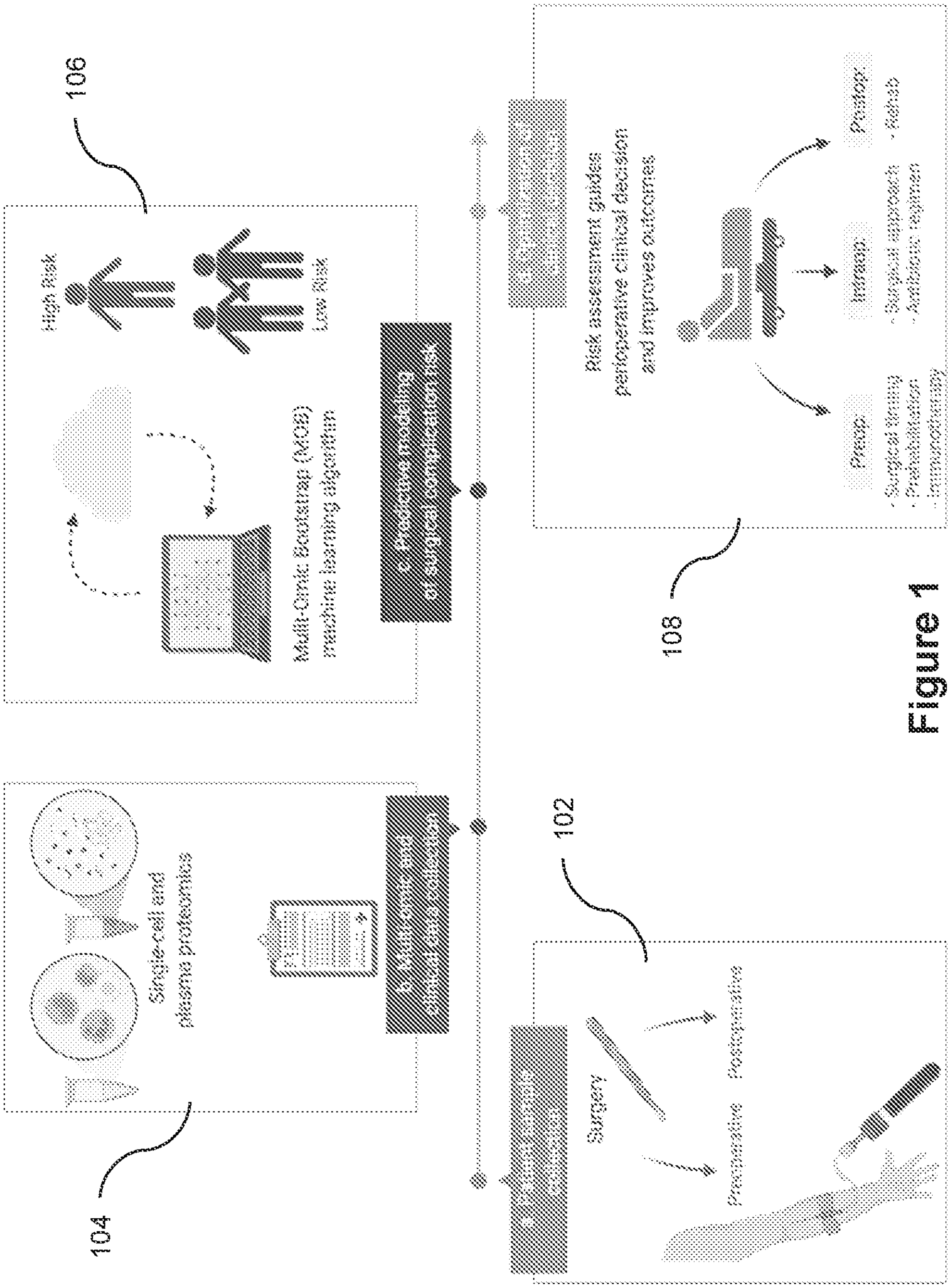
FIG. 1 illustrates an exemplary method for the prediction of a patient's clinical outcome after surgery using a machine learning algorithm that integrates multi-omic biological (e.g. single cell immune responses and plasma proteomic data) and clinical data in accordance with various embodiments. Various embodiments provide for a method of guiding a surgeon or healthcare provider's clinical decision using a Multi-Omic Bootstrap (MOB) machine learning algorithm to generate a predictive model for the probability for a patient to develop Surgical Site Complications (SSCs).

As noted previously, Existing risk prediction tools are based on clinical parameters and are insufficient to estimate an individual patient's risk for SSCs. (See e.g., Eamer G, et al.; cited above.). Thus, integration of biological parameters echoing mechanisms that drive the pathogenesis of SSCs is a highly plausible approach to increase risk prediction accuracy.

Surgery is associated with significant tissue trauma, triggering a programmed inflammatory response that engages the innate and adaptive branches of the immune system. Within hours of surgical incision, a highly diverse network of innate immune cells (including monocytes, neutrophils and their subsets) is activated in response to circulating DAMPs (damage-associated molecular patterns) and inflammatory cytokines (e.g., HMGB1, TNFα, and IL-1β). Following the early innate immune response to surgery, a compensatory, anti-inflammatory adaptive immune response has been traditionally described. However, recent transcriptomic and mass cytometry analysis suggest that adaptive immune responses are mobilized jointly with innate immune responses and coincide with the activation of specialized immunosuppressive immune cell subsets, such as myeloid-derived suppressor cells (MDSCs). In the context of uncomplicated surgical recovery, innate and adaptive responses synergize to orchestrate pro- and anti-inflammatory (pro-resolving) processes required for pathogen defense tissue remodeling and the resolution of pain and inflammation after injury. (See e.g., Stoecklein V M et al. *J Leukoc Biol* 2012; Gaudilliere B et al. *Sci Transl Med* 2014; 6(255):255ra131; the disclosure of which is hereby incorporated by reference herein in its entirety.)

Complications including infections, wound dehiscence, and eventually end-organ damage arise as pro-inflammatory and immune-suppressive responses tilt out of balance. A detailed characterization of immunological mechanisms that differ between patients with and without surgical complications is thus a highly promising approach for identifying pre- and post-operative biological events that contribute to and precede surgical complications. Prior attempts to detect biological markers predicting the risk for SSCs focused on secreted humoral factors, surface marker expression on select immune cells or transcriptional analysis of pooled circulating leukocytes. However, detected associations were insufficient to accurately predict the risk of SSCs for individual patients.

A major impediment has been the lack of high-content, functional assays that can characterize the complex, multicellular inflammatory response to surgery with single-cell resolution. In addition, analytical tools that can integrate the single-cell immunological data with other 'omics and clinical data to predict the development of SSC are lacking. Thus, there is a need for improved measures for the diagnosis, prognosis, treatment, management, and therapeutic development of SSC after surgery.

High-throughput omics assays including metabolomics, proteomic and cytometric immunoassay data can potentially capture complex mechanism of diseases and biological processes by providing thousands of measurements systematically obtained on each biological sample.

The analysis of mass cytometry immunoassay as well as other omics assays typically has two related goals analyzed by dichotomous approaches. The first goal is to predict the outcome of interest and identify biomarkers that are the best set of predictors of the considered outcome; the second goal is to identify potential pathways implicated in the disease offering better understanding into the underlying biology. The first goal is addressed by deploying machine learning methods and fitting a prediction model that selects typically a handful of most informative biomarkers among thousands of measurements. The second goal is usually addressed by performing univariate analysis of each measurement to determine the significance of that measurement with respect to the outcome by evaluating its p-value that is then adjusted for multiple hypothesis testing.

In the context of machine learning, omics data-characterized by a high number of features p and a much smaller number of samples n-fall in the scenario for which p»n. The gold-standard machine learning methodology for this scenario consists of the usage of regularized regression or classification methods, and specifically sparse linear models, such as the Lasso; (See e.g., Tibshirani, Robert. "Regression shrinkage and selection via the lasso." Journal of the Royal Statistical Society: Series B (Methodological) 58.1 (1996): 267-288; the disclosure of which is hereby incorporated by reference herein in its entirety;) and Elastic Net. (See e.g., Zou, Hui, and Trevor Hastie. "Regularization and variable selection via the elastic net." Journal of the royal statistical society: series B (statistical methodology) 67.2 (2005): 301-320; the disclosure of which is hereby incorporated by reference herein in its entirety.) Consider for instance the following linear model, given by: $Y=X\beta+\epsilon X=(X_1, \ldots, X_n)\in \mathbb{R}^{n\times p}Y=(Y_1, \ldots, Y_n)\in \mathbb{R}^{n}\epsilon=(\epsilon_1, \ldots, \epsilon_n)\in \mathbb{R}^{n}\beta=(\beta_1, \ldots, \beta_p)\in \mathbb{R}^{p}\beta\beta S=\{\beta_k, \beta_k\neq 0\}\beta$ where and are respectively the input and the response variables; is the random noise with independent, identically distributed components. are the coefficients associated to each feature, that we need to learn. Sparse linear models add a regularization of the model coefficients, which allows for balancing the bias-variance tradeoff and prevents overfitting of models. The Lasso and the Elastic Net use L1-regularization in the model, inducing sparsity in the fit of the coefficients. In the optimal fit of such models, we end up determining a subset where many of the coefficients become zeros, resulting in only a subset of features playing a role in the model.

$$
\begin{aligned}
X &= (X_1, \ldots X_n) \in \mathbb{R}^{n\times p} Y \\
&= (Y_1, \ldots Y_n) \in \mathbb{R}^{n} \epsilon \\
&= (\epsilon_1, \ldots \epsilon_n) \in \mathbb{R}^{n} \beta \\
&= (\beta_1, \ldots \beta_p) \in \mathbb{R}^{p} \beta\beta S \\
&= \{\beta_k, \beta_k \neq 0\} \beta
\end{aligned}
$$

Instability is an inherent problem in feature selection of machine learning model. Since the learning phase of the model is performed on a finite data sample, any perturbation in data may yield a somewhat different set of selected variables. In settings where the performance is evaluated via cross-validation, this implies that the Lasso yields a somewhat different set of chosen biomarkers making any biological interpretation of the result impossible. Consistent feature selection in Lasso is challenging as it is achieved only under restrictive conditions. Most sparse techniques such as the Lasso cannot provide a quantification of how far the chosen model is from the correct one, nor quantify the variability of chosen features.

Another major limitation of existing methods is the difficulty to integrate different sources of biological information. Most machine learning algorithms use input data agnostically in the learning process of the models. The main challenge lies in the integration of multiple sources of data with their differences in modalities, size and signal-to-noise ratio in the learning process. In the learning process, current approach are typically limited with biased assessment of the contribution of individual sources of data when juxtaposed as a unique dataset. Finally, it is key to use identified informative features from different layers together to optimize the predictive power of such algorithms. Most methods, when ensembling different results from individual data sources also lack the capacity to assess individual interactions between features that are key to model biological mechanisms at play.

Turning now to the drawings, systems and methods to generate a surgical risk score and uses thereof are provided. In many embodiments, compositions and methods are provided for the prediction, classification, diagnosis, and/or theranosis, of a clinical outcome following surgery in a subject based on the integration of multi-omic biological and clinical data using a machine learning model (e.g., FIG. 1). Many embodiments provide methods to generate a predictive model of a patient's probability to develop a surgical site complication (SSC). In many embodiments the predictive model is obtained by quantitating specific biological and clinical features, before or after surgery. Various embodiments use at least one omic (including, but not limited to, genomic, cytomic, proteomic, transcriptomic, metabolomic) feature in combination with the clinical data to generate the predictive model. Various embodiments utilize a machine learning model to integrate the various clinical and/or cytomic, proteomic, transcriptomic, or metabolomic features to generate a predictive model. In some embodiments, the clinical outcome is the development of SSCs (including surgical site infection, wound dehiscence, abscess, or fistula formation). A predictive model in accordance with many embodiments can indicate a patient's risk for developing a SSC.

Once a classification or prognosis has been made, it can be provided to a patient or caregiver. The classification can provide prognostic information to guide the healthcare provider's or surgeon's clinical decision-making, such as delaying or adjusting the timing of surgery, adjusting the surgical approach, adjusting the type and timing of antibiotic and immune-modulatory regimens, personalizing or adjusting prehabilitation health optimization programs, planning for longer time in the hospital before or after surgery or planning for spending time in a managed care facility, and the like. Appropriate care can reduce the rate of SSCs, length of hospital stays, and/or the rate of readmission for patients following surgery.

As illustrated in FIG. 1, various embodiments are directed to methods of predicting a clinical outcome for an individual undergoing surgery (e.g., patient). Many embodiments collect a patient sample at 102. Such samples can be collected at any time before surgery or after surgery. In some embodiments the sample is collected up to a week (7 days) before or after surgery. In certain embodiments, the sample is collected 1 day, 2 days, 3 days, 4 days, 5 days, 6 days, or 7 days before surgery, while some embodiments collect a sample 1 day, 2 days, 3 days, 4 days, 5 days, 6 days, or 7 days after surgery. Additional embodiments collect a sample day of surgery, including before and/or after surgery, including immediately before and/or after surgery. Certain embodiments collect multiple samples before, after, or before and after surgery, anesthesia, and/or any other procedural step included within a particular surgical or operational protocol.

At 104, many embodiments obtain omic data (e.g., proteomic, cytomic, and/or any other omic data) from the sample. Certain embodiments combine multiple omic data—e.g., plasma proteomics (e.g., analysis of plasma protein expression levels) and single-cell cytomics (e.g., single-cell analysis of circulating immune cell frequency and signaling activities)—as multi-omic data. Certain embodiments obtain clinical data for the individual. Clinical data in accordance with various embodiments includes one or more of medical history, age, weight, body mass index (BMI), sex/gender, current medications/supplements, functional status, emergency case, steroid use for chronic condition, ascites, disseminated cancer, diabetes, hypertension, congestive heart failure, dyspnea, smoking history, history of severe Chronic Obstructive Pulmonary Disease (COPD), dialysis, acute renal failure and/or any other relevant clinical data. Clinical data can also be derived from clinical risk scores such as the American Society of Anesthesiologist (ASA) or the American College of Surgeon (ACS) risk score.

Additional embodiments generate a predictive model of a surgical complications, such as SSCs, at 106. Many embodiments utilize a machine learning model, such as described herein. Various embodiments operate in a pipelined manner, such that as data, obtained or collected, are immediately sent to a machine learning model to generate an integrated surgical risk score. Some embodiments house the machine learning model locally, such that the integrated risk score is generated without network communication, while some embodiments operate the machine learning model on a server or other remote device, such that clinical data and multi-omics data are transmitted via a network, and the integrated surgical risk score is returned to a medical professional/practitioner at their local institution, clinic, hospital, and/or other medical facility.

At 108, further embodiments adjust the treatment of the individual based on the integrated surgical risk score. In various embodiments, the adjustment can include delaying surgery (e.g., until an improved integrated surgical risk score is obtained), prescribing additional antibiotics to prevent infection, and/or adjusting surgical procedures to compensate for increased risk as identified by the integrated surgical risk score. With this approach, therapeutic regimens can be individualized and tailored according to predicted probability for a patient to develop an SSC, thereby providing a regimen that is individually appropriate.

It should be noted that the embodiment illustrated in FIG. 1 is illustrative of various steps, features, and details that can be implemented in various embodiments and is not intended to be exhaustive or limiting on all embodiments. Additionally, various embodiments may include additional steps, which are not described herein and/or fewer steps (e.g., omit certain steps) than illustrated and described. Various embodiments may also repeat certain steps, where additional data, prediction, or procedures can be updated for an individual, such as repeating generating a predictive model 106, to identify whether a risk score or SSC is more or less likely to develop in the individual. Further embodiments may also obtain samples or clinical data from a third party from a collaborating, subordinate, or other individual and/or obtaining a sample that has been stored or previously collected or obtained. Certain embodiments may even perform certain actions or features in a different order than illustrated or described and/or perform some actions or features simultaneously, relatively simultaneously (e.g., one action may begin or commence before another action has finished or completed).

Definitions

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control.

All publications, patents, and patent applications mentioned in this specification are herein incorporated by reference to the same extent as if each individual publication, patent, or patent application was specifically and individually indicated to be incorporated by reference.

It must be noted that, as used in the specification and the appended claims, the singular forms "a," "an," and "the" include plural referents unless the context clearly dictates otherwise.

The terms "subject," "individual," and "patient" are used interchangeably herein to refer to a vertebrate, preferably a mammal, more preferably a human. Mammalian species that provide samples for analysis include canines; felines; equines; bovines; ovines; etc. and primates, particularly humans. Animal models, particularly small mammals, e.g. murine, lagomorpha, etc. can be used for experimental investigations. The methods of the invention can be applied for veterinary purposes. The terms "biomarker," "biomarkers," "marker", "features", or "markers" for the purposes of the invention refer to, without limitation, proteins together with their related metabolites, mutations, variants, polymorphisms, phosphorylation, modifications, fragments, subunits, degradation products, elements, and other analytes or sample-derived measures. Markers can include expression levels of an intracellular protein or extracellular protein. Markers can also include combinations of any one or more of the foregoing measurements, including temporal trends and differences. Broadly used, a marker can also refer to an immune cell subset.

As use herein, the term "omic" or "-omic" data refers to data generated to quantify pools of biological molecules, or processes that translate into the structure, function, and dynamics of an organism or organisms. Examples of omic data include (but are not limited to) genomic, transcriptomic, proteomic, metabolomic, cytomic data, among others.

As use herein the term "cytomic" data refers to an omic data generated using a technology or analytical platform that allows quantifying biological molecules or processes at the single-cell level. Examples of cytomic data include (but are not limited to) data generated using flow cytometry, mass cytometry, single-cell RNA sequencing, cell imaging technologies, among others.

The term "inflammatory" response is the development of a humoral (antibody mediated) and/or a cellular response, which cellular response may be mediated by innate immune cells (such as neutrophils or monocytes) or by antigen-specific T cells or their secretion products. An "immunogen" is capable of inducing an immunological response against itself on administration to a mammal or due to autoimmune disease.

To "analyze" includes determining a set of values associated with a sample by measurement of a marker (such as, e.g., presence or absence of a marker or constituent expression levels) in the sample and comparing the measurement against measurement in a sample or set of samples from the same subject or other control subject(s). The markers of the present teachings can be analyzed by any of various conventional methods known in the art. To "analyze" can include performing a statistical analysis, e.g. normalization of data, determination of statistical significance, determination of statistical correlations, clustering algorithms, and the like.

A "sample" in the context of the present teachings refers to any biological sample that is isolated from a subject, generally a blood or plasma sample, which may comprise circulating immune cells. A sample can include, without limitation, an aliquot of body fluid, plasma, serum, whole blood, PBMC (white blood cells or leucocytes), tissue biopsies, dissociated cells from a tissue sample, a urine sample, a saliva sample, synovial fluid, lymphatic fluid, ascites fluid, and interstitial or extracellular fluid. "Blood sample" can refer to whole blood or a fraction thereof, including blood cells, plasma, serum, white blood cells or leucocytes. Samples can be obtained from a subject by means including but not limited to venipuncture, biopsy, needle aspirate, lavage, scraping, surgical incision, or intervention or other means known in the art.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored. Similarly, the term "obtaining a dataset associated with a sample" encompasses obtaining a set of data determined from at least one sample. Obtaining a dataset encompasses obtaining a sample, and processing the sample to experimentally determine the data, e.g., via measuring antibody binding, or other methods of quantitating a signaling response. The phrase also encompasses receiving a set of data, e.g., from a third party that has processed the sample to experimentally determine the dataset.

"Measuring" or "measurement" in the context of the present teachings refers to determining the presence, absence, quantity, amount, or effective amount of a substance in a clinical or subject-derived sample, including the presence, absence, or concentration levels of such substances, and/or evaluating the values or categorization of a subject's clinical parameters based on a control, e.g. baseline levels of the marker.

Classification can be made according to predictive modeling methods that set a threshold for determining the probability that a sample belongs to a given class. The probability preferably is at least 50%, or at least 60% or at least 70% or at least 80% or higher. Classifications also can be made by determining whether a comparison between an obtained dataset and a reference dataset yields a statistically significant difference. If so, then the sample from which the dataset was obtained is classified as not belonging to the reference dataset class. Conversely, if such a comparison is not statistically significantly different from the reference dataset, then the sample from which the dataset was obtained is classified as belonging to the reference dataset class.

The predictive ability of a model can be evaluated according to its ability to provide a quality metric, e.g. Area Under the Curve (AUC) or accuracy, of a particular value, or range of values. In some embodiments, a desired quality threshold is a predictive model that will classify a sample with an accuracy of at least about 0.7, at least about 0.75, at least about 0.8, at least about 0.85, at least about 0.9, at least about 0.95, or higher. As an alternative measure, a desired quality threshold can refer to a predictive model that will classify a sample with an AUC of at least about 0.7, at least about 0.75, at least about 0.8, at least about 0.85, at least about 0.9, or higher.

As is known in the art, the relative sensitivity and specificity of a predictive model can be "tuned" to favor either the selectivity metric or the sensitivity metric, where the two metrics have an inverse relationship. The limits in a model as described above can be adjusted to provide a selected sensitivity or specificity level, depending on the particular requirements of the test being performed. One or both of sensitivity and specificity can be at least about at least about 0.7, at least about 0.75, at least about 0.8, at least about 0.85, at least about 0.9, or higher.

As used herein, the term "theranosis" refers to the use of results obtained from a prognostic or diagnostic method to direct the selection of, maintenance of, or changes to a therapeutic regimen, including but not limited to the choice of one or more therapeutic agents, changes in dose level, changes in dose schedule, changes in mode of administration, and changes in formulation. Diagnostic methods used to inform a theranosis can include any that provides information on the state of a disease, condition, or symptom.

The terms "therapeutic agent", "therapeutic capable agent" or "treatment agent" are used interchangeably and refer to a molecule, compound or any non-pharmacological regimen that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular agent chosen, the dosing regimen to be followed, whether it is administered in combination with other compounds, timing of administration, the tissue to be imaged, and the physical delivery system in which it is carried.

"Suitable conditions" shall have a meaning dependent on the context in which this term is used. That is, when used in connection with an antibody, the term shall mean conditions that permit an antibody to bind to its corresponding antigen. When used in connection with contacting an agent to a cell, this term shall mean conditions that permit an agent capable of doing so to enter a cell and perform its intended function. In one embodiment, the term "suitable conditions" as used herein means physiological conditions.

The term "antibody" includes full length antibodies and antibody fragments, and can refer to a natural antibody from any organism, an engineered antibody, or an antibody generated recombinantly for experimental, therapeutic, or other purposes as further defined below. Examples of antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, agonists, neutralizing, inhibitory, or stimulatory. They can be humanized, glycosylated, bound to solid supports, and possess other variations.

Machine Learning Methods for Predicting Surgical Outcomes

To obtain a predictive model of a clinical outcome after surgery, many embodiments employ a machine learning method that integrates the single-cell analysis of immune cell responses using mass cytometry with the multiplex assessment of inflammatory plasma proteins in blood samples collected from patients before or after surgery. Many embodiments employ the Multi-Omic Bootstrap (MOB) machine learning method to predict the development of SSCs after surgery. MOB, in accordance with various embodiments integrates one or more omic data categories (e.g., categories described herein) by extracting the most robust features from each data layer before combining these features and ensures stability of the features selected during statistical modeling of omic datasets.

The development of the stability selection method (See e.g., Nicolai Meinshausen. Peter Bühlmann. Ann. Statist. 34 (3) 1436-1462 June 2006; the disclosure of which is hereby incorporated by reference herein in its entirety) is a key element in the development of the MOB algorithm. While the problem of variability is inherent and cannot be completely overcome, the stability selection can characterize this variation by considering the frequency at which each feature is chosen when multiple Lasso models are obtained on subsampled data. The selection frequency offers a quantitative measure into the importance of each feature that is readily interpretable from the biological standpoint. It has been shown that stability selection requires much weaker assumptions for asymptotically consistent variable selection compared to Lasso. Stated differently, stability selection, instead of selecting one model, subsamples data repeatedly and selects stable variables, that is, variables that occur in a large fraction of the resulting models. The chosen stable variables are defined by having selection frequency above a chosen threshold:

$$\hat{S}_{stable} = \left\{\beta_k : \max_{\lambda\in\Lambda} \prod\nolimits_k^\lambda > \pi_{th}\right\}$$

where $$\prod\nolimits_k^\lambda$$

is the selection frequency of feature k for the regularization parameter λ.

One of the difficulties of the previous method is that it is difficult to assess noise. As the goal is to discriminate noisy variables from predictive ones, the use of negative control features is an appropriate approach to develop internal noise filter in the learning process. Negative control features designate synthetically made noisy features. One of the major contributions of this work is that, if built properly, it will be possible to adapt the thresholds previously mentioned from the distribution of the artificial features in the stability selection process. Two ways to generate these artificial features have been considered. Both techniques extend the initial input, ending up with an input matrix $(X,\tilde{X})\in \mathbb{R}^{n\times 2p}$, where $\tilde{X}$ is the matrix of synthetic negative controls. The first technique called 'decoy' relies on a stochastic construction. Each synthetic feature is built by random permutation of its original counterpart (the permutation is independent for each synthetic feature). This process is done before each subsampling of the data. It is then possible to define a threshold from the behavior of the decoy feature in the stability selection, for instance:

$$\pi_{th} = c \times \text{mean} \max_{\lambda\in\Lambda} \prod\nolimits_{k+p}^{\lambda}$$

Where c is a ratio set by the user and mean $$\max_{\lambda\in\Lambda} \prod\nolimits_{k+p}^{\lambda}$$

is the mean of the maximum of selection frequency of the decoy features. The other technique uses model-X knockoffs (See e.g., Candes, Emmanuel, et al. "Panning for gold: 'model-X'knockoffs for high dimensional controlled variable selection." Journal of the Royal Statistical Society: Series B (Statistical Methodology) 80.3 (2018): 551-577; the disclosure of which is hereby incorporated by reference herein in its entirety;) to build the synthetic negative controls. The construction allows to replicate the distribution of the original data (notably, the knockoffs correlation mimics the original one) and guarantees that the distribution of $\tilde{X}$ is orthogonal to the distribution of Y knowing X ($\tilde{X}\perp Y|X$). It is then possible to compare each pair of true/knockoffs variables after performing the stability selection and to select the feature k if:

$$\left(\max_{\lambda\in\Lambda} \prod\nolimits_{k}^{\lambda} - \max_{\lambda\in\Lambda} \prod\nolimits_{k+p}^{\lambda}\right) > cst$$

Where $$\prod\nolimits_{k}^{\lambda}$$

and $$\prod\nolimits_{k+p}^{\lambda}$$

are the selection frequency of the feature k and its knockoff counterpart, and cst is a positive constant defined by the user.

The machine learning model is typically trained, using among other step a bootstrap procedure on a plurality of individual data layers. Each data layer represents one type of data from the plurality of possible features and at least one artificial feature. Each feature is for example chosen among a group consisting of: genomic, transcriptomic, proteomic, cytomic, metabolomic, clinical and demographic data.

Each data layer comprises data for a population of individuals, and each feature includes feature values for all individuals in the population of individuals. During machine learning, for each data layer, the obtained feature values for the population of individuals are typically arranged in a matrix X with n rows and p columns, where each row corresponds to a respective individual and each column corresponds to a respective feature. In other words, the matrix X is a concatenation of p vectors, each one being related to a respective feature and containing n feature values, with typically one feature value for each individual.

For a respective data layer, each artificial feature is obtained from a non-artificial feature among the plurality of features, via a mathematical operation performed on the feature values of the non-artificial feature. The mathematical operation is for example chosen among the group consisting of: a permutation, a sampling, a combination, a knockoff method and an inference. The permutation is for instance a total permutation without replacement of the feature values. The sampling is typically a sampling with replacement of some of the feature values or a sampling without replacement of the feature values. The combination is for instance a linear combination of the feature values. The knockoff method is for instance a Model-X knockoff applied to the feature values. The inference is typically a fit of a statistical distribution of the feature values, such as a Gaussian distribution, an exponential distribution, an uniform distribution or a Poisson distribution; and then inference sampling at random from it. The obtaining of artificial features is also called spike of artificial features, and corresponds to instruction 2 in the pseudo-codes of the FIGS. 3A and 3B.

The model includes weights $\beta_i$ for a set of selected biological and clinical or demographic features, such weights $\beta_i$ being typically derived from initial weights $w_j$ repeatedly modified during the machine learning of the model.

During the machine learning and for each data layer, for every repetition of the bootstrap, the initial weights $w_j$ are computed for the plurality of features and the at least one artificial feature associated with that data layer, by using an initial statistical learning technique. The generation of the bootstrap samples, and respectively the estimation of the initial weights $w_j$, also called coefficients, correspond to instruction 4, and respectively instruction 5, in the pseudo-codes of the FIGS. 3A and 3B.

The initial statistical learning technique is typically a sparse technique or a non-sparse technique. The initial statistical learning technique is for example a regression technique or a classification technique. Accordingly, the initial statistical learning technique is preferably chosen from among the group consisting of: a sparse regression technique, a sparse classification technique, a non-sparse regression technique and a non-sparse classification technique.

As an example, the initial statistical learning technique is therefore chosen from among the group consisting of: a linear or logistic linear regression technique with L1 or L2 regularization, such as the Lasso technique or the Elastic Net technique; (see e.g., Tibshirani and Zou and Hastie; cited above;) a model adapting linear or logistic linear regression techniques with L1 or L2 regularization, such as the Bolasso technique (see e.g., Bach, Francis R. "Bolasso: model consistent lasso estimation through the bootstrap." Proceedings of the 25th international conference on Machine learning. 2008; the disclosure of which is hereby incorporated by reference herein in its entirety), the relaxed Lasso (see e.g., Meinshausen, Nicolai. "Relaxed lasso." Computational Statistics & Data Analysis 52.1 (2007): 374-393; the disclosure of which is hereby incorporated by reference herein in its entirety;) the random-Lasso technique (see e.g., Wang, Sijian, et al. "Random lasso." The annals of applied statistics 5.1 (2011): 468; the disclosure of which is hereby incorporated by reference herein in its entirety;) the grouped-Lasso technique (see e.g., Friedman, Jerome, Trevor Hastie, and Robert Tibshirani. Applications of the lasso and grouped lasso to the estimation of sparse graphical models. Technical report, Stanford University, 2010; the disclosure of which is hereby incorporated by reference herein in its entirety;) the LARS technique (see e.g., Eyraud, Remi, Colin De La Higuera, and Jean-Christophe Janodet. "LARS: A learning algorithm for rewriting systems." Machine Learning 66.1 (2007): 7-31; the disclosure of which is hereby incorporated by reference herein in its entirety;) a linear or logistic linear regression technique without L1 or L2 regularization; a non-linear regression or classification technique with L1 or L2 regularization; a Decision Tree technique; a Random Forest technique; a Support Vector Machine technique, also called SVM technique; a Neural Network technique; and a Kernel Smoothing technique.

Then, at least one selected feature is determined for each data layer, based on a statistical criteria depending on the computed initial weights $w_j$. The statistical criteria depends on significant weights among the computed initial weights $w_j$. The significant weights are for example non-zero weights, when the initial statistical learning technique is a sparse regression technique, or weights above a predefined weight threshold, when the initial statistical learning technique is a non-sparse regression technique. The determination of the significant weights corresponds to instruction 6 in the pseudo-codes of the FIGS. 3A and 3B.

As an example, the significant weights are non-zero weights, when the initial statistical learning technique is chosen from among the group consisting of: a linear or logistic linear regression technique with L1 or L2 regularization, such as the Lasso technique or the Elastic Net technique; a model adapting linear or logistic linear regression techniques with L1 or L2 regularization, such as the Bolasso technique, the relaxed Lasso, the random-Lasso technique, the grouped-Lasso technique, the LARS technique; a non-linear regression or classification technique with L1 or L2 regularization; and a Kernel Smoothing technique.

"Non-zero weight" refers to a weight which is in absolute value greater than a predefined very low threshold, such as $10^{-5}$, also noted 1e-5. Accordingly, "Non-zero weight" typically refers to a weight greater than $10^{-5}$ in absolute value.

Alternatively, the significant weights are weights above the predefined weight threshold, when the initial statistical learning technique is chosen from among the group consisting of: a linear or logistic linear regression technique without L1 or L2 regularization; a Decision Tree technique; a Random Forest technique; a Support Vector Machine technique; and a Neural Network technique. In the example of the Neural Network technique, the significant weights are weights above the predefined weight threshold on an initial layer of the corresponding neural network.

The skilled person will observe that the Support Vector Machine technique is considered as a sparse technique with support vectors, and the technique leads to only keeping the support vectors. The skilled person will also note that for the Decision Tree technique, the aforementioned weight corresponds to the feature importance, and accordingly that the significant weights are the features for which the split in the decision tree induces a certain decrease in impurity.

Optionally, the initial weights $w_j$ are further computed for a plurality of values of a hyperparameter $\lambda$, the hyperparameter $\lambda$ being a parameter whose value is used to control the learning process. The hyperparameter $\lambda$ is typically a regularization coefficient used according to a respective mathematical norm in the context of a sparse initial technique. The mathematical norm is for example a P-norm, with P being an integer.

As an example, the hyperparameter $\lambda$ is an upper bound of the coefficient of the L1-norm of the initial weights $w_j$ when the initial statistical learning technique is the Lasso technique, where the L1-norm refers to the sum of all absolute values of the initial weights.

As another example, the hyperparameter $\lambda$ is an upper bound of the coefficient of the both the L1-norm sum of the initial weights $w_j$ and the L2-norm sum of the initial weights $w_j$ when the initial statistical learning technique is the Elastic Net technique, where the L1-norm is defined above and the L2-norm refers to the square root of the sum of all squared values of the initial weights.

For the feature selection, the statistical criteria depends for example on an occurrence frequency of the significant weights. As an example, the statistical criteria is that each feature is selected when its occurrence frequency is greater than a frequency threshold.

For each feature, to determine the occurrence frequency, a unitary occurrence frequency is calculated for each value of the hyperparameter $\lambda$, the unitary occurrence frequency being equal to a number of the significant weights related to said feature for the successive bootstrap repetitions divided by the number bootstrap repetitions used for said feature. The occurrence frequency is then typically equal to the highest unitary occurrence frequency among the unitary occurrence frequencies calculated for all the values of the hyperparameter $\lambda$. The determination of each feature's occurrence frequency, also called selection frequency, corresponds to instructions 8 and 10 in the pseudo-codes of the FIGS. 3A and 3B.

The frequency threshold is typically computed according to the occurrence frequencies obtained for the artificial features. This frequency threshold is for example 2 standard deviations over the mean or the median of the occurrence frequencies obtained for the artificial features. Alternatively, the frequency threshold is 3 times the mean of the occurrence frequencies obtained for the artificial features. Still alternatively, the frequency threshold is equal to the maximum between one of the aforementioned examples of the calculated frequency threshold and a predefined frequency threshold. The computation of the frequency threshold corresponds to instruction 11 in the pseudo-codes of the FIGS. 3A and 3B.

Lastly, the feature selection is operated for each layer based on the statistical criteria. For example, the selected feature(s) are the one(s) which have their occurrence frequency greater than the frequency threshold. The feature selection corresponds to instruction 12 in the pseudo-codes of the FIGS. 3A and 3B.

As an example, each value of the hyperparameter $\lambda$ is chosen according to a predefined scheme of values between the lower and upper bounds of the chosen value range for the hyperparameter $\lambda$. As a variant, the values of the hyperparameter $\lambda$ are evenly distributed between the lower and upper bounds of the chosen value range for the hyperparameter $\lambda$. The hyperparameter $\lambda$ is typically between 0.5 and 100 when the initial statistical learning technique is the Lasso technique or the Elastic Net technique.

For the bootstrapping process, the number bootstrap repetitions is typically between 50 and 100 000; preferably between 500 and 10 000; still preferably equal to 10 000.

During the machine learning, after the feature selection, the weights $\beta_i$ of the model are further computed using a final statistical learning technique on the data associated to the set of selected features.

The final statistical learning technique is typically a sparse technique or a non-sparse technique. The final statistical learning technique is for example a regression technique or a classification technique. Accordingly, the final statistical learning technique is preferably chosen from among the group consisting of: a sparse regression technique, a sparse classification technique, a non-sparse regression technique and a non-sparse classification technique.

As an example, the final statistical learning technique is therefore chosen from among the group consisting of: a linear or logistic linear regression technique with L1 or L2 regularization, such as the Lasso technique or the Elastic Net technique; a model adapting linear or logistic linear regression techniques with L1 or L2 regularization, such as the bo-Lasso technique, the soft-Lasso technique, the random-Lasso technique, the grouped-Lasso technique, the LARS technique; a linear or logistic linear regression technique without L1 or L2 regularization; a non-linear regression or classification technique with L1 or L2 regularization; a Decision Tree technique; a Random Forest technique; a Support Vector Machine technique, also called SVM technique; a Neural Network technique; and a Kernel Smoothing technique.

During a usage phase subsequent to the machine learning, the surgical risk score is computed according to the measured values of the individual for the set of selected features.

As an example, the surgical risk score is a probability calculated according to a weighted sum of the measured values multiplied by the respective weights $\beta_i$ for the set of selected features, when the final statistical learning technique is a respective classification technique.

According to this example, the surgical risk score is typically calculated with the following equation:

$$P = \frac{\text{Odd}}{1 + \text{Odd}}$$

where P represents the surgical risk score, and

Odd is a term depending on the weighted sum.

As a further example, Odd is an exponential of the weighted sum. Odd is for instance calculated according to the following equation:

$$\text{Odd} = \exp(\beta_0 + \beta_1 X_1 + \ldots + \beta_{p,stable} X_{p,stable})$$

where exp represents the exponential function, $\beta_0$ represents a predefined constant value, $\beta_i$ represents the weight associated to a respective feature in the set of selected features, $X_i$ represents the measured value of the individual associated to the respective feature, and i is an index associated to each selected feature, i being an integer between 1 and $p_{stable}$, where $p_{stable}$ is the number of selected features for the respective layer.

The skilled person will notice that in the previous equation, the weights $\beta_i$ and the measured values $X_i$ may be negative values as well as positive values.

As another example, the surgical risk score is a term depending on a weighted sum of the measured values multiplied by the respective weights $\beta_i$ for the set of selected features, when the final statistical learning technique is a respective regression technique.

According to this other example, the surgical risk score is equal to an exponential of the weighted sum, typically calculated with the previous equation.

An optional addition, during the machine learning and before obtaining artificial features, additional values of the plurality of non-artificial features are generated based on the obtained values and using a data augmentation technique. According to this optional addition, the artificial features are then obtained according to both the obtained values and the generated additional values.

According to this optional addition, the data augmentation technique is typically a non-synthetic technique or a synthetic technique. The data augmentation technique is for example chosen among the group consisting of: SMOTE technique, ADASYN technique and SVMSMOTE technique.

According to this optional addition, for a given non-artificial feature, the less values have been obtained, the more additional values are generated.

According to this optional addition, this generation of additional values using the data augmentation technique is an optional additional step before the bootstrapping process. According to the above, this generation allows "augmenting" the initial input matrix X and the corresponding output vector Y with the data augmentation algorithm, namely increasing the respective sizes of the matrix X and the vector Y. If the matrix X is of size (n,p) and the vector Y is of size (n). This generation step leads to $X_{augmented}$ of size (n', p) and $Y_{augmented}$ of size (n') where n'>n.

This generation is preferably more sophisticated than the bootstrapping process. The goal is to 'augment' the inputs by creating synthetic samples, built using the obtained ones, and not by random duplication of samples. Indeed, if the non-artificial feature values would simply duplicated, the augmentation would not be fundamentally different from the bootstrapping process where non-artificial feature values may already be oversampled and/or duplicated. In the optional addition of data augmentation, the bootstrapping process will therefore be fed with new data points added to the original ones.

For classification, the data augmentation technique is for example the SMOTE technique, also called SMOTE algorithm or SMOTE. SMOTE first selects a minority class instance A at random and finds its K nearest minority class neighbors (using K Nearest Neighbor). The synthetic instance is then created by choosing one of the K nearest neighbors B at random and connecting A and B to form a line segment in the feature space. The synthetic instances are generated as a convex combination of the two chosen instances. The skilled person will notice that this technique is also a way of artificially balancing the classes. As a variant, the data augmentation technique is the ADASYN technique or the SVMSMOTE technique.

In the case of the surgical site complications, namely when the determined risk is SSC, the algorithm is applied to each layer independently. The layers used for determining the SSC are for example the following ones: the immune cell frequency (containing 24 cell frequency features), the basal signaling activity of each cell subset (312 basal signaling features), the signaling response capacity to each stimulation condition (six data layers containing 312 features each), and the plasma proteomic (276 proteomic features).

As an example, for each layer, there are 41 samples. In other words, the number n of feature values for each feature is equal to 41 in this example. Accordingly, for the immune frequency layer, the dimensions of the matrix X are 41 samples (n) by 24 features (p). In the case of basal signaling, the matrix X is of dimension 41×312. Y is the vector of outcome values, namely the occurrence of SSC. This vector Y is in this case a vector of length 41. Accordingly, one respective outcome value, i.e. one SSC value, is determined for each sample.

In this example, M is chosen equal to 10 000, which allows for enough sampling to derive an estimate of the frequency of selection over artificial features.

The chosen range value for the hyperparameter $\lambda$ is between 0.5 and 100, with the statistical learning technique being the Lasso technique or the Elastic Net technique.

In this example, the frequency threshold is chosen equal to 3 times the mean of the occurrence frequencies obtained for the artificial features, so as to reduce variability and to allow a stringent control over the choice of the features.

In the hereinafter examples of FIGS. 2, 3A and 3B, the skilled person will notice that the mathematical operation used to obtain artificial features is the permutation or the sampling, and will understand that other mathematical operations would also be applicable, including the other ones mentioned in the above description, namely combination, knockoff and inference. Similarly, in these examples, the statistical learning techniques used to compute initial weights are sparse regression techniques, such as the Lasso and the Elastic Net, and the skilled person will also understand that other statistical learning techniques would also be applicable, including the other ones mentioned in the above description, namely non-sparse techniques and classification techniques. In these examples, the significant weights are non-zero weights and the skilled person will also understand that other significant weights would also be applicable, such as weights above the predefined weight threshold, in accordance with the type of the initial statistical learning technique, as explained above.

Figure 2:
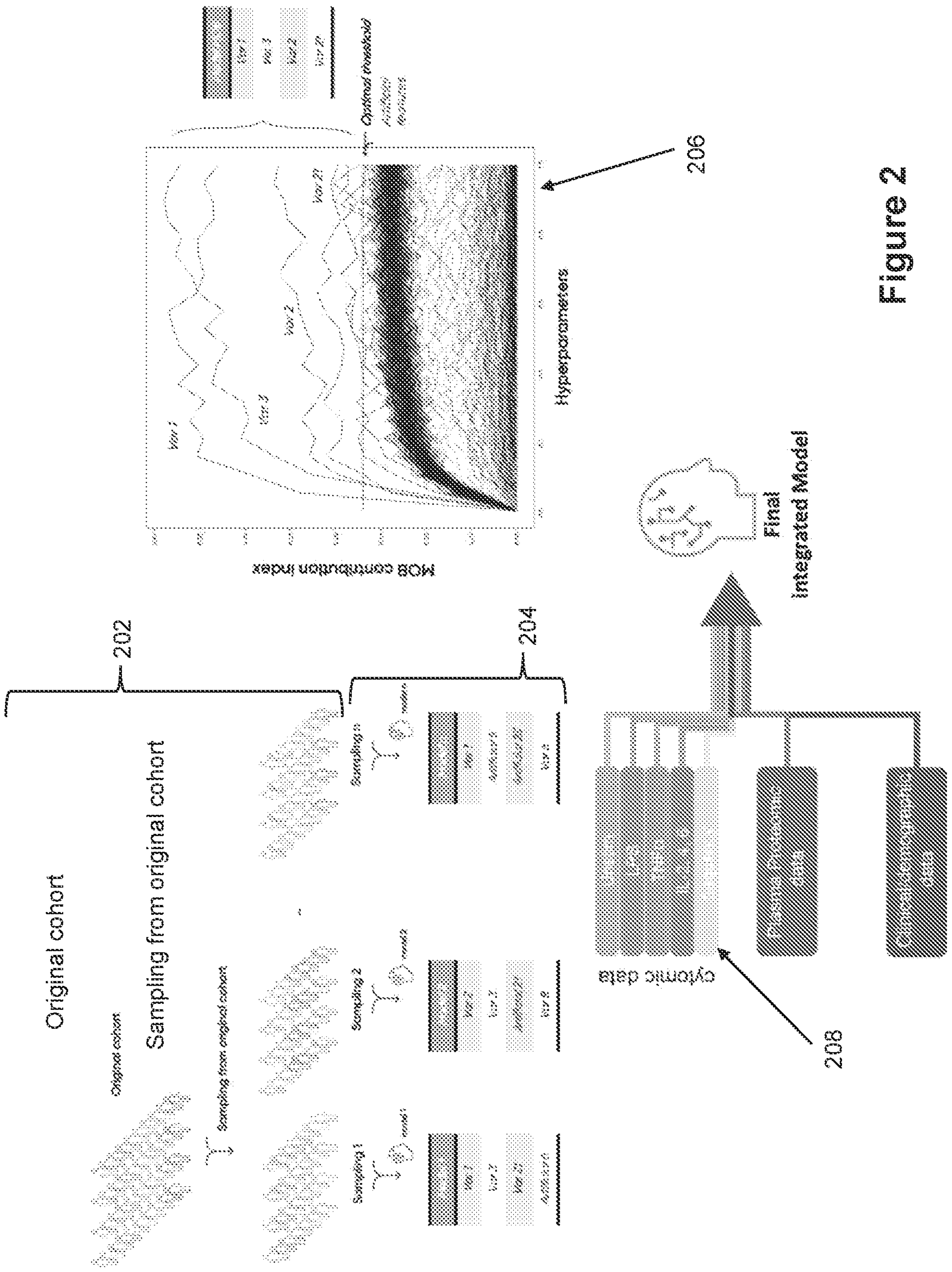
FIG. 2 illustrates an exemplary methodology for the MOB machine learning model that integrates biological and clinical data for the prediction of surgical outcomes in accordance with various embodiments.

Turning to FIG. 2, the MOB algorithm used in accordance with many embodiments is illustrated graphically. In such embodiments, at 202, subsets are obtained from an original cohort with a procedure using repeated sampling with or without replacement on individual data layers. In numerous embodiments, artificial features are included by random sampling from the distribution of the original sample or by permutation and added to the original dataset. At 204, on each of the subsets, individual models are computed using, for example, a Lasso algorithm and features are selected based on contribution in the model (in the case of Lasso, non-zero features are selected). At 206, Using the features selected for each model and by hyperparameter, many embodiments obtain stability paths that display the frequency of selection of each contributing feature (artificial or not). The distribution of selection of the artificial features are then used to estimate the distribution of the noise within the dataset. A cutoff for relevant biological or clinical features is computed based on the estimated distribution of the noise in the dataset. The relevant features from each layer are then used and combined in a final model for prediction of relevant surgical outcomes. At 208, final integration of the model where each of the individual layers are combined with a process of selection similar to the process described in 202-206). In 208, all the top features are combined and used as predictors in a final layer.

FIGS. 3A-3B illustrate exemplary pseudo-code for MOB algorithms of various embodiments. In many embodiments, the MOB uses a procedure of multiple resampling with or without replacement, called bootstrap, on individual data layers. In each data layer and for every repetition of the bootstrap, simulated features are spiked in the original dataset to estimate the robustness of selecting a biological feature compared to an artificial feature. An optimal cutoff for biological or clinical features is selected using the distribution of artificial features used to estimate the behavior of noise over biological or clinical features' robustness from the data layer. Then, the MOB algorithm selects the features above an optimal threshold calculated from the distribution of noise in each layer and builds a final model with the features from each data layer passing the optimal threshold of robustness. In many embodiments, performance is benchmarked, and stability is evaluated of feature selection on simulated data and biological data.

In the embodiments demonstrated FIGS. 3A-3B, such embodiments initially obtain subsets from the original cohort with a procedure using repeated sampling with or without replacement on individual data layers. For each bootstrap, artificial features are built by selecting the features (vectors of size p), one-by-one, of the original data matrix. To build an artificial feature, such embodiments either perform a random permutation (equivalent to randomly drawing without replacement all the values of the vector) or a random sampling (build a new vector of size p by randomly drawing with replacement p elements of the original feature). The process is repeated independently on each feature. Such embodiments concatenate the artificial features with the real features then draw with or without replacement samples from this concatenated dataset.

Next, for each of the subsets, individual models are computed using for example the Lasso algorithm (Tibshirani, R. (1996). Journal of the Royal Statistical Society: Series B (Methodological), 58(1), 267-288.) and features are selected based on contribution in the model (in the case of Lasso, non-zero features are selected). At this stage of the process, a contributing feature has a non-zero coefficient when fitting the Lasso. This would be the same for any other technique inducing sparsity such as Elastic Net. For non-sparse regression techniques, an arbitrary contribution threshold would have to be defined. The algorithm is adaptable to the machine learning technique used. Lasso is a well-known sparse regression technique, but other techniques that select a subset of the original features can be used. For instance, the Elastic Net (EN) as a combination of Lasso and Ridge would also work. (Zou, H., & Hastie, T. (2005). Journal of the royal statistical society: series B (statistical methodology), 67(2), 301-320.)

Further, using the features selected for each model and by hyperparameter, stability paths can be obtained, which display the frequency of selection of each contributing feature (artificial or real). A stability path is, before any graphical transformation the output matrix of the process. Its size is (p, #{Lambda}). Each value (feature_i, lambda_j) corresponds to the frequency of selection of the feature_i using the parameters lambda_j. From this matrix, such embodiments are able to display the path of each feature (e.g., FIG. 2, 206), where each line corresponds to the frequency of selection of each feature across all lambda tested. The distribution of selection of the artificial features are then used to estimate the distribution of the noise within the dataset. A cutoff for relevant biological or clinical features is computed based on the estimated distribution of the noise in the dataset. Only the relevant features from each layer are then used and combined in a final model for prediction of relevant surgical outcomes. In the embodiment of FIG. 3B, the final model uses the selected features obtained on each data layer. The input of the final model is therefore of size (n, p_stable), with p_stable being the number of selected features (all layers included). p_stable is significantly lower than the original feature space dimension. This reduced matrix is then train for prediction of the outcome.

The exemplary embodiment illustrated in FIG. 3B provides a broader range of hyperparameters. For example, the exemplary embodiment illustrated in FIG. 3A the choice of the optimal parameters is determined based on a optimization of the parameters at each bootstrap by minimizing the loss $\min_{\beta}||Y-\beta X||_2$ adding the constraint $||\beta||_1<\lambda$ on a Leave-One-Out Cross Validation fit, while the exemplary embodiment illustrated of FIG. 3B samples the results through various values of lambda, hence allowing for the plot of a "stability path."

Additionally, the exemplary embodiment of FIG. 3B allows the use of a selection threshold based on the distribution of all artificial features; specifically, the cutoff is defined based on the overall distribution of the artificial features. To define the cutoff, such embodiments take the maximum of probability of selection of each artificial features, then take the mean of these maximums. From this mean, such embodiments can build the threshold. (e.g., 3 standard deviations from the mean). In contrast, only the artificial feature with the maximum frequency of selection can be used in the embodiment illustrated in FIG. 3A.

Furthermore, the exemplary embodiment of FIG. 3B allows the combination of artificial generation and bootstrap procedure to simplify the complexity of the algorithm.

In more detail, embodiments, such as illustrated in FIG. 3B, provide:

1. Iteration over the number of bootstrap repetitions to get a proper evaluation of the sampling possibilities of artificial features selection. Index is tracked to see how sampling from the original distribution or via permutation behaves over multiple trials. This represents the first for loop in the algorithm and yields results in the lines 10-13.
2. The permutation or random sampling is obtained from the original dataset and the matrix generated is a juxtaposition of the original matrix and the new matrix of artificial features computed. The number of artificial features (p') can vary but typically is chosen to match the number of original features included in the algorithm. For computational purposes, if p is very large, we can choose a smaller number for p'.
3. In order to properly probe selection behavior over the chosen algorithm hyperparameters, a grid search like scheme is employed to evaluate different combinations of hyperparameters, then used to plot a curve of "stability paths" (see FIG. 2). This step is also a way to avoid missing information, if only a limited amount of hyperparameters is tested. The range of tested hyperparameters can be probed thoroughly to avoid artifacts (e.g., testing lambda=0 for the lasso will select all features for all bootstrap procedure, leading to the case where the max of frequencies of selection are all equal to 1).

4-6. With a given number of spikes and for each chosen value of hyperparameters, the resampling procedure allows for an estimate of the model fit behavior and to select features that are the most robust to small changes in the dataset. By model fit behavior, the model refers to the assessment of the probability of selection by the Lasso for a given value of the hyperparameters. The bootstrap (resampling procedure) allows to induce little perturbation in the original dataset and only the more robust features will be selected with a high frequency compared to others. The EN or Lasso algorithm tends to be very variable to small changes in the original cohort, especially in the sense that it can easily choses features that are not very robust, hence making biological interpretation and robustness over new cohorts difficult. In this setting, resampling creates small variations around the original cohort. This procedure can properly probe robustness in the feature selection 8. Extraction of the coefficients, with the sparsity induced by L1 regularization, using a simple cutoff of non-zero coefficient (typically 1e-5 in absolute value) to select top performing feature at each step of the bootstrap procedure. This selection of top performing feature at each iteration of the bootstrap procedure allows the model to derive a frequency of selection for each feature of the dataset.

10-12. Because the model includes spiked artificial features, the model can use the definition of the stability paths to estimate the distribution of typical "noise" in the dataset and use this distribution to compute a cutoff for relevant features. This cutoff is typically 2 standard deviations over the mean or median stability path of artificial features or 3 times the mean of the max probability of selection of artificial features. An arbitrary fix threshold can also be added, to take the maximum between the constructed threshold and the arbitrary fix one. Some embodiments take the maximum of probability of selection for each artificial features and then take the mean of these maximum to build the threshold (2*, 3* or combination of this and an arbitrary fix threshold).

Figure 4:
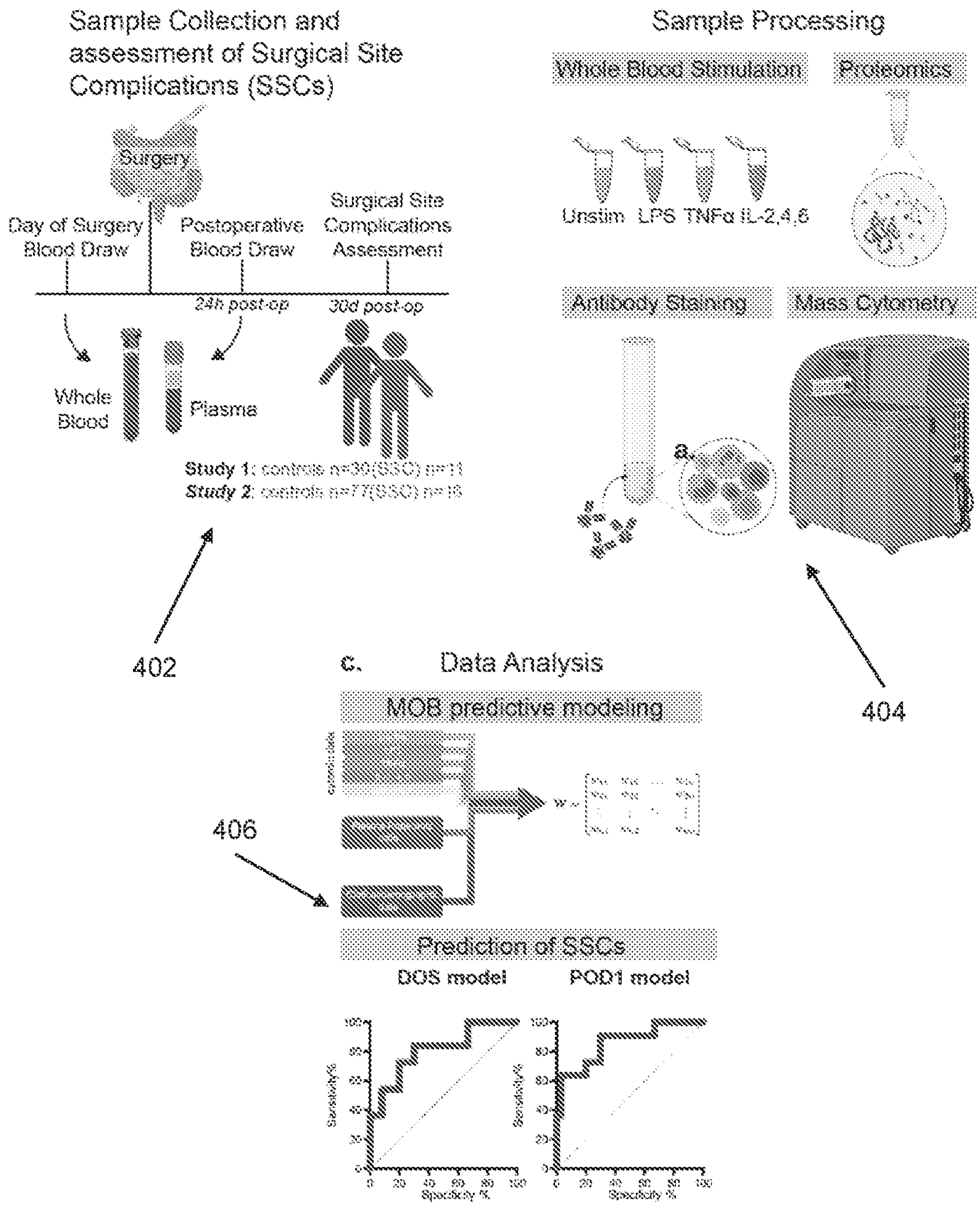
FIG. 4 illustrates an exemplary workflow for the identification of a predictive model of surgical site complications in patients undergoing abdominal surgery in accordance with various embodiments.

Turning to FIG. 4, an exemplary method to generate multi-omic biological data and generating a predictive MOB model of SSCs that integrates multi-omic biological data and clinical data is illustrated. At 402, certain embodiments obtain biological samples from an individual. While FIG. 4 illustrates blood draws (whole blood and plasma), various embodiments obtain biological samples from other tissues, fluids, and/or another biological source. Biological samples can be obtained before surgery (including day of surgery or "DOS") and/or after surgery. Pre-surgery samples can be obtained 7 days, 6 days, 5 days, 4 days, 3 days, 2 days, 1 day, and/or 0 days (i.e., day of surgery and before first incision), while post-surgery samples can be obtained within 24 hours after the surgery, including 0 hours, 1 hour, 3 hours, 6 hours, 8 hours, 10 hours, 12 hours, 16 hours, 18 hours, and/or 24 hours after surgery (i.e. Post-Operative Day 1, POD1). Multi-omic data is obtained from the biological sample at 404 of many embodiments. Such multi-omic data can include cytomic data obtained with mass cytometry and plasma protein expression data. Further embodiments utilize additional forms of omics data to identify cytomic, proteomic, transcriptomic, and/or genomic data as applicable for a particular embodiment. In certain embodiments, a predictive MOB model is generated based on the omic (including multi-omic) data and/or clinical data is generated at 406, where such models can be generated by the methods as described herein.

Figure 5A:
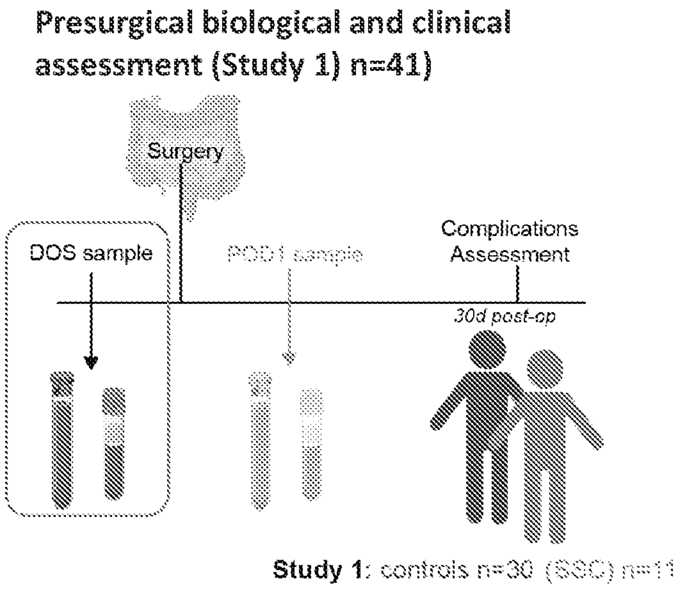
FIGS. 5A-5C illustrate an exemplary MOB predictive model of SSCs derived from the analysis of patient samples collected before an abdominal surgery, in accordance with various embodiments.
Figure 5B:
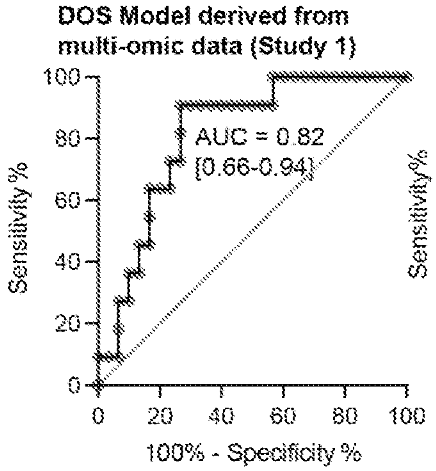
Figure 5C:
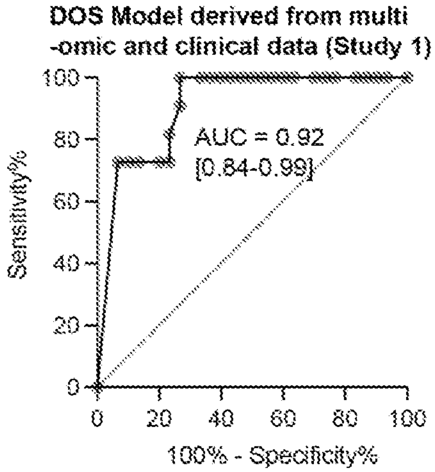

Turning to FIGS. 5A-5C, an exemplary embodiment showing the efficacy of the embodiment to predict SSCs after an abdominal surgery. Specifically, FIG. 5A points to biological samples obtained before surgery (on the DOS) coupled with post-operative assessment at 30 days post-surgery. A summary of the data used is provided in Table 1. FIG. 5B illustrates exemplary data showing an AUC of 0.82 (95% confidence interval, CI [0.66-0.94], Mann Whitney rank-sum test) for a model trained solely on multi-omic data. However, many embodiments implement a machine learning approach that integrates multi-omic and clinical data to derive a predictive model of SSC. FIG. 5C illustrates an exemplary MOB model that integrates pre-operative clinical variables to cytomic and plasma proteomic variables collected on the DOS that predicts SSCs with a superior predictive performance (AUC=0.92, 95% CI [0.84-0.99], Mann Whitney rank-sum test) than a model built on biological or clinical data alone.

Figure 6:
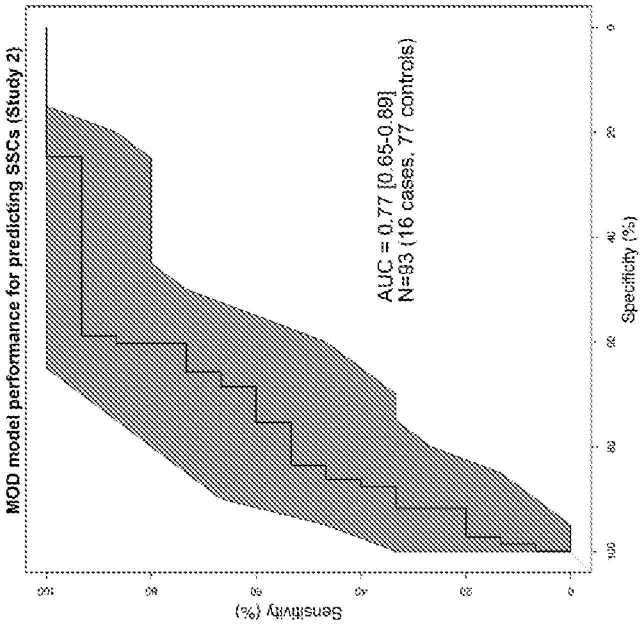
FIG. 6 illustrates an exemplary MOB predictive model of SSCs derived from the integrated analysis of multi-omic biological data collected from patients in accordance with various embodiments.
Figure 7:
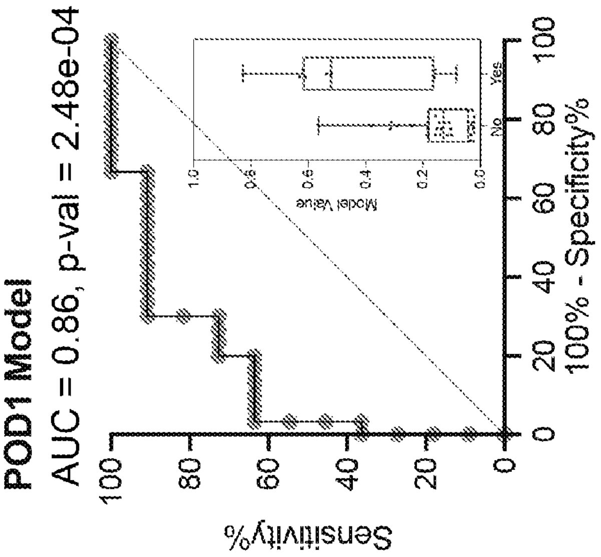
FIG. 7 illustrates an exemplary MOB predictive model of SSCs derived from the analysis patient samples collected 24 h after an abdominal surgery in accordance with various embodiments.

Additionally, FIGS. 6-7 illustrate exemplary performance data of additional embodiments. Specifically, FIG. 6 illustrates another exemplary DOS model that predicts SSCs with an AUC of 0.77, 95% CI [0.65-0.89], n=93, Mann Whitney rank-sum test—a summary of the data used to generate FIG. 6 is provided in Table 2. Further, FIG. 7 illustrates an exemplary MOB predictive model of SSCs derived from the analysis patient samples collected 24 h after an abdominal surgery (POD1) having an AUC of 0.86.

Methods for Generating Multi-Omic Biological Data

In many embodiments, the methods for generating a predictive model of surgical complication, such as SSC, relies on the multi-omic analysis of biological samples (e.g. blood-based samples, tumor samples, and/or any other suitable biological sample) obtained from an individual before or after surgery to obtain a determination of changes e.g., in immune cell subset frequencies and signaling activities, and in plasma proteins.

The biological sample can be any suitable type that allows for the analysis of one or more cells, proteins, preferably a blood sample. Samples can be obtained once or multiple times from an individual. Multiple samples can be obtained from different locations in the individual, at different times from the individual, or any combination thereof.

According to certain embodiments, at least one biological sample is obtained prior to surgery (including day of surgery or "DOS"). According to certain embodiments, at least one biological sample is obtained after surgery. According to certain embodiments, at least one biological sample is obtained prior to surgery and at least one biological sample is obtained after surgery. Pre-surgery biological samples can be obtained 7 days, 6 days, 5 days, 4 days, 3 days, 2 days, 1 day, and/or 0 day (i.e., on the day of surgery and before first incision). Post-surgery biological samples can be obtained within 24 hours after the surgery, including 0 hour, 1 hour, 3 hours, 6 hours, 8 hours, 10 hours, 12 hours, 16 hours, 18 hours, and/or 24 hours after surgery (i.e. POD1).

The biological samples can be from any source that contains immune cells. In some embodiments the biological sample(s) for analysis of immune cell responses is blood. However, the PBMC fraction of blood samples can also be utilized. In some embodiments the biological sample for proteomic analysis is the plasma fraction of a blood sample, however the serum fraction can also be utilized.

In some embodiments, samples are activated ex vivo, which as used herein refers to the contacting of a sample, e.g. a blood sample or cells derived therefrom, outside of the body with a stimulating agent (an example of which is illustrated at FIG. 4, 404). In some embodiments whole blood is preferred. The sample may be diluted or suspended in a suitable medium that maintains the viability of the cells, e.g. minimal media, PBS, etc. The sample can be fresh or frozen. Stimulating agents of interest include those agents that activate innate or adaptive cells, e.g. one or a combination of a TLR4 agonist such as LPS and/or IL-1β, IL-2, IL-4, IL-6, TNFα, IFNα, or PMA/ionomycin. Generally, the activation of cells ex vivo is compared to a negative control, e.g. medium only, or an agent that does not elicit activation. The cells are incubated for a period of time sufficient for activation of immune cells in the biological sample. For example, the time for activation can be up to about 1 hour, up to about 45 minutes, up to about 30 minutes, up to about 15 minutes, and may be up to about 10 minutes or up to about 5 minutes. In some embodiments the period of time is up to about 24 hours, or from about 5 to about 240 minutes. Following activation, the cells are fixed for analysis.

In many embodiments, cytomic, and proteomic features are detected using affinity reagents. "Affinity reagent", or "specific binding member" may be used to refer to an affinity reagent, such as an antibody, ligand, etc. that selectively binds to a protein or marker of the invention. The term "affinity reagent" includes any molecule, e.g., peptide, nucleic acid, small organic molecule. For some purposes, an affinity reagent selectively binds to a cell surface or intracellular marker, e.g. CD3, CD4, CD7, CD8, CD11b, CD11c, CD14, CD15, CD16, CD19, CD24, CD25, CD27, CD33, CD45, CD45RA, CD56, CD61, CD66, CD123, CD235ab, HLA-DR, CCR2, CCR7, TCRγδ, OLMF4, CRTH2, and CXCR4 and the like. For other purposes an affinity reagent selectively binds to a cellular signaling protein, particularly one which is capable of detecting an activation state of a signaling protein over another activation state of the signaling protein. Signaling proteins of interest include, without limitation, pSTAT3, pSTAT1, pCREB, pSTAT6, pPLCγ2, pSTAT5, pSTAT4, pERK1/2, pP38, prpS6, pNF-κB (p65), pMAPKAPK2 (pMK2), pP90RSK, IκB, cPARP, FoxP3, and Tbet.

In some embodiments, proteomic features are measured and comprise measuring circulating extracellular proteins. Accordingly, other affinity reagents of interest bind to plasma proteins. Plasma protein targets of particular interest include IL-1β, ALK, WWOX, HSPH1, IRF6, CTNNA3, CCL3, STREM1, ITM2A, TGFα, LIF, ADA, ITGB3, EIF5A, KRT19, and NTproBNP.

In some embodiments, cytomic features are measured and comprise measuring single cell levels of surface or intracellular proteins in an immune cell subset. Immune cell subsets include for instance neutrophils, granulocytes, basophils, monocytes, dendritic cells (DC) such as myeloid dendritic cells (mDC) or plasmacytoid dendritic cells (pDC), B-Cells or T-cells, such as regulatory T Cells (Tregs), naïve T Cells, memory T cells and NK-T cells. Immune cell subsets include more specifically neutrophils, granulocytes, basophils, $CXCR4^+$neutrophils, $OLMF4^+$neutrophils, $CD14^+CD16^-$ classical monocytes (cMC), $CD14^-CD16^+$ nonclassical monocytes (ncMC), $CD14^+CD16^+$ intermediate monocytes (iMC), $HLADR^+CD11c^+$ myeloid dendritic cells (mDC), $HLADR^+CD123^+$ plasmacytoid dendritic cells (pDC), $CD14^+HLADR^-CD11b^+$ monocytic myeloid derived suppressor cells (M-MDSC), $CD3^+CD56^+$ NK-T cells, $CD7^+CD19^-CD3^-$ NK cells, $CD7^+$ CD56loCD16hi NK cells, $CD7^+CD56^{hi}CD16^{lo}$ NK cells, $CD19^+$ B-Cells, $CD19^+CD38^+$ Plasma Cells, $CD19^+CD38-$ non-plasma B-Cells, $CD4^+$ $CD45RA^+$ naïve T Cells, $CD4^+$ CD45RA− memory T cells, $CD4^+CD161^+$ Th17 cells, $CD4^+Tbet^+$ Th1 cells, $CD4^+CRTH2^+$ Th2 cells, $CD3^+TCR\gamma\delta^+$ γδT Cells, Th17 $CD4^+$T cells, $CD3^+FoxP3^+CD25^+$ regulatory T Cells (Tregs), $CD8^+$ $CD45RA^+$ naïve T Cells, and $CD8^+$ CD45RA− memory T Cells.

In some embodiments both proteomic features and cytomic features are measured in a biological sample.

In some embodiments, the affinity reagent is a peptide, polypeptide, oligopeptide or a protein, particularly antibodies, or an oligonucleotide, particularly aptamers and specific binding fragments and variants thereof. The peptide, polypeptide, oligopeptide or protein can be made up of naturally occurring amino acids and peptide bonds, or synthetic peptidomimetic structures. Thus "amino acid", or "peptide residue", as used herein include both naturally occurring and synthetic amino acids. Proteins including non-naturally occurring amino acids can be synthesized or in some cases, made recombinantly; see van Hest et al., FEBS Lett 428:(I-2) 68-70 May 22, 1998 and Tang et al., Abstr. Pap Am. Chem. S218: U138 Part 2 Aug. 22, 1999, both of which are expressly incorporated by reference herein.

Many antibodies, many of which are commercially available (for example, see Cell Signaling Technology, www.cellsignal.com or Becton Dickinson, www.bd.com) have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein and plasma proteins. Examples of proteins that can be analyzed with the methods described herein include, but are not limited to, phospho (p) rpS6, pNF-κB (p65), pMAPKAPK2 (pMK2), pSTAT5, pSTAT1, pSTAT3, etc.

The methods the invention may utilize affinity reagents comprising a label, labeling element, or tag. By label or labeling element is meant a molecule that can be directly (i.e., a primary label) or indirectly (i.e., a secondary label) detected; for example, a label can be visualized and/or measured or otherwise identified so that its presence or absence can be known.

A compound can be directly or indirectly conjugated to a label which provides a detectable signal, e.g. non-radioactive isotopes, radioisotopes, fluorophores, enzymes, antibodies, oligonucleotides, particles such as magnetic particles, chemiluminescent molecules, molecules that can be detected by mass spec, or specific binding molecules, etc. Specific binding molecules include pairs, such as biotin and streptavidin, digoxin and anti-digoxin etc. Examples of labels include, but are not limited to, metal isotopes, optical fluorescent and chromogenic dyes including labels, label enzymes and radioisotopes. In some embodiments of the invention, these labels can be conjugated to the affinity reagents. In some embodiments, one or more affinity reagents are uniquely labeled.

Labels include optical labels such as fluorescent dyes or moieties. Fluorophores can be either "small molecule" fluors, or proteinaceous fluors (e.g. green fluorescent proteins and all variants thereof). In some embodiments, activation state-specific antibodies are labeled with quantum dots as disclosed by Chattopadhyay et al. (2006) Nat. Med. 12, 972-977. Quantum dot labeled antibodies can be used alone or they can be employed in conjunction with organic fluorochrome-conjugated antibodies to increase the total number of labels available. As the number of labeled antibodies increase so does the ability for subtyping known cell populations.

Antibodies can be labeled using chelated or caged lanthanides as disclosed by Erkki et al. (1988) J. Histochemistry Cytochemistry, 36:1449-1451, and U.S. Pat. No. 7,018, 850. Other labels are tags suitable for Inductively Coupled Plasma Mass Spectrometer (ICP-MS) as disclosed in Tanner et al. (2007) Spectrochimica Acta Part B: Atomic Spectroscopy 62(3):188-195. Isotope labels suitable for mass cytometry may be used, for example as described in published application US 2012-0178183.

Alternatively, detection systems based on FRET can be used. FRET find use in the invention, for example, in detecting activation states that involve clustering or multimerization wherein the proximity of two FRET labels is altered due to activation. In some embodiments, at least two fluorescent labels are used which are members of a fluorescence resonance energy transfer (FRET) pair.

When using fluorescent labeled components in the methods and compositions of the present invention, it will be recognized that different types of fluorescent monitoring systems, e.g., cytometric measurement device systems, can be used to practice the invention. In some embodiments, flow cytometric systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y. L., San Diego: Academic Press (1989), pp. 219-243; Turro, N. J., Modern Molecular Photochemistry, Menlo Park: Benjamin/Cummings Publishing Col, Inc. (1978), pp. 296-361.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., W099/54494, filed Apr. 16, 1999; U.S. Ser. No. 20010006787, filed Jul. 5, 2001, each expressly incorporated herein by reference).

In some embodiments, a FACS cell sorter (e.g. a FACSVantage™ Cell Sorter, Becton Dickinson Immunocytometry Systems, San Jose, Calif.) is used to sort and collect cells based on their activation profile (positive cells) in the presence or absence of an increase in activation level in an signaling protein in response to a modulator. Other flow cytometers that are commercially available include the LSR II and the Canto II both available from Becton Dickinson. See Shapiro, Howard M., Practical Flow Cytometry, $4^{th}$ Ed., John Wiley & Sons, Inc., 2003 for additional information on flow cytometers.

In some embodiments, the cells are first contacted with labeled activation state-specific affinity reagents (e.g. antibodies) directed against specific activation state of specific signaling proteins. In such an embodiment, the amount of bound affinity reagent on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™. Training Manual, with particular reference to sections 3-11 to 3-28 and 10-1 to 10-17, which is hereby incorporated by reference in its entirety. See the patents, applications and articles referred to, and incorporated above for detection systems.

In some embodiments, the activation level of an intracellular protein is measured using Inductively Coupled Plasma Mass Spectrometer (ICP-MS). An affinity reagent that has been labeled with a specific element binds to a marker of interest. When the cell is introduced into the ICP, it is atomized and ionized. The elemental composition of the cell, including the labeled affinity reagent that is bound to the signaling protein, is measured. The presence and intensity of the signals corresponding to the labels on the affinity reagent indicates the level of the signaling protein on that cell (Tanner et al. Spectrochimica Acta Part B: Atomic Spectroscopy, 2007 March; 62(3):188-195.).

Mass cytometry, e.g. as described in the Examples provided herein, finds use on analysis. Mass cytometry, or CyTOF (DVS Sciences), is a variation of flow cytometry in which antibodies are labeled with heavy metal ion tags rather than fluorochromes. Readout is by time-of-flight mass spectrometry. This allows for the combination of many more antibody specificities in a single samples, without significant spillover between channels. For example, see Bodenmiller at a. (2012) Nature Biotechnology 30:858-867.

One or more cells or cell types or proteins can be isolated from body samples. The cells can be separated from body samples by red cell lysis, centrifugation, elutriation, density gradient separation, apheresis, affinity selection, panning, FACS, centrifugation with Hypaque, solid supports (magnetic beads, beads in columns, or other surfaces) with attached antibodies, etc. By using antibodies specific for markers identified with particular cell types, a relatively homogeneous population of cells can be obtained. Alternatively, a heterogeneous cell population can be used, e.g. circulating peripheral blood mononuclear cells.

In some embodiments, a phenotypic profile of a population of cells is determined by measuring the activation level of a signaling protein. The methods and compositions of the invention can be employed to examine and profile the status of any signaling protein in a cellular pathway, or collections of such signaling proteins. Single or multiple distinct pathways can be profiled (sequentially or simultaneously), or subsets of signaling proteins within a single pathway or across multiple pathways can be examined (sequentially or simultaneously).

In some embodiments, the basis for classifying cells is that the distribution of activation levels for one or more specific signaling proteins will differ among different phenotypes. A certain activation level, or more typically a range of activation levels for one or more signaling proteins seen in a cell or a population of cells, is indicative that that cell or population of cells belongs to a distinctive phenotype. Other measurements, such as cellular levels (e.g., expression levels) of biomolecules that may not contain signaling proteins, can also be used to classify cells in addition to activation levels of signaling proteins; it will be appreciated that these levels also will follow a distribution. Thus, the activation level or levels of one or more signaling proteins, optionally in conjunction with the level of one or more biomolecules that may or may not contain signaling proteins, of a cell or a population of cells can be used to classify a cell or a population of cells into a class. It is understood that activation levels can exist as a distribution and that an activation level of a particular element used to classify a cell can be a particular point on the distribution but more typically can be a portion of the distribution. In addition to activation levels of intracellular signaling proteins, levels of intracellular or extracellular biomolecules, e.g., proteins, can be used alone or in combination with activation states of signaling proteins to classify cells. Further, additional cellular elements, e.g., biomolecules or molecular complexes such as RNA, DNA, carbohydrates, metabolites, and the like, can be used in conjunction with activation states or expression levels in the classification of cells encompassed here.

Figure 10:
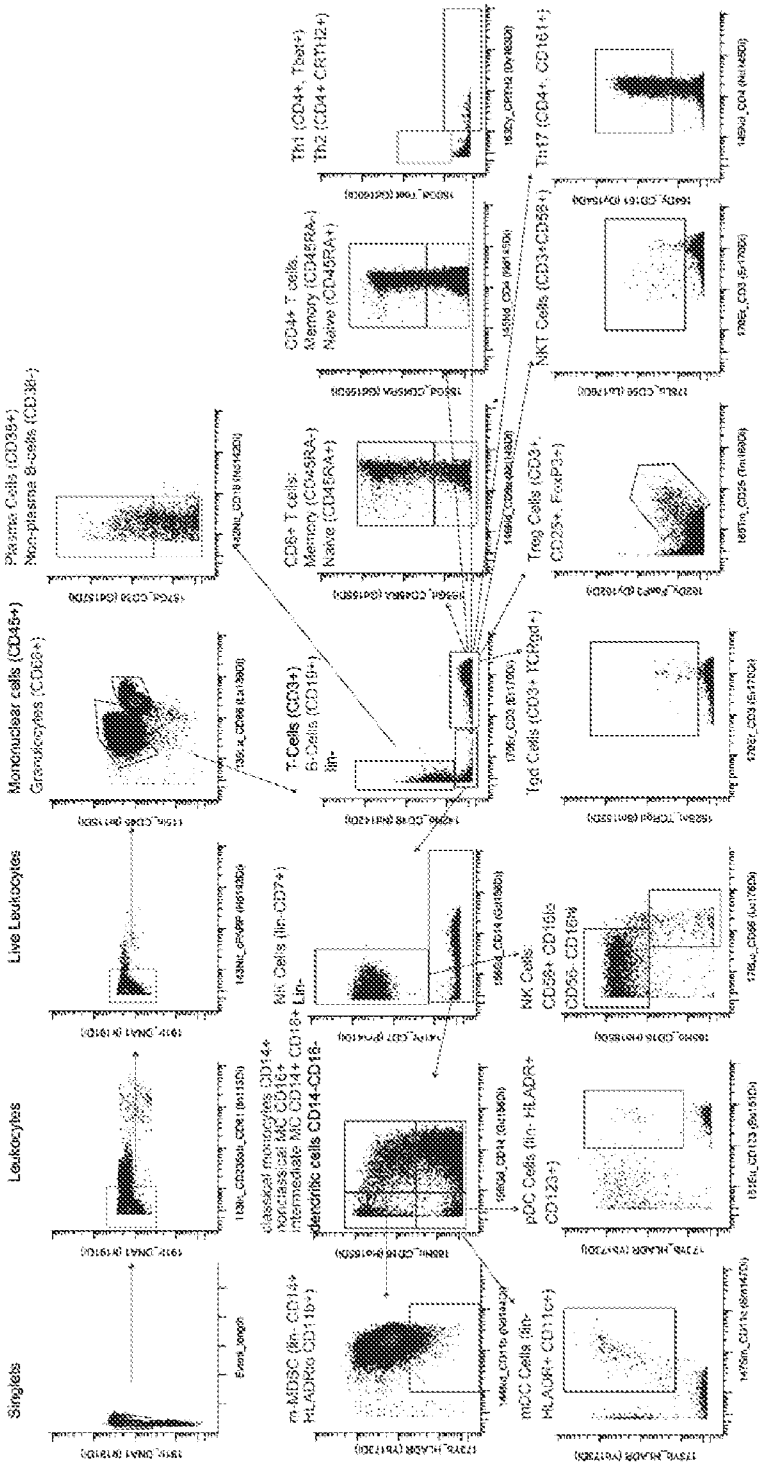
FIG. 10 illustrates an exemplary gating strategy for identification of immune cell subsets in accordance with various embodiments of the invention.

In some embodiments of the invention, different gating strategies can be used in order to analyze a specific cell population (e.g., only $CD4^+$ T cells) in a sample of mixed cell population. These gating strategies can be based on the presence of one or more specific surface markers. The following gate can differentiate between dead cells and live cells and the subsequent gating of live cells classifies them into, e.g. myeloid blasts, monocytes and lymphocytes. A clear comparison can be carried out by using two-dimensional contour plot representations, two-dimensional dot plot representations, and/or histograms. An exemplary gating strategy used for the analysis of patient samples is illustrated in FIG. 10.

The immune cells are analyzed for the presence of an activated form of a signaling protein of interest. Signaling proteins of interest include, without limitation, pMAPKAPK2 (pMK2), pP38, prpS6, pNF-κB (p65), IκB, pSTAT3, pSTAT1, pCREB, pSTAT6, pSTAT5, pERK. To determine if a change is significant the signal in a patient's baseline sample can be compared to a reference scale from a cohort of patients with known outcomes.

Samples may be obtained at one or more time points. Where a sample at a single time point is used, comparison is made to a reference "base line" level for the feature, which may be obtained from a normal control, a pre-determined level obtained from one or a population of individuals, from a negative control for ex vivo activation, and the like.

In some embodiments, the methods include the use of liquid handling components. The liquid handling systems can include robotic systems comprising any number of components. In addition, any or all of the steps outlined herein can be automated; thus, for example, the systems can be completely or partially automated. See U.S. Ser. No. 61/048,657. As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation.

In some embodiments, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this can be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

The differential presence of these markers is shown to provide for prognostic evaluations to detect individuals having a time to onset of labor. In general, such prognostic methods involve determining the presence or level of activated signaling proteins in an individual sample of immune cells. Detection can utilize one or a panel of specific binding members, e.g. a panel or cocktail of binding members specific for one, two, three, four, five or more markers.

The present invention incorporates information disclosed in other applications and texts. The following patent and other publications are hereby incorporated by reference in their entireties: Alberts et al., The Molecular Biology of the Cell, 4th Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7th Ed., Garland, and Leroith and Bondy, Growth Factors and Cytokines in Health and Disease, A Multi Volume Treatise, Volumes 1A and IB, Growth Factors, 1996.

Unless otherwise apparent from the context, all elements, steps or features described herein can be used in any combination with other elements, steps or features.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

Data Analysis

In many embodiments the methods for generating a predictive model of surgical complications, such as SSCs, employs the MOB algorithm herein described that integrates multi-omic biological and/or clinical data. In other embodiments, a predictive model of surgical complication, such as SSCs, or signature pattern associated with surgical complication, such as SSCs, can be generated from a biological sample using any convenient protocol, for example as described below. The readout can be a mean, average, median or the variance or other statistically or mathematically-derived value associated with the measurement. The marker readout information can be further refined by direct comparison with the corresponding reference or control pattern. A binding pattern can be evaluated on a number of points: to determine if there is a statistically significant change at any point in the data matrix relative to a reference value; whether the change is an increase or decrease in the binding; whether the change is specific for one or more physiological states, and the like. The absolute values obtained for each marker under identical conditions will display a variability that is inherent in live biological systems and also reflects the variability inherent between individuals.

Following obtainment of the signature pattern from the sample being assayed, the signature pattern can be compared with a reference or base line profile to make a prognosis regarding the phenotype of the patient from which the sample was obtained/derived. Additionally, a reference or control signature pattern can be a signature pattern that is obtained from a sample of a patient known to have a normal pregnancy.

In certain embodiments, the obtained signature pattern is compared to a single reference/control profile to obtain information regarding the phenotype of the patient being assayed. In yet other embodiments, the obtained signature pattern is compared to two or more different reference/control profiles to obtain more in-depth information regarding the phenotype of the patient. For example, the obtained signature pattern can be compared to a positive and negative reference profile to obtain confirmed information regarding whether the patient has the phenotype of interest.

Samples can be obtained from the tissues or fluids of an individual. For example, samples can be obtained from whole blood, tissue biopsy, serum, etc. Other sources of samples are body fluids such as lymph, cerebrospinal fluid, and the like. Also included in the term are derivatives and fractions of such cells and fluids.

In order to identify profiles that are indicative of responsiveness, a statistical test can provide a confidence level for a change in the level of markers between the test and reference profiles to be considered significant. The raw data can be initially analyzed by measuring the values for each marker, usually in duplicate, triplicate, quadruplicate or in 5-10 replicate features per marker. A test dataset is considered to be different than a reference dataset if one or more of the parameter values of the profile exceeds the limits that correspond to a predefined level of significance.

To provide significance ordering, the false discovery rate (FDR) can be determined. First, a set of null distributions of dissimilarity values is generated. In one embodiment, the values of observed profiles are permuted to create a sequence of distributions of correlation coefficients obtained out of chance, thereby creating an appropriate set of null distributions of correlation coefficients (see Tusher et al. (2001) PNAS 98, 5116-21, herein incorporated by reference). This analysis algorithm is currently available as a software "plug-in" for Microsoft Excel know as Significance Analysis of Microarrays (SAM). The set of null distribution is obtained by: permuting the values of each profile for all available profiles; calculating the pair-wise correlation coefficients for all profile; calculating the probability density function of the correlation coefficients for this permutation; and repeating the procedure for N times, where N is a large number, usually 300. Using the N distributions, one calculates an appropriate measure (mean, median, etc.) of the count of correlation coefficient values that their values exceed the value (of similarity) that is obtained from the distribution of experimentally observed similarity values at given significance level.

The FDR is the ratio of the number of the expected falsely significant correlations (estimated from the correlations greater than this selected Pearson correlation in the set of randomized data) to the number of correlations greater than this selected Pearson correlation in the empirical data (significant correlations). This cut-off correlation value can be applied to the correlations between experimental profiles.

For SAM, Z-scores represent another measure of variance in a dataset, and are equal to a value of X minus the mean of X, divided by the standard deviation. A Z-Score tells how a single data point compares to the normal data distribution. A Z-score demonstrates not only whether a datapoint lies above or below average, but how unusual the measurement is. The standard deviation is the average distance between each value in the dataset and the mean of the values in the dataset.

Using the aforementioned distribution, a level of confidence is chosen for significance. This is used to determine the lowest value of the correlation coefficient that exceeds the result that would have obtained by chance. Using this method, one obtains thresholds for positive correlation, negative correlation or both. Using this threshold(s), the user can filter the observed values of the pairwise correlation coefficients and eliminate those that do not exceed the threshold(s). Furthermore, an estimate of the false positive rate can be obtained for a given threshold. For each of the individual "random correlation" distributions, one can find how many observations fall outside the threshold range. This procedure provides a sequence of counts. The mean and the standard deviation of the sequence provide the average number of potential false positives and its standard deviation. Alternatively, any convenient method of statistical validation can be used.

The data can be subjected to non-supervised hierarchical clustering to reveal relationships among profiles. For example, hierarchical clustering can be performed, where the Pearson correlation is employed as the clustering metric. One approach is to consider a patient disease dataset as a "learning sample" in a problem of "supervised learning". CART is a standard in applications to medicine (Singer (1999) Recursive Partitioning in the Health Sciences, Springer), which can be modified by transforming any qualitative features to quantitative features; sorting them by attained significance levels, evaluated by sample reuse methods for Hotelling's $T^2$ statistic; and suitable application of the lasso method. Problems in prediction are turned into problems in regression without losing sight of prediction, indeed by making suitable use of the Gini criterion for classification in evaluating the quality of regressions.

Other methods of analysis that can be used include logistic regression. One method of logic regression Ruczinski (2003) Journal of Computational and Graphical Statistics 12:475-512. Logic regression resembles CART in that its classifier can be displayed as a binary tree. It is different in that each node has Boolean statements about features that are more general than the simple "and" statements produced by CART.

Another approach is that of nearest shrunken centroids (Tibshirani (2002) PNAS 99:6567-72). The technology is k-means-like, but has the advantage that by shrinking cluster centers, one automatically selects features (as in the lasso) so as to focus attention on small numbers of those that are informative. The approach is available as Prediction Analysis of Microarrays (PAM) software, a software "plug-in" for Microsoft Excel, and is widely used. Two further sets of algorithms are random forests (Breiman (2001) Machine Learning 45:5-32 and MART (Hastie (2001) The Elements of Statistical Learning, Springer). These two methods are already "committee methods." Thus, they involve predictors that "vote" on outcome. Several of these methods are based on the "R" software, developed at Stanford University, which provides a statistical framework that is continuously being improved and updated in an ongoing basis.

Other statistical analysis approaches including principle components analysis, recursive partitioning, predictive algorithms, Bayesian networks, and neural networks.

These tools and methods can be applied to several classification problems. For example, methods can be developed from the following comparisons: i) all cases versus all controls, ii) all cases versus nonresponsive controls, iii) all cases versus responsive controls.

In a second analytical approach, variables chosen in the cross-sectional analysis are separately employed as predictors. Given the specific outcome, the random lengths of time each patient will be observed, and selection of proteomic and other features, a parametric approach to analyzing responsiveness can be better than the widely applied semi-parametric Cox model. A Weibull parametric fit of survival permits the hazard rate to be monotonically increasing, decreasing, or constant, and also has a proportional hazards representation (as does the Cox model) and an accelerated failure-time representation. All the standard tools available in obtaining approximate maximum likelihood estimators of regression coefficients and functions of them are available with this model.

In addition, the Cox models can be used, especially since reductions of numbers of covariates to manageable size with the lasso will significantly simplify the analysis, allowing the possibility of an entirely nonparametric approach to survival.

The analysis and database storage can be implemented in hardware or software, or a combination of both. In one embodiment of the invention, a machine-readable storage medium is provided, the medium comprising a data storage material encoded with machine readable data which, when using a machine programmed with instructions for using said data, is capable of displaying a any of the datasets and data comparisons of this invention. Such data can be used for a variety of purposes, such as patient monitoring, initial diagnosis, and the like. Preferably, the invention is implemented in computer programs executing on programmable computers, comprising a processor, a data storage system (including volatile and non-volatile memory and/or storage elements), at least one input device, and at least one output device. Program code is applied to input data to perform the functions described above and generate output information. The output information is applied to one or more output devices, in known fashion. The computer can be, for example, a personal computer, microcomputer, or workstation of conventional design.

Each program is preferably implemented in a high level procedural or object-oriented programming language to communicate with a computer system. However, the programs can be implemented in assembly or machine language, if desired. In any case, the language can be a compiled or interpreted language. Each such computer program is preferably stored on a storage media or device readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

A variety of structural formats for the input and output means can be used to input and output the information in the computer-based systems of the present invention. One format for an output means test datasets possessing varying degrees of similarity to a trusted profile. Such presentation provides a skilled artisan with a ranking of similarities and identifies the degree of similarity contained in the test pattern.

The signature patterns and databases thereof can be provided in a variety of media to facilitate their use. "Media" refers to a manufacture that contains the signature pattern information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure can be chosen, based on the means used to access the stored information. A variety of data processor programs and formats can be used for storage, e.g. word processing text file, database format, etc.

Computer Executed Embodiments

Figure 13:
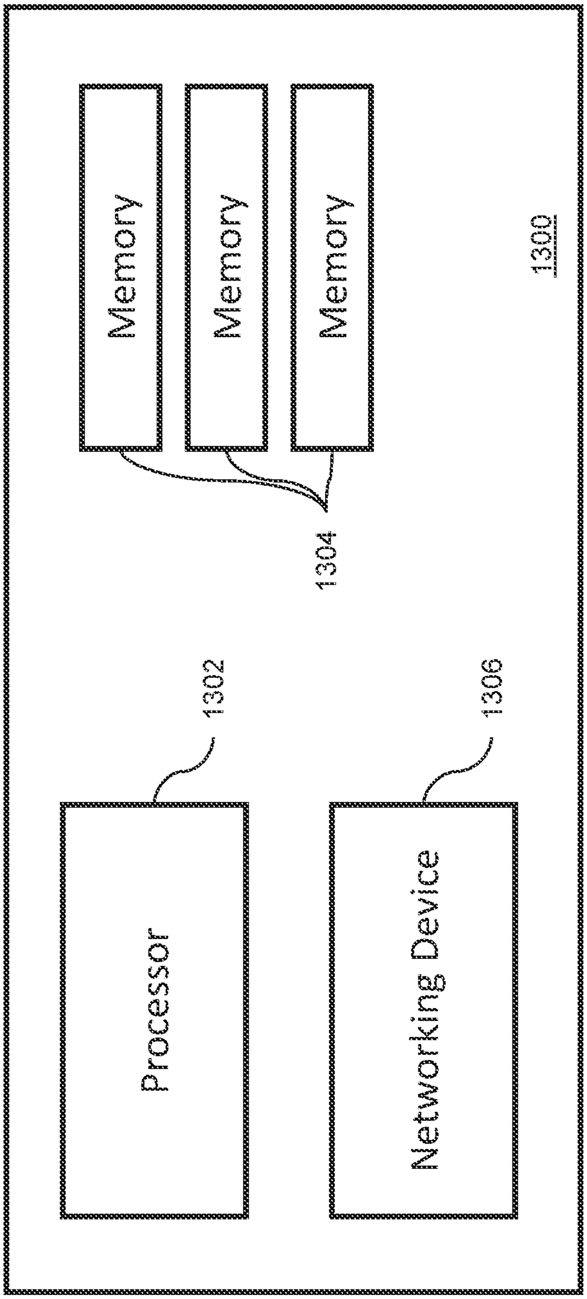
FIG. 13 illustrates a block diagram of components of a processing system in a computing device that can be used to generate a surgical risk score in accordance with an embodiment of the invention.

Processes that provide the methods and systems for generating a surgical risk score in accordance with some embodiments are executed by a computing device or computing system, such as a desktop computer, tablet, mobile device, laptop computer, notebook computer, server system, and/or any other device capable of performing one or more features, functions, methods, and/or steps as described herein. The relevant components in a computing device that can perform the processes in accordance with some embodiments are shown in FIG. 13. One skilled in the art will recognize that computing devices or systems may include other components that are omitted for brevity without departing from described embodiments. A computing device 1300 in accordance with such embodiments comprises a processor 1302 and at least one memory 1304. Memory 1304 can be a non-volatile memory and/or a volatile memory, and the processor 1302 is a processor, microprocessor, controller, or a combination of processors, microprocessor, and/or controllers that performs instructions stored in memory 1304. Such instructions stored in the memory 1304, when executed by the processor, can direct the processor, to perform one or more features, functions, methods, and/or steps as described herein. Any input information or data can be stored in the memory 1304—either the same memory or another memory. In accordance with various other embodiments, the computing device 1300 may have hardware and/or firmware that can include the instructions and/or perform these processes.

Certain embodiments can include a networking device 1306 to allow communication (wired, wireless, etc.) to another device, such as through a network, near-field communication, Bluetooth, infrared, radio frequency, and/or any other suitable communication system. Such systems can be beneficial for receiving data, information, or input (e.g., omic and/or clinical data) from another computing device and/or for transmitting data, information, or output (e.g., surgical risk score) to another device.

Figure 14:
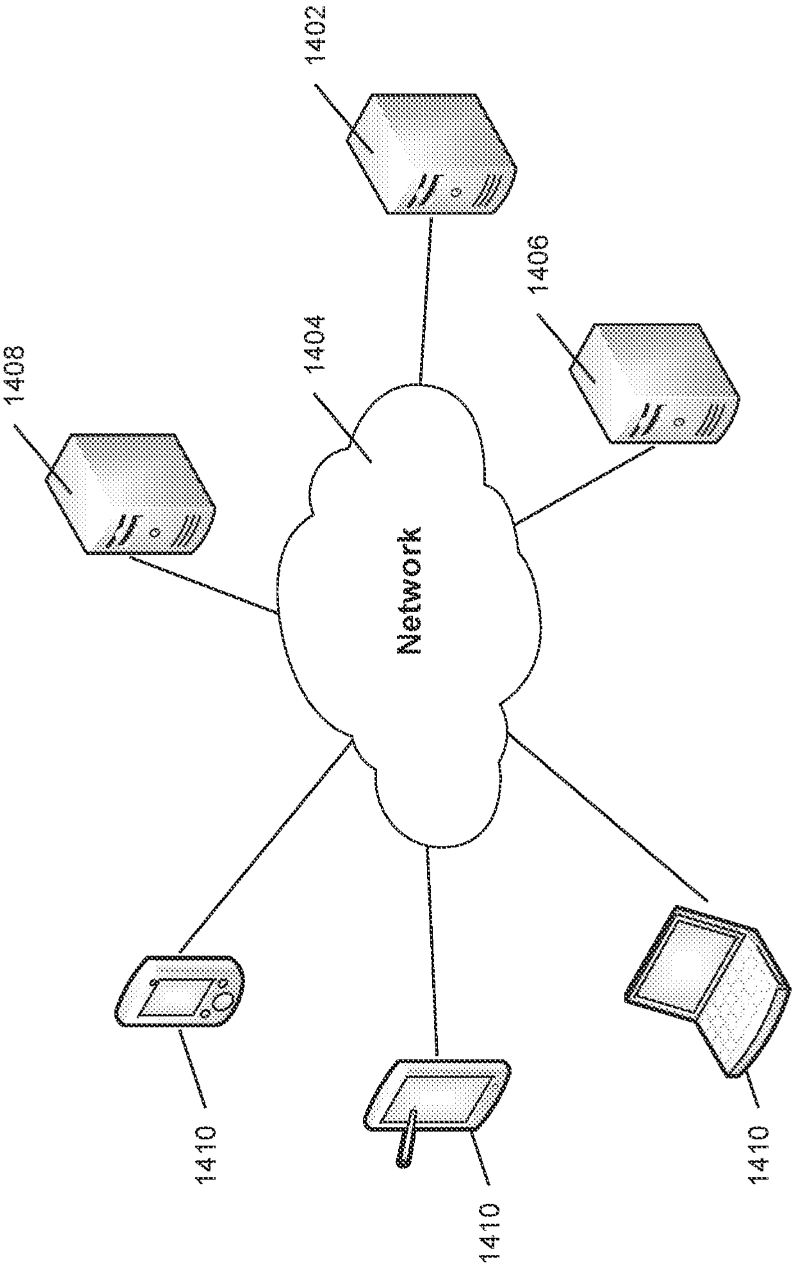
FIG. 14 illustrates a network diagram of a distributed system to generate a surgical risk score in accordance with an embodiment of the invention.

Turning to FIG. 14, an embodiment with distributed computing devices is illustrated. Such embodiments may be useful where computing power is not possible at a local level, and a central computing device (e.g., server) performs one or more features, functions, methods, and/or steps described herein. In such embodiments, a computing device 1402 (e.g., server) is connected to a network 1404 (wired and/or wireless), where it can receive inputs from one or more computing devices, including clinical data from a records database or repository 1406, omic data provided from a laboratory computing device 1408, and/or any other relevant information from one or more other remote devices 1410. Once computing device 1402 performs one or more features, functions, methods, and/or steps described herein, any outputs can be transmitted to one or more computing devices 1406, 1408, 1410 for entering into records, taking medical action—including (but not limited to) prehabilitation, delaying surgery, providing antibiotics—and/or any other action relevant to a surgical risk score. Such actions can be transmitted directly to a medical professional (e.g., via messaging, such as email, SMS, voice/vocal alert) for such action and/or entered into medical records.

In accordance with still other embodiments, the instructions for the processes can be stored in any of a variety of non-transitory computer readable media appropriate to a specific application.

Exemplary Embodiments

Although the following embodiments provide details on certain embodiments of the inventions, it should be understood that these are only exemplary in nature and are not intended to limit the scope of the invention.

Example 1: Combined Plasma and Single-Cell Proteomic Analysis of the Host's Immune Response to Major Abdominal Surgery Background: This study employed an integrated approach combining the functional analysis of immune cell subsets using mass cytometry with the highly-multiplexed assessment of inflammatory plasma proteins to quantify the dynamic changes of over 2,388 single-cell and plasma proteomic events in patients before and after major abdominal surgery.

Methods: Forty-one patients undergoing abdominal surgery who met inclusion criteria were enrolled before surgery (Table 1; FIG. 4). All patients underwent major, non-cancer abdominal surgery involving bowel resection. The primary outcome was the presence of a postoperative Surgical Site Complications (SSCs) within 30 days after surgery, including surgical site infection (organ space, deep, superficial), anastomotic leak or wound dehiscence. The rationale for combining the three surgical site complications into a single primary outcome is that anastomotic leaks and wound dehiscence are intimately linked to the pathogenesis of surgical site infection. Postoperative outcomes were reviewed 30 days after surgery. Eleven patients (27%) developed SSCs, including superficial surgical site infections, mucocutaneous separations around the stoma, and parastomal ulcerations. Clinical and operative characteristics for patients who did not develop surgical site complications and those who did can be found in Table 1. Patients who developed an SSC had significantly higher BMIs, operative duration, and estimated intraoperative blood loss.

For each study participant, a blood sample was collected on the day of surgery (DOS, prior to induction of general anesthesia), and on the first postoperative day (POD1). Blood samples were analyzed using a multimodal approach combining plasma proteomics (i.e. analysis of 274 plasma protein expression levels using the Olink platform; (see e.g., Assarsson E, et al. *PLoS One* 2014; 9(4):e95192; the disclosure of which is hereby incorporated by reference herein in its entirety;) and single-cell proteomics (i.e. single-cell analysis of circulating immune cells with mass cytometry, FIG. 4). For the mass cytometry analysis, a 39-parameter immunoassay was employed to quantify the frequency and intracellular signaling activities of all major innate and adaptive immune cells. The single-cell analysis was performed using unstimulated blood samples to quantify the frequency and endogenous signaling activities of immune cell subsets) as well as samples stimulated with a series of receptor-specific ligands eliciting key intracellular signaling responses implicated in the host immune response to trauma/injury [including, lipopolysaccharide (LPS), PMA/Ionomycin (PI), interleukin (IL)-1β, interferon (IFN)-α, tumor necrosis factor (TNF)α, and a combination of IL-2,4,6].

To estimate the effect of major abdominal surgery on the human immune system, a univariate analysis was performed comparing each plasma or single-cell proteomic feature before and after surgery. Differences between POD1 and DOS were calculated as log-fold change for plasma proteomic features or as the Arc sin h ratio for single-cell proteomic features and visualized on a volcano plot. Plasma and single-cell proteomic features were ranked according to the magnitude of the response to surgery.

Figure 11A:
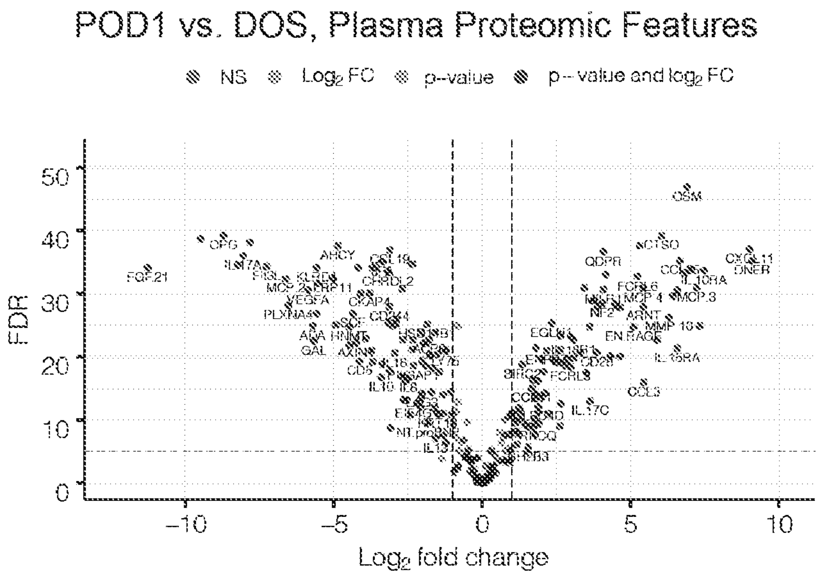
FIGS. 11A-11B illustrate exemplary set of single-cell immune responses and plasma protein differentially expressed before and after surgery in accordance with various embodiments of the invention.
Figure 11B:
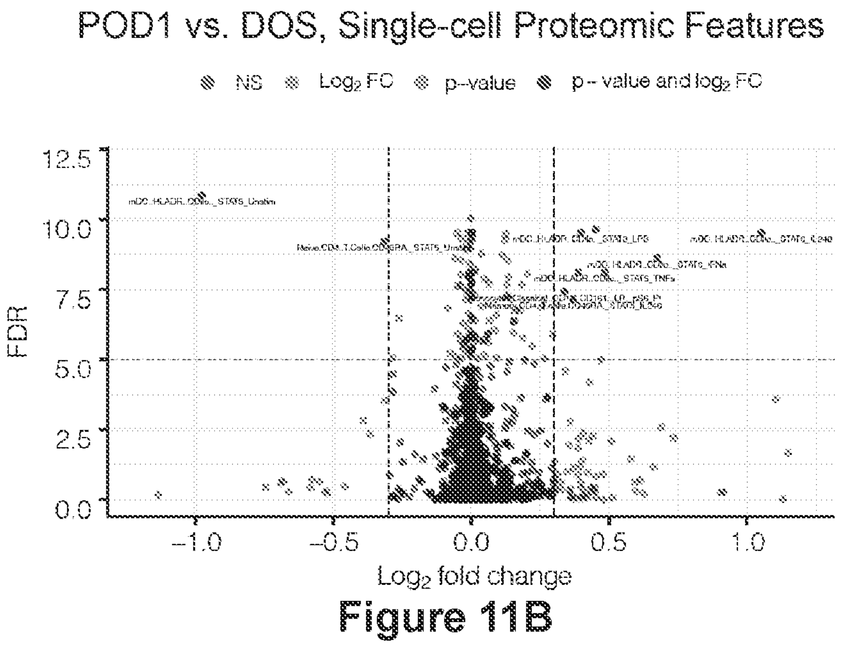

Results: A total of 224 proteomic and 421 mass cytometry features differed significantly (FDR<0.05) after surgery (FIGS. 11A-11B). Specifically, FIGS. 11A-11B illustrate changes in plasma proteomic (FIG. 11A) and single cell mass cytometry (FIG. 11B) innate and adaptive immune composition and function in response to surgical trauma are shown as volcano plots. Individual immune features which expression was higher for DOS samples are shown to the left (i.e., negative log 2 fold change), features which expression was higher for POD1 samples are shown to the right (i.e., positive log 2 fold change) Features with false discovery rate less than 5% are above the horizontal hashed bar (green dot p<0.05, blue dot log 2 FC, or red dot both p<0.05 and log 2 FC). Consistent with prior transcriptomic and mass cytometry analyses of the human immune response to traumatic injury, major abdominal surgery resulted in the simultaneous mobilization of the innate and adaptive branches of the human immune system. Specifically, examination of the top % differentially regulated features revealed a profound activation of innate immune responses, including increased pro-inflammatory cytokines such as members of the TNFα, IL-6 and IL-1 superfamily, increased chemotactic proteins (including CCL23 and CX3Cl1) and increased canonical inflammatory signaling responses (such as JAK/STAT signaling) in innate myeloid cell subsets. Conversely, adaptive immune cell frequencies (including CD4+ and CD8+ T cell subsets) and adaptive immune responses to inflammatory stimulation (notably JAK/STAT signaling responses to IL2/4/6 stimulation) as well as the concentration of regulatory proteins (such as IL-10RA) were decreased on POD1 compared to DOS. We also observed a robust increase in the frequency and JAK/STAT signaling activity of monocytic myeloid derived suppressor cells (M-MDSCs), a population of innate immune cells with immunosuppressive properties, that accumulate in the context of malignancies, sepsis, and severe trauma including surgery.

Conclusions: Overall, the differential immune profiling of patients before and 24 h after surgery showed that major abdominal surgery triggers a complex inflammatory response that engages pro-inflammatory as well as immunosuppressive elements of the innate and adaptive immune systems. Importantly, significant inter-patient variability existed in the magnitude of this immune response, which prompted further investigation into whether the variability between patients reflects patient-specific differences that could predetermine the development of surgical complications.

Example 2: Integrated Modeling of Multi-Omic Biological and Clinical Data Before Surgery Predicts Surgical Site Complications (SSCs)—Study 1

Background: The differential analysis of the immune responses on POD1 vs. DOS (example 1) highlights biological aspects of the human immune response to traumatic injury that may drive the pathogenesis of SSC. However, the ability to identify which patient will develop an SSC before surgery (i.e. on DOS) is of utmost clinical interest as it will allow risk stratification prior to surgery and personalization of pre-operative interventions.

Figure 12:
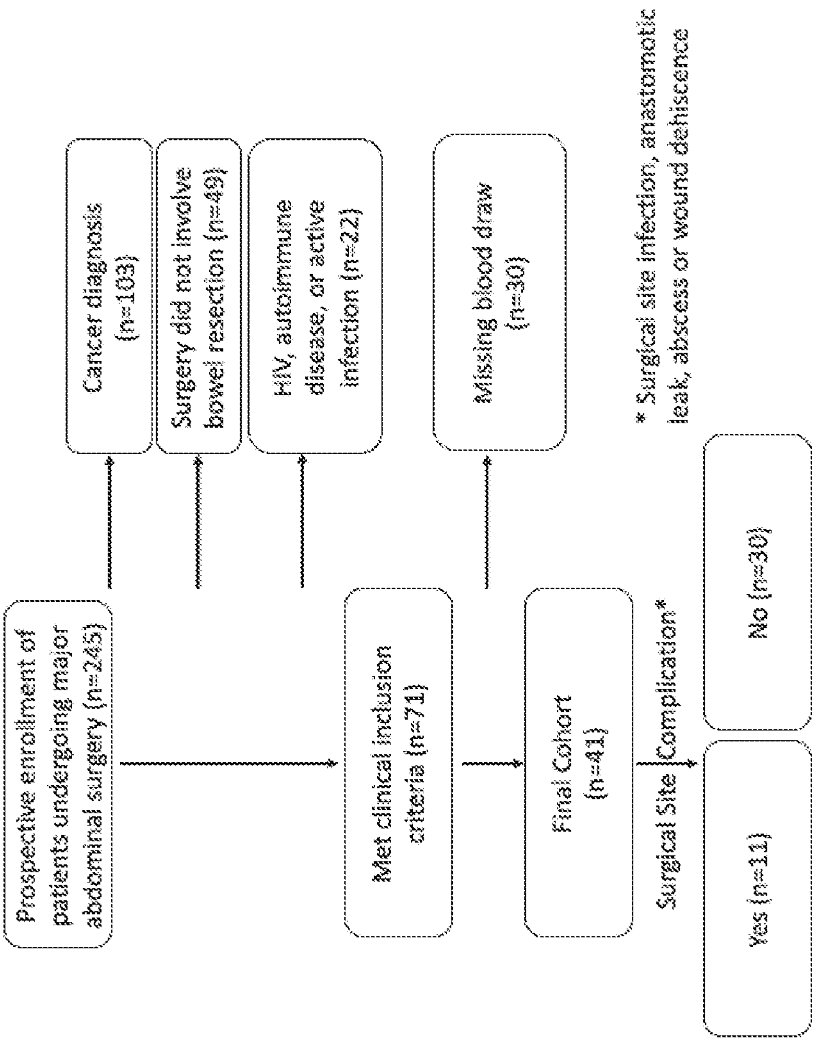
FIG. 12 illustrates an exemplary patient enrollment according to the CONSORT criteria in accordance with various embodiments of the invention.

Methods: FIG. 12 illustrates patient enrollment according to CONSORT criteria used in this study. Forty-one (41) patients were prospectively enrolled in Study 1, 11 patients developed SSCs within 30 days of surgery while 30 patients did not. Whole blood samples collected on the day of surgery (DOS) prior to incision and on Post-operative Day 1 (POD1) were stimulated with lipopolysaccharide (LPS), tumor necrosis factor (TNF)α, interleukin (IL)-2,4,6 cocktail, PMA/Ionomycin (P/I), interferon (IFN)α, IL-1β, or left unstimulated (Unstim). Whole blood samples were analyzed using a 47-parameter single-cell mass cytometry assay to quantify the abundance of all major innate and adaptive immune cell subsets and the single-cell intracellular activity of key signaling responses implicated in the immune response to surgical trauma. Plasma samples were analyzed using the Olink multiplex proteomic platform (Study 1, 274 protein analyzed). Table 5 provides a list of the antibody panel used in this study.

To determine whether the immune state of patients with and without SSC differs before surgery, an integrated Multi-Omic Bootstrap (MOB) analysis pipeline (FIGS. 2-3) was applied to the DOS immunological dataset (derived from samples collected before the induction of anesthesia and surgical incision). This approach leverages the interconnected and multi-layered nature of the combined plasma and single-cell proteomic dataset and offers a framework for integrated feature selection by selection based on robustness. The dataset contained nine unique data layers: the immune cell frequency (containing 24 cell frequency features), the basal signaling activity of each cell subset (312 basal signaling features), the signaling response capacity to each stimulation condition (six data layers containing 312 features each), and the plasma proteomic (276 proteomic features) data layers (FIG. 2, FIG. 4). This method uses several steps to integrate the nine data layers. First, on each layer, artificial features are introduced by permuting the original features, hence creating features unrelated to the outcome. Then, a bootstrap procedure repeating a fit of the machine learning model by resampling from this dataset with or without replacement is performed multiple times. Typically, the machine learning model used is a logistic or linear regression with L1 or L2 regularization, commonly described as the Lasso, Ridge, or Elastic Net models. The repetition of the procedure allows for an estimation of the distribution of the simulated noise and allows for a description of its distribution. For each variable (artificial or not) we compute a stability path, defined as the frequency of selection in the model from the non-zero features or features with the most importance in the model (for instance, in the biggest absolute value of the coefficients). An optimal cutoff for biological or clinical features is selected using the distribution of artificial features used to estimate the behavior of noise over biological or clinical features' robustness from the data layer.

Multi-omic biological features utilized for the MOB analysis were defined as follows. Single-cell proteomic features: 2,116 single-cell proteomic features were derived from the mass cytometry data as previously described[48] including cell frequency, endogenous signaling, and signaling responses to ex vivo stimulations. Immune cell frequency features were calculated for each immune cell subset from the unstimulated samples. Mononuclear cell frequency was determined as a percentage of live, singlet mononuclear cells (cPAPR$^-$CD45$^+$CD66$^-$). Granulocyte frequency was determined as a percentage of gated live, singlet cells (cPARP$^-$). For single-cell signaling features, the median expression of intracellular signaling proteomic markers were simultaneously quantified on a per cell basis for phospho-(p)STAT-1, pSTAT-3, pSTAT4, pSTAT5, pSTAT6, pNfκB, total IκBα, pMAPKAPK2 (pMK2), pERK1/2, prpS6, pCREB, Ki67, and PD-1. Endogenous signaling activity was expressed as the arc sin h transformed value from the unstimulated samples. Signaling responses to ex vivo stimulation were reported as the difference of arc sin h transformed median of the stimulated value from the endogenous value (a sin h ratio). A knowledge-based penalization matrix was applied to intracellular signaling response features in the mass cytometry data based on mechanistic immunological knowledge, as previously described. (See e.g., N. Aghaeepour et al (2017). Sci Immunol 2; the disclosure of which is hereby incorporated by reference herein in its entirety.) Importantly, mechanistic priors used in the penalization matrix is independent of immunological knowledge related to surgical recovery. Plasma proteomic features were quantified using the Olink immune response panel, inflammatory panel, and metabolism panel were used to quantify the concentration of 272 unique plasma proteins. Relative levels of plasma proteins are reported in arbitrary units calculated from data normalized to internal controls and reported after log 2 transformation.

Results: A robust MOB model was built that accurately differentiated patients with and without SSC (AUC=0.82, 95% CI [0.66-0.94], unpaired Mann-Whitney rank-sum test on the MOB model cross-validated values, FIG. 5B). The predictive performance of the MOB model was superior to existing predictive models of surgical outcomes such as the ACS NSQIP risk assessment score; (see e.g., Bilimoria K Y et al. J Am Coll Surg 2013; 217(5):833-42 e1-3; the disclosure of which is hereby incorporated by reference herein in its entirety;) that are based on clinical variables (ACS AUC=0.73). A confounder analysis, including clinical and demographic variables that differed between the two patient groups, showed that the MOB model captured significantly more information when accounting for differences in age, BMI, preoperative diagnostic features, and surgery type (Table 6). Comparison of a generalized linear model with or without the MOB predictions resulted in a significantly better fit for the model with the MOB values (p=8e-05, chi-sq. test for the deviance between fits). Finally, integration of pre-operative clinical variables (i.e. age, sex, bmi, functional status, emergency case, american society of anesthesiologists (ASA) class, steroid use for chronic condition, ascites, disseminated cancer, diabetes, hypertension, congestive heart failure, dyspnea, smoking history, history of severe COPD, dialysis, acute renal failure) to single-cell and plasma proteomic variables collected on the DOS further increased the accuracy of the DOS model for the prediction of SSC (AUC=0.92, 95% CI [0.84-0.99], FIG. 5C).

Conclusions: Together, the results suggest that the integration of immunological and clinical information collected before surgery has a strong potential for accurately identifying patients at risk for post-operative SSC. The predictive performance of the MOB model suggests that sufficiently powerful predictive models can be developed to risk stratify individual patients and to assign them to patient-specific care pathways aiming at decreasing the risk for developing and SSC.

Example 3: Integrated Modeling of Multi-Omic Biological Data Before Surgery Predicts SSCs—Study 2

Background: Results from the prospective Study 1 demonstrate that an accurate risk estimate of developing SSCs can be derived from the analysis of patients' immunological states before surgery. However clinical and demographic variables can influence a patients' immunological state and act as confounder for the development of SSC. To determine the contribution of patient's pre-operative immunological state to the development of SSC, a retrospective study (Study 2) was performed comparing two groups of patients undergoing major abdominal surgery that were matched based on major clinical and demographic variables. The primary outcome of the study was development of SSC within 30 days of surgery.

Methods: 93 patients undergoing major abdominal surgery at Stanford Hospital were selected from a larger cohort of 450 patients included in the Stanford Surgical Biobank (Table 2). 16 patients had developed an SSC (cases) while 77 patients did not (controls). Cases and controls were matched using a frequency matching algorithm that ensured equal distribution between groups of the following clinical and demographic variables: age, sex, BMI, smoking history, surgical approach, perioperative therapeutic regimen. Blood and plasma samples collected before surgery on the DOS were processed as described in Study 1 and analyzed using a multi-omic combination of mass cytometry and multiplex plasma proteomics. The plasma proteomic platform used for Study 2 is the aptamer-based platform Somalogic. (See e.g., L. Gold et al., PloS one 5, e15004, 2010; the disclosure of which is hereby incorporated by reference herein in its entirety.) that allowed quantification of over 2400 circulating proteins. The MOB predictive modeling pipeline was applied to build a predictive model differentiating patients with and without SSCs.

Results: Application of the MOB method to the combined mass cytometry and plasma proteomic DOS dataset collected before surgery identified a multivariate model that classified patients who developed an SSC from controls with high accuracy (AUC=0.77, 95% CI [0.66-0.89], unpaired Mann-Whitney rank-sum test on the MOB model cross-validated values, FIG. 6).

Conclusions: Results from this independent retrospective study performed on an additional 93 patients confirms the previous results (study 1) and suggest that the integrated analysis of preoperative immunological data using MOB can identify patients at risk for developing an SSC after surgery. In addition, the results obtained using data from a retrospective cohort of matched cases and controls suggest that patient's preoperative immunological states differentiate patients at risk for developing an SSC, independently of major clinical and demographic variables that may be associated with SSCs.

Example 4: Integrated Modeling of Immune Responses 24 h After Surgery Accurately Classifies Patients With Post-Operative SSCs Background: This study employed an integrated predictive modeling approach to determine whether immune responses detectable on POD1, 24 hours after surgery, can differentiate patients who then developed SSC from patients with an uncomplicated surgical recovery.

Methods: Peripheral blood and plasma samples were collected on POD1 after abdominal surgery, in patients enrolled in Study 1 (FIG. 4, FIG. 7, Table 1). Samples were analyzed using a multi-omic combination of mass cytometry (for analysis of immune cell frequency and intracellular signaling responses) and plasma proteomics, as described in Example 1. Predictive modeling of SSCs was performed employing the MOB pipeline.

Results: A predictive MOB model built on the POD1 immunological dataset classified patients who developed SSC with very good performance (AUC=0.86, p=2.48e-04, Mann-Whitney nonparametric unpaired test on the cross-validation MD prediction values, FIG. 7). To account for confounding clinical and demographic variables, a post-hoc confounder analysis was performed on the model cross-validated prediction values. Comparing a generalized linear model with or without the MOB predictions led to a significantly better fit of the model with the SG values (p=2e-07, Chi-sq. test for the deviance between fits, Table 7). Additionally, evaluating with the confounders in a linear model with one confounder at a time showed that the SG model remained highly predictive of SSC when accounting for patient variability in either age, sex, surgery type, preoperative diagnosis or surgery length.

Conclusions: The analysis of immune responses to surgery on POD1 identified a predictive model that accurately classified patients who developed SSCs from those who did not, thereby highlighting biological differences in the response to traumatic injury that may drive the pathogenesis of SSCs. Identification of a predictive MOB model of SSCs on POD1 that precede the onset of an SSC is clinically relevant as it allows for preemptive interventions preventing SSCs.

Example 5: Single-Cell Immune Responses and Plasma Proteomic Biological Features Contributing to Integrated Predictive Models of SSCs Background: The multivariate MOB predictive pipeline provided statistically robust models that accurately classified patients with and without SSC from the analysis of biological and clinical data obtained before (DOS model) or shortly after (POD1 model) surgery. To understand the biological implications of the high-dimensional MOB models, individual MOB features that contributed the most to the multivariate models were examined in more detail.

Methods: Individual MOB model features were ranked according to their relative contribution to the multivariate MOB model using an iterative "bootstrap" procedure (i.e., 1000 iterations of resampling the data with replacement) (FIGS. 2, 3A, and 3B). Features were ranked using an objective relative model contribution index (MCI) and the most informative single-cell immune response and plasma proteomic features (MCI [feature]>MCI [decoy feature]) were objectively selected.

Figure 8A:
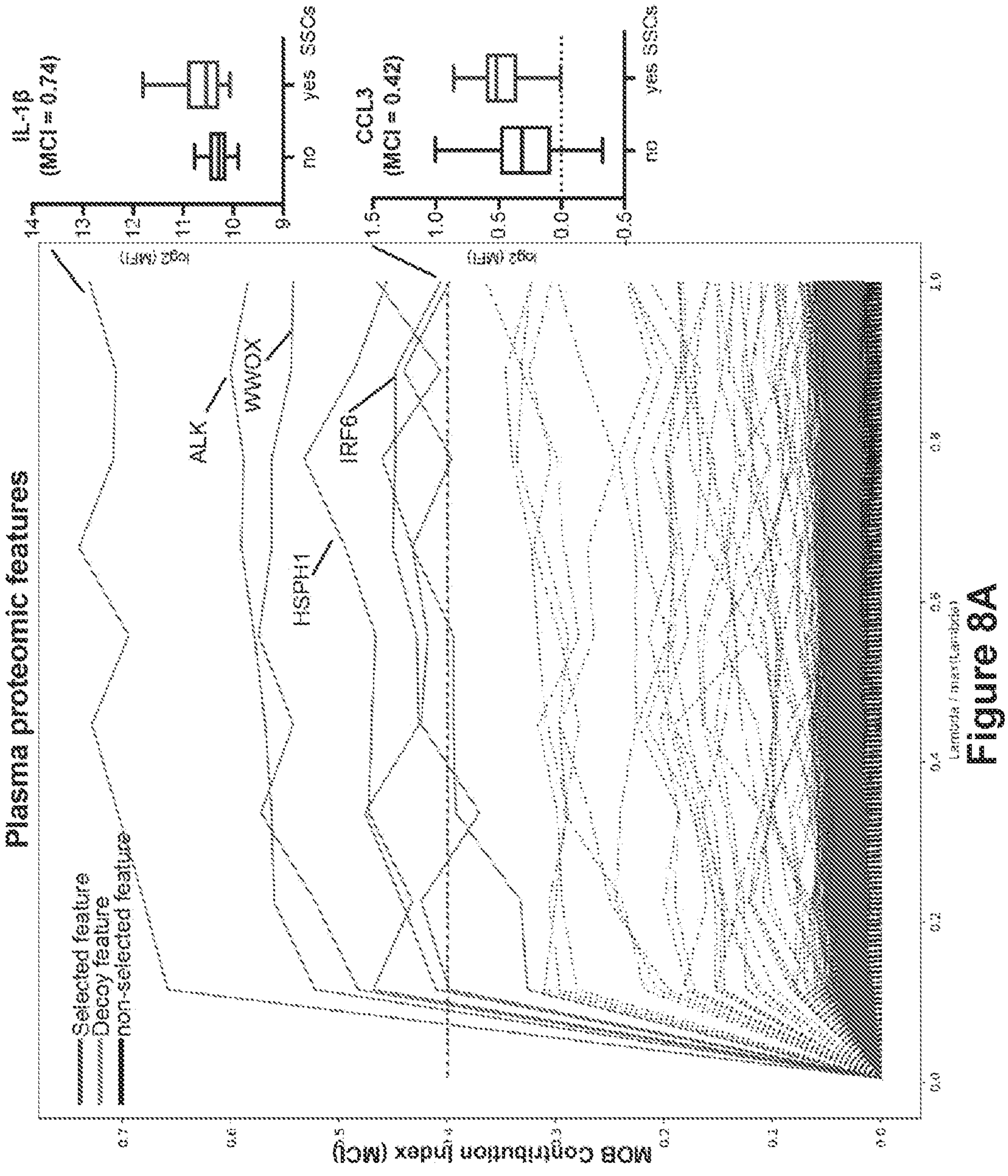
FIGS. 8A-8D illustrate exemplary single cell immune response and proteomic features contributing to the DOS MOB predictive models of SSC in accordance with various embodiments.
Figure 8B:
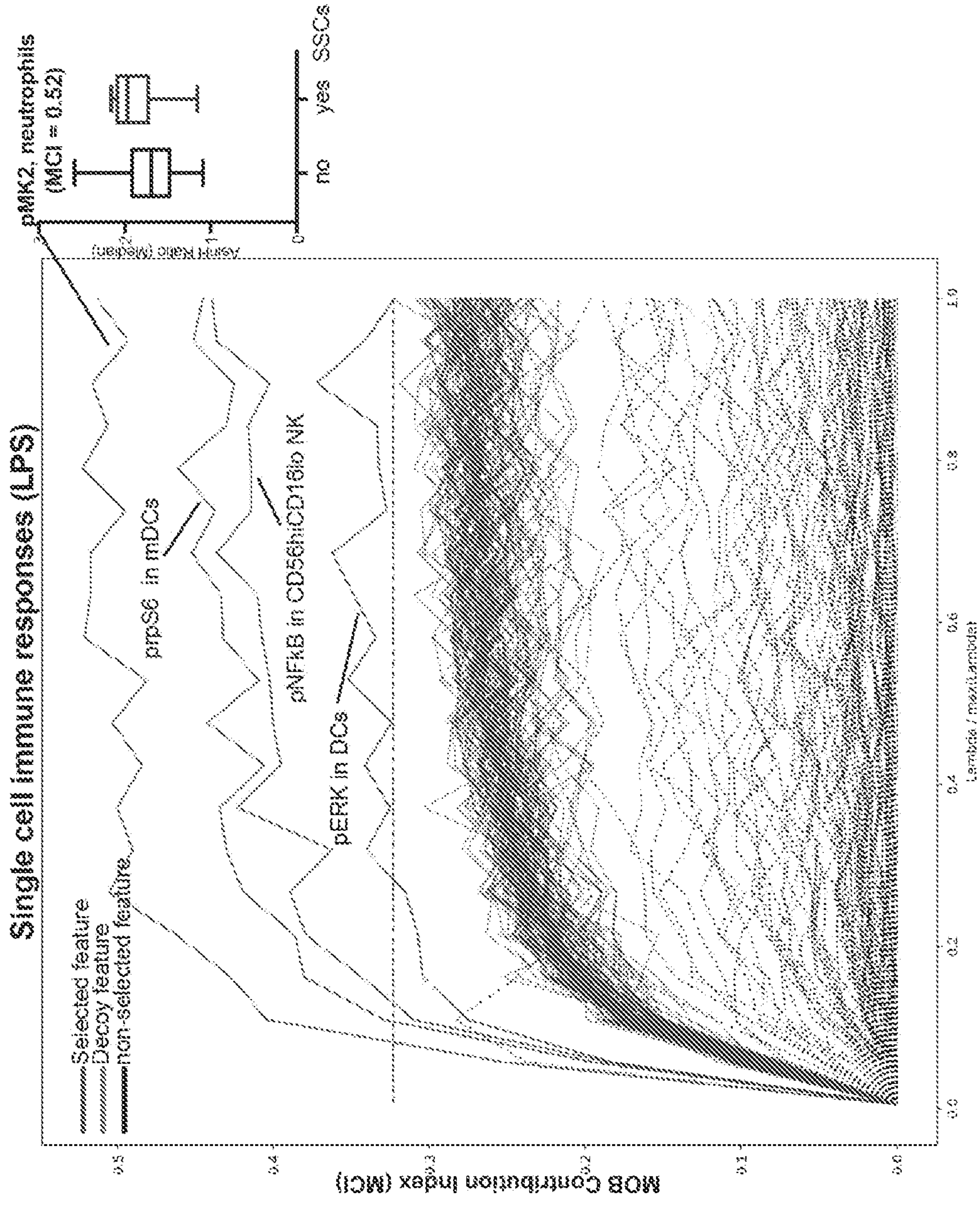
Figure 8C:
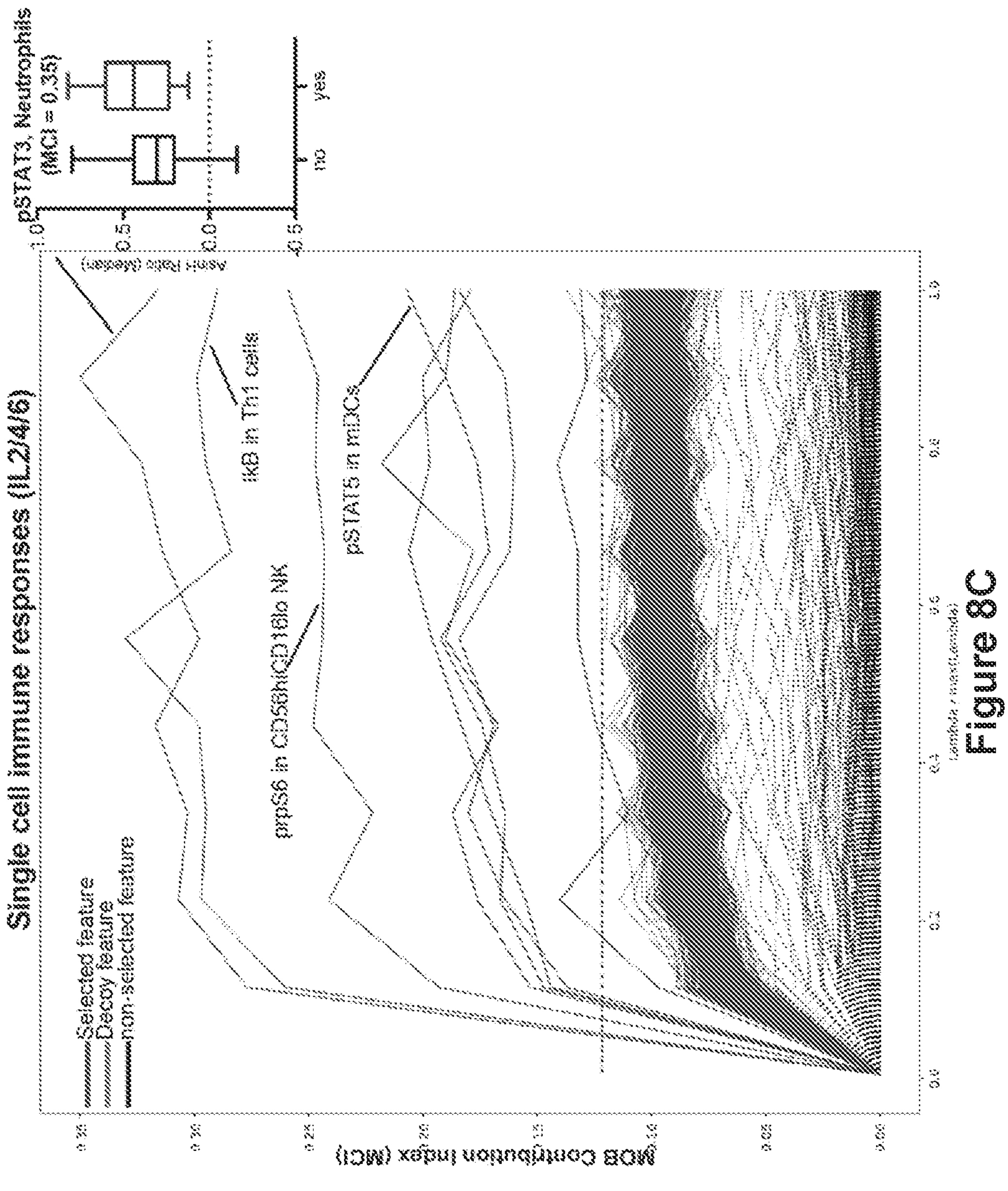
Figure 8D:
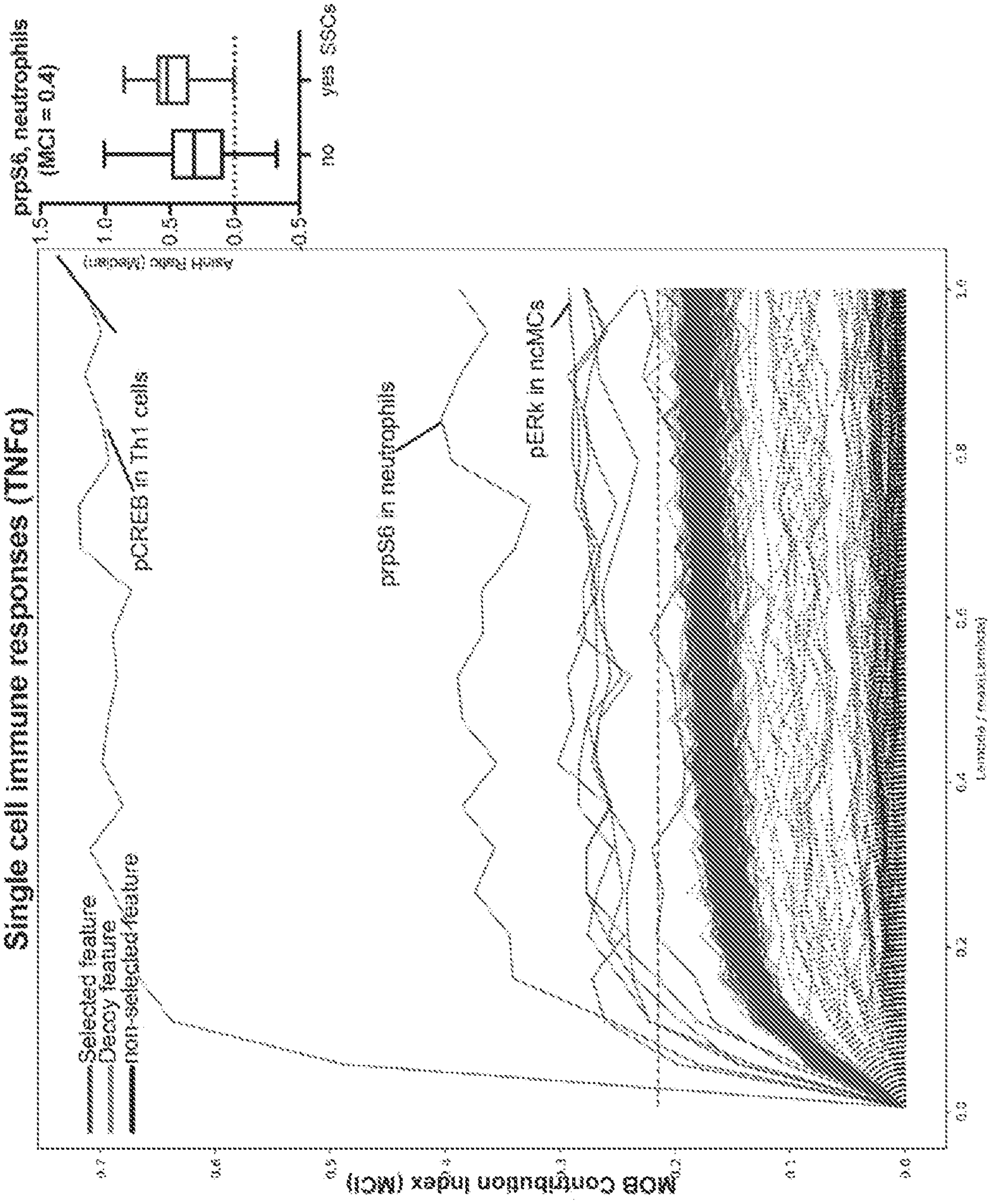

Results: Application of the iterative bootstrap MOB procedures to the multi-omic biological data obtained before surgery (Study 1 and Study 2) selected 55 features that contributed most to the multivariate MOB models (FIGS. 8A-8D, Table 3). Specifically, FIG. 8A illustrates informative DOS MOD model single-cell immune features selected from the plasma proteomic data layer; FIG. 8B illustrates informative DOS MOD model single-cell immune features selected from the LPS data layer; FIG. 8C illustrates informative DOS MOD model single-cell immune features selected from the IL2/4/6 data layer; and FIG. 8D illustrates informative DOS MOD model single-cell immune features selected from the TNFα data layer. graph on the left depicts the probability of selection of individual features from the real or decoy dataset with every bootstrap iteration. Box and whisker graph on the right shows examples of the most informative features for each single cell data layer. The list of MOD model informative features is provided in Table 3 (DOS model) and Table 4 (POD1 model).

Plasma proteomic features included 12 plasma proteins (IL-1β, ALK, WWOX, HSPH1, IRF6, CTNNA3, CCL3, sTREM1, ITM2A, TGFα, LIF, ADA) that were increased, and 4 plasma proteins (ITGB3, EIF5A, KRT19, NTproBNP) that were decreased in patients who later developed an SSC. Single cell immune response features included 4 LPS-response features (increased pMAPKAPK2 (pMK2) in neutrophils, prpS6 in mDCs, and decreased IκB in neutrophils, pNFκB in $CD7^{+}CD56^{hi}CD16^{lo}$ NK cells), 9 IL-2/IL-4/IL-6 response features (increased pSTAT3 in neutrophils, mDCs, or Tregs, increased prpS6 in $CD56^{hi}CD16^{lo}$ NK cells or mDCs, increase pSTAT5 in mDCs, or pDCs, and decreased IκB in $CD4^+Tbet^+$ Th1 cells, decreased pSTAT1 in pDCs), 11 TNFα response features (increased prpS6 in neutrophils or mDCs, increased pERK in M-MDSCs or ncMCs, increased pCREB in γδT Cells or decrease IκB, pP38 or pERK in neutrophils or decreased pCREB or pMAPKAPK2 in $CD4^+Tbet^+$ Th1 cells or decreased pERK in $CD4^+$ $CRTH2^+$ Th2 cells), 10 unstimulated features (increased pSTAT3 in neutrophils, M-MDSCs, cMCs, or ncMCs, increased pSTAT5 in Tregs or $CD45RA^-$ memory $CD4^+$T cells, increased pMAPKAPK2 in mDCs, pCREB or IκB in $CD4^+Tbet^+$ Th1 cells, increased pSTAT6 in NKT cells, or decreased pERK in $CD4^+Tbet^+$ Th1 cells) and 5 frequency features (increased M-MDSC, G-MDSC, ncMC, Th17 cells, or decreased $CD4^+CRTH2^+$ Th2 cell) that differentiated patients who later developed an SSC from controls.

Figure 9A:
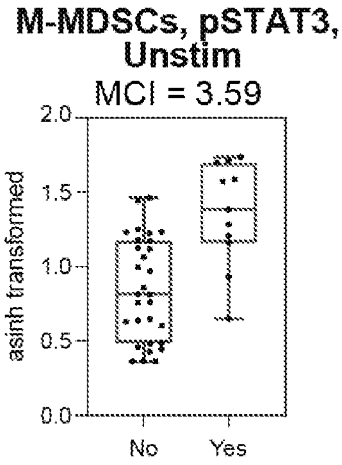
FIGS. 9A-9N illustrate exemplary features contributing to the POD1 MOB predictive models of SSC in accordance with various embodiments of the invention.
Figure 9B:
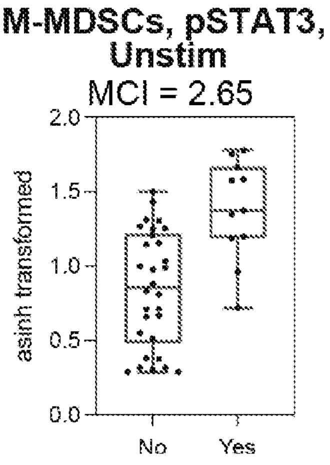
Figure 9C:
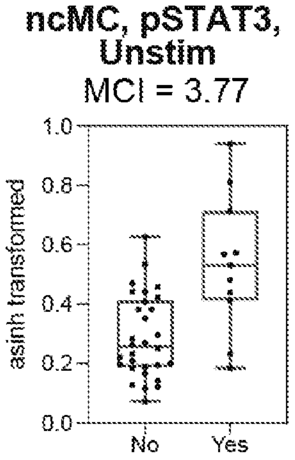
Figure 9D:
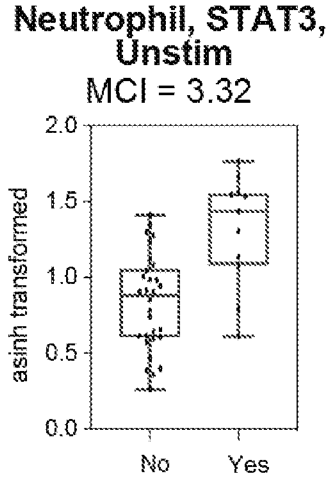
Figure 9E:
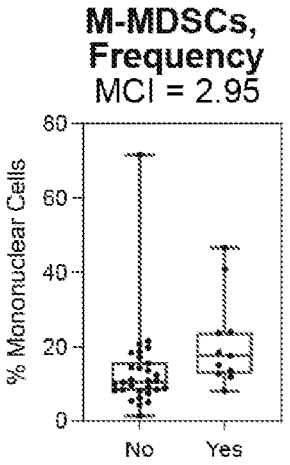
Figure 9F:
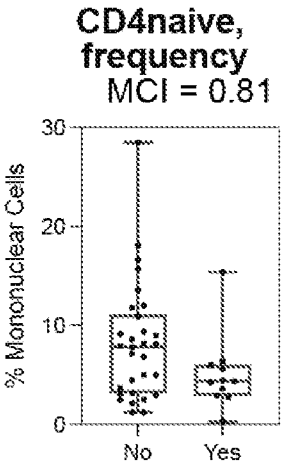
Figure 9G:
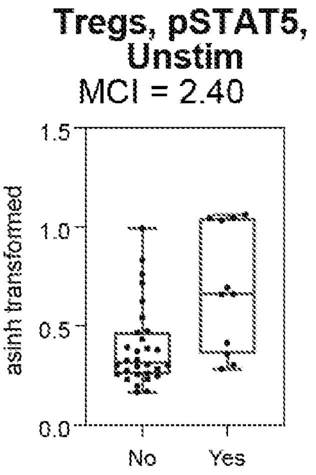
Figure 9H:
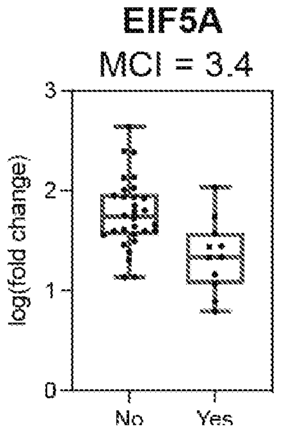
Figure 9I:
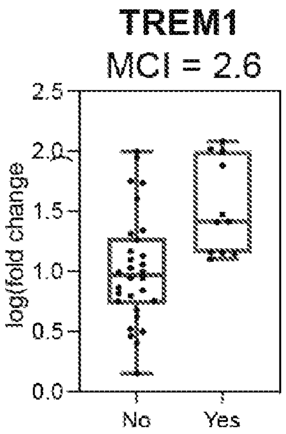
Figure 9J:
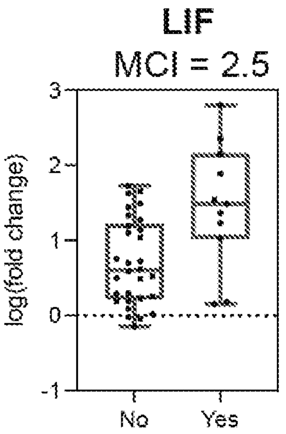
Figure 9K:
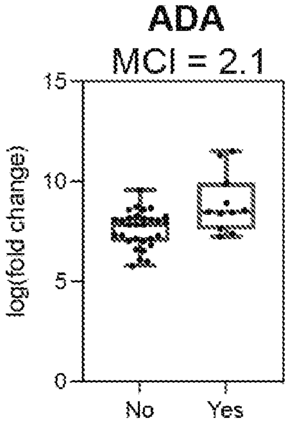
Figure 9L:
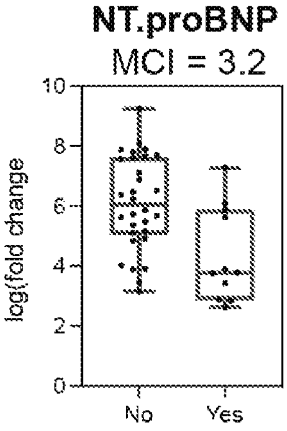
Figure 9M:
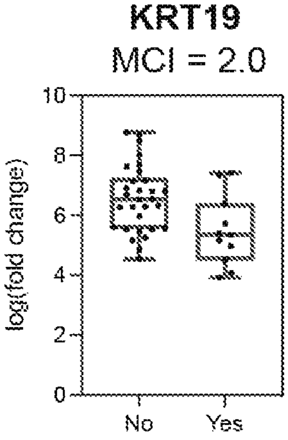
Figure 9N:
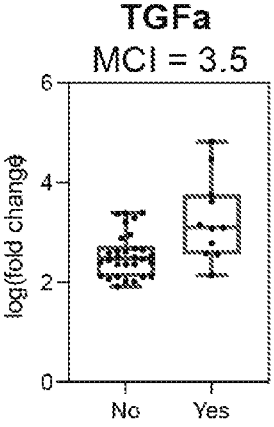

Application of the MOB procedures to the multi-omic biological data obtained 24 hours after surgery (Study 1) selected 16 features that contributed most to the multivariate POD1 model (FIGS. 9A-9N, Table 4). Specifically, FIGS. 9A-9G illustrate single cell immune response features contributing to the POD1 MOB predictive models of SSC, while FIGS. 9H-9N illustrate plasma proteomic features contributing to the POD1 MOB predictive models of SSC.

Conclusions: The analysis of plasma-based and single-cell immune events before and shortly after surgery provided a systems level view of trauma-related immune mechanisms associated with the development of an SCC. Two major themes emerged characterizing the early immune response to surgery in patients who later developed an SCC: 1) an exacerbation of pro-inflammatory IL-6R and TLR-related signaling responses and 2) an increase in immunosuppressive cell responses, including M-MDSC and Treg responses.

Key elements of the POD1 SG model integrate well with prior knowledge regarding immune mechanisms predisposing to SSCs. Previous reports indicate that elevated IL-6 plasma concentrations early after surgery correlate with an increased risk of post-operative complications, including infections. Consistent with prior findings, the increased STAT3 signaling activity in cMCs (canonically activated by IL-6) was one of the most informative single-cell features associated with SSCs. Similarly, exacerbation of MyD88 signaling responses to LPS in innate myeloid cells in patients who later developed an SSC echoes prior results indicating that unchecked, systemic activation of pro-inflammatory innate immune cells in response to surgical site injury may contribute to the development of an SSC. As such, an excessive local immune response to inflammation can amplify the release of DAMPs and PAMPs from the surgery site in a cycle of intensifying MyD88-related TLR signaling, induction of barrier breakdown, and additional tissue damage. In this context it is also noteworthy that overstimulation of TLR signaling can produce a state of endotoxin tolerance, which may increase a patient's susceptibility to infection.

The single-cell resolution afforded by mass cytometry provided new insight into cell-type specific responses that may contribute to the pathogenesis of SSCs. Increased STAT3 signaling in M-MDSCs and increased M-MDSC frequencies at 24 h after surgery were among the most informative features of the POD1 model. The results dovetail with prior studies of patients undergoing orthopedic surgery that show a strong correlation between STAT3 signaling in MDSCs and delayed surgical recovery. MDSCs are a heterogenous subset of immature myeloid cells with immunosuppressive function that are mobilized in the context of acute and chronic inflammatory diseases. In previous investigations of the immune response to trauma and sepsis, MDSCs have been identified as important players in a counter-inflammatory program that represses the adaptive immune system, particularly antigen-specific $CD8^+$ and $CD4^+$ T cell responses. In patients who later developed an SSC, elevated STAT3 signaling, which is required for MDSC's proliferation and immunosuppressive function, could synergistically promote MDSC expansion and, therefore, aggravate a state of immunosuppression.

We also observed the upregulation of endogenous STAT5 signaling in immunosuppressive Tregs in patients who developed an SSC. In contrast, the pSTAT5 response to ex vivo stimulation with IL-2/4/6 was lower in patients who developed an SSC, which may indicate that higher endogenous pSTAT5 signaling tone may prevent further ex vivo activation. IL-2R-dependent activation of STAT5 in Tregs is essential for mature Tregs to maintain FoxP3 expression levels and to exert their immunosuppressive function. Reportedly, FoxP3 expression and Treg-lineage-specific transcription is further promoted by the IL-6 family cytokine LIF. The regulatory functions of LIF in the induction of Treg development and maturation are indicative of the ambiguous role of IL-6-family cytokines in the context of inflammation and trauma. Overall, excessive endogenous Treg signaling could synergize with the observed exaggerated MDSC response and initiate a sustained immunosuppressive state that dampens the response to invading pathogens in patients who develop an SSC.

While the POD1 model provided important information as to surgery-induced mechanisms implicated in the pathogenesis of SSC, the DOS SG model pointed at single-cell features and plasma proteomic factors differentiating the two patient groups before surgery. The most informative features of the DOS SG model were the proteomic features IL-1β, sTREM1 and ITM2A. Our result showing that sTREM1 is elevated on DOS and on POD1 in patients who later develop SSC is reminiscent of previous studies showing increased sTREM1 plasma concentration in patients with bacterial infection and sepsis. From a mechanistic standpoint, sTREM1 is the metalloprotease-cleaved product of membrane-bound TREM1, an amplifier of pattern recognition receptors on myeloid cells. sTREM1 can function as a decoy receptor that antagonizes TREM1. However, microbial products such as LPS can both increase the membrane expression of TREM1 and stimulate the release of sTREM1, thereby increasing sTREM1 plasma concentration. Whether elevated sTREM1 in patients with SSC parallels TREM1 expression on myeloid cells, or results in the functional inhibition of TREM1 is an important question that warrants further investigation.

ITM2A, another proteomic feature of the DOS model, is upregulated by PKA-CREB signaling and leads to an accumulation of autophagosomes and inhibition of autolysosomal formation. Effective autophagy is essential for many physiological functions including tissue differentiation, cell cycle regulation, and immune cell maturation, particularly Th cell development. Other informative features of the DOS model included differences across multiple innate and adaptive cell subsets, such as neutrophils, pDCs, and Th2 cells. Notably, in patients who developed SSC, the signaling responses to multiple stimulations (including IL-1β, TNFα, and IFNα) were dampened in $CRTH2^+$ Th2-like $CD4^+$ T cells, which play important roles in defensive immunity against extracellular pathogens and tissue repair. Our results suggests that patient-specific immune states before surgery may increase the risk for developing an SSC. As such, the preoperative assessment of specific immune markers may assist in risk stratifying patients along with applying interventions to attenuate the risk for developing an SSC.

Doctrine of Equivalents

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the foregoing examples and descriptions of various preferred embodiments of the present invention are merely illustrative of the invention as a whole, and that variations in the components or steps of the present invention may be made within the spirit and scope of the invention. Accordingly, the present invention is not limited to the specific embodiments described herein, but, rather, is defined by the scope of the appended claims.

TABLE 1

Patient characteristics-Study 1.

| | No Surgical Site Complication (73%, n = 30) | Surgical Site Complication (27%, n = 11) | p-value |
|---|---|---|---|
| Female, % (n) | 60% (18) | 27.3% (3) | |
| Age, years mean ± SD | 44.2 ± 17.1 | 48.7 ± 14.1 | |
| BMI, mean ± SD | 23.2 ± 4.6 | 27.2 ± 3.9 | 7e-3 |
| Surgical Indication | | | |
| Inflammatory Bowel Disease | 76.7% (23) | 72.7% (8) | |
| Crohn's disease | 53.3% (16) | 36.4% (4) | |
| Ulcerative Colitis | 23.3% (7) | 36.4% (4) | |
| Other non-cancer diagnoses | 23.3% (7) | 27.3% (3) | |
| Preoperative Biologic Therapy | | | |
| Anti-TNFα | 20% (6) | 9.1% (1) | |
| IL-12/23 Inhibitor | 6.7% (2) | 18.2% (2) | |
| Jak Inhibitor | 3.3% (1) | 0 | |
| a4b7 integrin blocker | 3.3% (1) | 0 | |
| Perioperative Systemic Steroids | 83.3% (25) | 63.6% (7) | |
| Preoperative Steroids | 10% (3) | 0 | |
| Intraoperative Dexamethasone | 83.3% (25) | 63.6% (7) | |
| Postoperative Steroids | 10% (3) | 0 | |
| Surgical Approach | | | |
| Minimally Invasive | 46.7% (14) | 9.1% (1) | |
| Open | 53.3% (16) | 90.9% (10) | |
| Operative Duration, minutes, mean ± SD | 150.5 ± 98.9 | 285.1 ± 139.1 | 2e-3 |
| Wound Classification | | | |
| Clean-Contaminated | 73.3% (22) | 36.4% (4) | |
| Contaminated | 23.3% (7) | 54.5% (6) | |
| Infected | 3.3% (1) | 9.1% (1) | |
| Intraoperative Blood Loss, mL, mean ± SD | 39.2 ± 34.5 | 118 ± 68.1 | 3e−4 |
| Intraoperative Blood Transfusion | 0 | 9.1% (1) | |
| Postoperative Blood Transfusion | 3.3% (1) | 0 | |
| Length of Hospitalization, days, mean ± SD | 4.5 ± 2.1 | 7.6 ± 6.7 | |

TABLE 2

Patient characteristics-Study 2.

| Feature | No Post-operative Complication, 83% (n = 77) | Surgical Site Infection, 17% (n = 16) |
|---|---|---|
| age (mean +/− SD) | 58.8 +/− 14.1 | 58.8 +/− 14.2 |
| male, % (n) | 49 (38) | 50 (8) |
| bmi | 28.3 +/− 6.5 | 26.6 +/− 4.6 |
| surgical indication | | |
| cancer | 58% (45) | 25% (4) |
| inflammatory bowel disease | 6% (5) | 12.5% (2) |
| other | 36% (27) | 62.5 (10) |
| type of surgery | | |
| colectomy | 64% (50) | 56% (9) |
| small bowels | 2% (2) | 6% (1) |
| other | 34% (25) | 37% (6) |
| surgical approach | | |
| minimally invasive | 34% (26) | 32% (5) |
| open surgery | 66% (51) | 68% (11) |
| operative duration, min, mean ± SD | 213 +/− 131 | 234 +/−111 |
| ASA classification | 3 | 3 |

TABLE 3

MOD model features, DOS

| Circulating proteins | increased/decreased in SSCs |
|---|---|
| IL1β | increased |
| ALK | increased |
| WWOX | increased |
| HSPH1 | increased |
| IRF6 | increased |
| CTNNA3 | increased |
| CCL3 | increased |
| ITGAV\|ITGB3 | decreased |
| TREM1 | increased |
| ITM2A | increased |
| Immune response to LPS | |
| Neutrophils, pMAPKAPK2 | increased |
| mDC, prpS6 | increased |
| CD56brightCD16nloNK, pNFkB | decreased |
| Neutrophils, IκB, LPS | decreased |
| Immune response to IL2/4/6 | |
| Neutrophils, pSTAT3 | increased |
| Th1mem, IkB | decreased |
| CD56brightCD16loNK, prpS6 | increased |
| mDC, pSTAT5 | increased |
| mDC, pSTAT3 | increased |
| Tregs, pSTAT3 | increased |
| pDC, STAT5 | increased |
| mDC, prS6 | increased |
| pDC, pSTAT1, IL246 | decreased |
| NKT, pCREB, IL246 | increased |
| Immune response to TNFα | |
| Th1, pCREB | decreased |
| CXCR4 + Neutrophils, prpS6 | increased |
| ncMC, pERK | increased |
| gdT, pCREB | increased |
| Neutrophils, pP38 | decreased |
| mDC, prpS6 | increased |
| M-MDSC, pERK | increased |
| Neutrophils, S6 | increased |
| Th2, pERK1/2, TNFα | decreased |
| Neutrophils, IκB, TNFα | decreased |
| Th1, pMAPKAPK2, TNFα | decreased |
| Neutrophils, pERK1/2, TNFα | increased |

TABLE 3-continued

| MOD model features, DOS | |
|---|---|
| Circulating proteins | increased/decreased in SSCs |
| Immune response, unstimulated | |
| Th1naive, pCREB | increased |
| Th1naive, pERK | decreased |
| Treg, pSTAT5 | increased |
| Th1naive, IkB | increased |
| CXCR4 + neutrophils, prpS6 | increased |
| CD4Trm, pSTAT5 | increased |
| NKT, pSTAT6 | increased |
| mDC, pMAPKAPK2 | increased |
| Th2, pERK1/2, Unstim | increased |
| Neutrophils prpS6, Unstim | increased |
| Plasma cells, pSTAT5, Unstim | increased |
| Immune response, frequencies | |
| CD4Trm | decreased |
| Th2 | decreased |
| Plasma cells, frequency | increased |

TABLE 4

| MOD model features, POD1 | |
|---|---|
| Circulating proteins | increased/decreased in SSCs |
| TGFα | increased |
| EIF5A | decreased |
| TREM1 | increased |
| LIF | increased |
| ADA | increased |
| KRT19 | decreased |
| NT.proBNP | decreased |
| Immune response, unstimulated | |
| ncMC, pSTAT3, Unstim | increased |
| CMC, pSTAT3, Unstim | increased |
| Neutrophils, pSTAT3, Unstim | increased |
| ncMC, pSTAT4, Unstim | decreased |
| Treg, pSTAT5, Unstim | increased |
| M-MDSC, pSTAT3, Unstim | increased |
| Immune response, frequencies | |
| M-MDSC, Frequency | increased |
| Th17, Frequency | increased |
| intMC, Frequency | increased |

TABLE 5

Mass Cytometry antibody panel (Study 1)

| Metal | Isotope | Marker | Final Conc. (μg/mL) |
|---|---|---|---|
| In | 113 | CD235 | 0.5 |
| In | 113 | CD61 | 0.5 |
| In | 115 | CD45 | 1 |
| La | 139 | CD66 | 1 |
| Pr | 141 | CD7 | 1 |
| Nd | 142 | CD19 | 1 |
| Nd | 144 | CD11b | 1 |
| Nd | 145 | CD4 | 2 |
| Nd | 146 | CD8 | 1 |
| Sm | 147 | CD11c | 1 |
| Eu | 151 | CD123 | 1 |
| Sm | 152 | TCRγδ | 4 |
| Gd | 155 | CD45RA | 0.5 |
| Gd | 156 | CD14 | 4 |
| Gd | 157 | CD38 | 0.5 |

TABLE 5-continued

Mass Cytometry antibody panel (Study 1)

| Metal | Isotope | Marker | Final Conc. (μg/mL) |
|---|---|---|---|
| Gd | 158 | CD33 | 1 |
| Dy | 161 | GPR15 | 4 |
| Dy | 163 | CRTH2 | 4 |
| Dy | 164 | CD161 | 4 |
| Ho | 165 | CD16 | 2 |
| Tm | 169 | CD25 | 2 |
| Er | 170 | CD3 | 1 |
| Yb | 173 | HLADR | 1 |
| Yb | 174 | PD1 | 1 |
| Yb | 176 | CD56 | 1 |
| Nd | 143 | cPARP | 1 |
| Nd | 148 | pSTAT4 | 4 |
| Sm | 149 | CREB | 1 |
| Nd | 150 | pSTAT5 | 4 |
| Eu | 153 | pSTAT1 | 1 |
| Sm | 154 | pSTAT3 | 4 |
| Tb | 159 | pMAPKAP2 | 1 |
| Gd | 160 | Tbet | 8 |
| Dy | 162 | FOXP3 | 10 |
| Er | 166 | pNFκB | 2 |
| Er | 167 | PERK1/2 | 1 |
| Er | 168 | Ki67 | 4 |
| Yb | 171 | IκB | 8 |
| Yb | 172 | pS6 | 2 |
| Lu | 175 | pSTAT6 | 4 |

TABLE 6

Confounder analysis for the Post-operative Day 1 (POD1) model (Study 1)

| Confounder | Confounder p | Model p |
|---|---|---|
| age | 0.38 | 0.001 |
| BMI | 0.04* | 0.003 |
| Preoperative diagnosis (UC) | 0.26 | 0.002 |
| Preoperative diagnosis (CD) | 0.40 | 0.002 |
| Surgical Approach | 0.44 | 0.002 |
| Operating time (min) | 0.02* | 0.006 |
| Preoperative Biologic Therapy | 0.47 | 0.002 |
| Estimated Blood Loss | 0.02* | 0.03 |

TABLE 7

Confounder analysis for the pre-operative Day of Surgery (DOS) model (Study 1).

| Confounder | Confounder p | Model p |
|---|---|---|
| age | 0.93 | 0.01 |
| BMI | 0.04* | 0.02 |
| Preoperative diagnosis (UC) | 0.30 | 0.01 |
| Preoperative diagnosis (CD) | 0.47 | 0.01 |
| Surgical Approach | 0.87 | 0.01 |
| Preoperative Biologic Therapy | 0.68 | 0.02 |

UC: Ulcerative colitis;
CD: Crohn's Disease

What is claimed is:

1. A method for assessing immune activation of a patient for determining a surgical risk score indicative the patient's risk for a surgical complication following surgery, comprising:

collecting one or more samples from the patient, obtaining an ex-vivo-stimulation sample, wherein the ex-vivo-stimulation sample is or is derived from the one or more samples from the patient, wherein the ex-vivo-stimulation sample comprises immune cells that are collected prior to a surgical procedure to be performed on the patient;

measuring values of a plurality of omic biological features, wherein the plurality of omic biological features comprises a set of one or more immune-activation measurements of the patient, wherein each immune-activation measurement of the set is an amount of activation of an immune-related signaling protein yielded by ex vivo stimulation and is determined by:

incubating the ex-vivo-stimulation sample with one or more immune activating agents selected from the group consisting of: a Toll-Like Receptor 4 (TLR4) agonist, interleukin-2 (IL-2), interleukin-4 (IL-4), interleukin-6 (IL-6), interleukin-1β (IL-1β), Tumor Necrosis Factor-α (TNF-α), Interferon-α (IFN-α), and phorbol 12-myristate 13-acetate (PMA)/ionomycin; and measuring an amount of activation of an immune-related signaling protein of the immune cells within the ex-vivo-stimulation sample by:

contacting the immune cells with an affinity reagent that binds to the immune-related signaling protein in an activated state, and measuring an amount of binding of the affinity reagent to the immune-related signaling proteins in the activated state;

wherein the measuring the amount of activation of the immune-related signaling protein is performed subsequent to incubating the ex-vivo-stimulation sample with one or more immune activating agents; and computing a surgical risk score for the patient by entering the values of the plurality of omic biological features into a machine learning model trained to generate surgical risk scores wherein the surgical risk score comprises a probability that the patient will develop a surgical site complication following the surgical procedure to be performed on the patient;

wherein the machine learning model is trained using a bootstrap procedure on a plurality of individual data layers; wherein each data layer represents one type of data from the plurality of omic biological features and at least one artificial feature, wherein at least one data layer represents a set of one or more immune-activation measurements of the patient of which each immune-activation measurement of the set is the amount of activation of the immune-related signaling protein yielded by the ex vivo stimulation;

wherein each data layer comprises data for a population of individuals; wherein each omic biological feature includes feature values for all individuals in the population of individuals; wherein, for a respective data layer, each artificial feature is a new variable obtained from a non-artificial feature among the plurality of omic biological features via a mathematical operation performed on the feature values of the non-artificial feature;

wherein the mathematical operation being chosen among the group consisting of:

a permutation, a sampling with replacement, a sampling without replacement, a combination, a knockoff and an inference wherein the machine learning model includes weights for a set of biological omic features of the plurality of omic biological features;

wherein during training of the machine learning model and for each data layer, for every repetition of the bootstrap, initial weights are computed for the plurality of omic biological features and the at least one artificial feature associated with that data layer using an initial statistical learning technique, and at least one selected feature is determined for each data layer, based on a statistical criteria depending on the computed initial weights; and wherein the statistical criteria depends on significant weights among the computed initial weights;

the significant weights being non-zero weights, when an initial statistical learning technique is a sparse regression technique;

the significant weights being weights above a predefined weight threshold, when the initial statistical learning technique is a non-sparse regression technique wherein the statistical criteria is based on an occurrence frequency of the significant weights.

2. The method of claim 1, further comprising:

generating values of a plurality of clinical features derived from clinical data obtained from the patient;

wherein computing a surgical risk score further comprises entering the values of the plurality of clinical features into the machine learning model trained to generate surgical risk scores.

3. The method of claim 1, wherein the initial weights are further computed for a plurality of values of a hyperparameter, wherein the hyperparameter is a parameter whose value is used to control training of the machine learning model.

4. The method of claim 1, wherein the initial weights are further computed for a plurality of values of a hyperparameter, wherein the hyperparameter is a parameter whose value is used to control the learning process; and wherein for each feature, a unitary occurrence frequency is calculated for each hyperparameter value and is equal to a number of the significant weights related to said feature for the successive bootstrap repetitions divided by the number bootstrap repetitions.

5. The method of claim 1, the statistical criteria is that each feature is selected when its occurrence frequency is greater than a frequency threshold, the frequency threshold being computed according to the occurrence frequencies obtained for the artificial features.

6. The method of claim 1, wherein during training of the machine learning model, the weights of the model are further computed using a final statistical learning technique on the data associated to the set of selected features.

7. The method of claim 1, wherein during training of the machine learning model, the method further comprises, before obtaining artificial features:

generating additional values of the plurality of non-artificial features based on the obtained values and using a data augmentation technique;

the artificial features being then obtained according to both the obtained values and the generated additional values.

8. The method of claim 1, wherein the pre-surgery sample is or derived from a blood sample, a peripheral blood mononuclear cells (PBMC) fraction of a blood sample, a urine sample, a saliva sample, or dissociated cells from a tissue sample.

9. The method of claim 1, further comprising:

obtaining a cytomic sample, wherein the cytomic sample is or is derived from the one or more samples from the patient, wherein the cytomic sample comprises immune cells derived from the patient that are not further stimulated ex vivo, wherein the plurality of omic biological features comprises a second set of immune-activation measurements of the patient, wherein each immune-activation measurement of the second set is one or both of the following:

an amount of activation of an immune-related signaling protein within unstimulated immune cells of the cytomic sample, or a frequency of an immune cell type within the cytomic sample;

wherein the amount of activation of an immune-related signaling protein within unstimulated immune cells of the cytomic sample is determined by:

measuring an amount of activation of an immune-related signaling protein of the immune cells within the cytomic sample by:

contacting the immune cells with an affinity reagent that binds to the immune-related signaling protein in an activated state, and measuring an amount of binding of the one or more affinity reagents to the immune-related signaling proteins in the activated state;

wherein the frequency of the immune cell type within the cytomic sample is determined by:

contacting the immune cells with an affinity reagent that binds to a surface or intracellular protein that is indicative of an immune cell type; and measuring the frequency of cells with the affinity reagent bound to the surface or intracellular protein.

10. The method of claim 9, wherein the immune-related signaling protein in the activated state is selected from: phospho-Signal Transducer and Activator of Transcription 3 (pSTAT3) in neutrophils, Monocytic Myeloid Derived Suppressor Cells (M-MDSCs), classical Monocytes (cMCs), or non-classical Monocytes (ncMCs), phospho-Signal Transducer and Activator of Transcription 5 (pSTAT5) in regulatory T cells (Tregs) or CD45RA memory $CD4^+$T cells, phospho-Mitogen-Activated Protein Kinase-Activated Protein Kinase (pMAPKAPK2 (pMK2)) in myeloid Dendritic Cells (mDCs), phopsho-cAMP Response Element-Binding Protein (pCREB) or Inhibitor of NFκB (IκB) in $CD4^+$ $Tbet^+$T helper 1 (Th1) cells, phospho-Signal Transducer and Activator of Transcription 6 (pSTAT6) in Natural Killer T (NKT) cells, and phospho-Extracellular signal-Regulated Kinase (pERK) in $CD4^+Tbet^+$T helper 1 (Th1) cells.

11. The method of claim 9, wherein the immune cell type is from: Monocytic Myeloid Derived Suppressor Cells (M-MDSCs), Granulocytic Myeloid Derived Suppressor Cells (G-MDSCs), non-classical Monocytes (ncMCs), T helper 17 (Th17) cells, $CD4^+$-Chemoattractant Receptor-Homologous Molecule Expressed on T helper $2^+$ ($CD4^+$ $CRTH2^+$), and T helper 2 (Th2) cell.

12. The method of claim 1, further comprising:

obtaining a proteomic sample, wherein the proteomic sample is or is derived from the one or more samples from the patient, wherein proteomic sample comprises circulating extracellular proteins derived from blood of the patient; wherein the plurality of omic biological features comprises a second set of immune-activation measurements of the patient, wherein each immune-activation measurement of the second set is:

an amount of a circulating extracellular protein that is determined by:

contacting the proteomic sample with one or more affinity reagents that bind to the circulating extracellular protein; and measuring an amount of binding of the one or more affinity reagents to the extracellular protein.

13. The method of claim 12, wherein the circulating extracellular protein is selected from: interleukin-1β (IL-1β), anaplastic lymphoma kinase (ALK), WW domain-containing oxidoreductase (WWOX), heat shock protein family H member 1 (HSPH1), interferon regulatory factor 6 (IRF6), catenin alpha 3 (CTNNA3), C-C Motif Chemokine Ligand 3 (CCL3), soluble Triggering Receptor Expressed On Myeloid Cells 1 (sTREM1), Integral Membrane Protein 2A (ITM2A), Transforming Growth Factor α (TGFα), LIF Interleukin 6 Family Cytokine (LIF), Adenosine Deaminase (ADA), Integrin Subunit Beta 3 (ITGB3), Eukaryotic Translation Initiation Factor 5A (EIF5A), Keratin 19 (KRT19U), and N-terminal prohormone of brain natriuretic peptide (NTproBNP).

14. The method of claim 1, wherein the immune-related signaling protein in the activated state is selected from: phospho-Mitogen-Activated Protein Kinase-Activated Protein Kinase (pMAPKAPK2 (pMK2)) in neutrophils, phospho-ribosomal protein S6 (prpS6) in myeloid Dendritic Cells (mDCs), phospho-Nuclear Factor Kappa B (pNFκB) in $CD7^+CD56^{hi}CD16^{lo}$ Natural Killer (NK) cells, and Inhibitor of NFκB (IκB) in neutrophils, wherein the one or more immune activating agents comprises Lipopolysaccharide (LPS).

15. The method of claim 1, wherein the immune-related signaling protein in the activated state is selected from: phospho-Signal Transducer and Activator of Transcription 3 (pSTAT3) in neutrophils, myeloid Dendritic Cells (mDCs), or regulatory T cells (Tregs), phospho-ribosomal protein S6 (prpS6) in $CD56^{hi}CD16^{lo}$ Natural Killer (NK) cells or myeloid Dendritic Cells (mDCs), phospho-Signal Transducer and Activator of Transcription 5 (pSTAT5) in myeloid Dendritic Cells (mDCs), or plasmacytoid Dendritic Cells (pDCs), Inhibitor of NFκB (IκB) in $CD4^+Tbet^+$T helper 1 (Th1) cells, and phospho-Signal Transducer and Activator of Transcription 1 (pSTAT1) in plasmacytoid Dendritic Cells (pDCs), wherein the one or more immune activating agents comprises interleukin-2 (IL-2), interleukin-4 (IL-4), and/or interleukin-4 (IL-6).

16. The method of claim 1, wherein the immune-related signaling protein in the activated state is selected from: phospho-ribosomal protein S6 (prpS6) in neutrophils or myeloid Dendritic Cells (mDCs), phospho-Extracellular signal-Regulated Kinase (pERK) in Monocytic Myeloid Derived Suppressor Cells (M-MDSCs) or non-classical Monocytes (ncMCs), phopsho-cAMP Response Element-Binding Protein (pCREB) in γδT Cells, Inhibitor of NFκB (IκB), phospho-P38 (pP38) or phospho-Extracellular signal-Regulated Kinase (pERK) in neutrophils, phopsho-cAMP Response Element-Binding Protein (pCREB) or phospho-Mitogen-Activated Protein Kinase-Activated Protein Kinase (pMAPKAPK2 (pMK2)) in $CD4^+Tbet^+$T helper 1 (Th1) cells, and phospho-Extracellular signal-Regulated Kinase (PERK) in $CD4^+CRTH2^+$T helper 2 (Th2) cells, wherein the one or more immune activating agents comprises Tumor Necrosis Factor-α (TNF-α).

17. The method of claim 1 further comprising:

administering the surgical procedure on the patient;

wherein when the surgical risk score is above a threshold, the method further comprises:

administering a treatment regimen to the patient that is configured to reduce the probability that the patient develops a surgical site complication.

18. The method of claim 17, wherein the treatment regimen comprises:

administering an antibiotic or immune modulator to the patient.

19. The method of claim 17, wherein administering the surgical procedure comprises reducing the probability that the patient develops a surgical site complication by:

delaying or adjusting the timing of surgery, or adjusting the surgical approach.

20. A method for assessing immune activation of a patient for determining a surgical risk score indicative the patient's risk for a surgical complication following surgery, comprising:

collecting one or more samples from the patient, obtaining an ex-vivo-stimulation sample, wherein the ex-vivo-stimulation sample is or is derived from the one or more samples from the patient, wherein the ex-vivo-stimulation sample comprises immune cells that are collected prior to a surgical procedure to be performed on the patient;

measuring values of a plurality of omic biological features, wherein the plurality of omic biological features comprises a set of one or more immune-activation measurements of the patient, wherein each immune-activation measurement of the set is an amount of activation of an immune-related signaling protein yielded by ex vivo stimulation and is determined by:

incubating the ex-vivo-stimulation sample with one or more immune activating agents selected from the group consisting of: a Toll-Like Receptor 4 (TLR4) agonist, interleukin-2 (IL-2), interleukin-4 (IL-4), interleukin-6 (IL-6), interleukin-1β (IL-1β), Tumor Necrosis Factor-α (TNF-α), Interferon-α (IFN-α), and phorbol 12-myristate 13-acetate (PMA)/ionomycin; and measuring an amount of activation of an immune-related signaling protein of the immune cells within the ex-vivo-stimulation sample by:

contacting the immune cells with an affinity reagent that binds to the immune-related signaling protein in an activated state, and measuring an amount of binding of the affinity reagent to the immune-related signaling proteins in the activated state;

wherein the measuring the amount of activation of the immune-related signaling protein is performed subsequent to incubating the ex-vivo-stimulation sample with one or more immune activating agents; and computing a surgical risk score for the patient by entering the values of the plurality of omic biological features into a machine learning model trained to generate surgical risk scores wherein the surgical risk score comprises a probability that the patient will develop a surgical site complication following the surgical procedure to be performed on the patient;

wherein the machine learning model is trained using a bootstrap procedure on a plurality of individual data layers; wherein each data layer represents one type of data from the plurality of omic biological features and at least one artificial feature, wherein at least one data layer represents a set of one or more immune-activation measurements of the patient of which each immune-activation measurement of the set is the amount of activation of the immune-related signaling protein yielded by the ex vivo stimulation;

wherein each data layer comprises data for a population of individuals; wherein each omic biological feature includes feature values for all individuals in the population of individuals; wherein, for a respective data layer, each artificial feature is a new variable obtained from a non-artificial feature among the plurality of omic biological features via a mathematical operation performed on the feature values of the non-artificial feature;

wherein the mathematical operation being chosen among the group consisting of:

a permutation, a sampling with replacement, a sampling without replacement, a combination, a knockoff and an inference wherein the machine learning model includes weights for a set of biological omic features of the plurality of omic biological features;

wherein during training of the machine learning model and for each data layer, for every repetition of the bootstrap, initial weights are computed for the plurality of omic biological features and the at least one artificial feature associated with that data layer using an initial statistical learning technique, and at least one selected feature is determined for each data layer, based on a statistical criteria depending on the computed initial weights; and wherein the initial weights are further computed for a plurality of values of a hyperparameter, wherein the hyperparameter is a parameter whose value is used to control the learning process; and wherein for each feature, a unitary occurrence frequency is calculated for each hyperparameter value and is equal to a number of the significant weights related to said feature for the successive bootstrap repetitions divided by the number bootstrap repetitions.

* * * * *